US008795667B2

(12) United States Patent
Johnson et al.

(10) Patent No.: US 8,795,667 B2
(45) Date of Patent: Aug. 5, 2014

(54) COMPOSITIONS FOR THE PREVENTION AND TREATMENT OF SMALLPOX

(75) Inventors: Leslie S. Johnson, Darnestown, MD (US); Ling Huang, Bethesda, MD (US)

(73) Assignee: MacroGenics, Inc., Rockville, MD (US)

( * ) Notice: Subject to any disclaimer, the term of this patent is extended or adjusted under 35 U.S.C. 154(b) by 305 days.

(21) Appl. No.: 12/338,142

(22) Filed: Dec. 18, 2008

(65) Prior Publication Data

US 2009/0162353 A1 Jun. 25, 2009

Related U.S. Application Data

(60) Provisional application No. 61/015,106, filed on Dec. 19, 2007.

(51) Int. Cl.
*A61K 39/285* (2006.01)
*A61K 39/00* (2006.01)

(52) U.S. Cl.
USPC ............... 424/147.1; 530/387.1; 530/387.3; 530/388.1; 530/388.3; 424/133.1; 424/159.1; 424/139.1; 536/23.5; 435/69.1; 435/320.1; 435/325; 435/339; 435/331

(58) Field of Classification Search
None
See application file for complete search history.

(56) References Cited

U.S. PATENT DOCUMENTS

| | | | |
|---|---|---|---|
| 4,752,601 A | 6/1988 | Hahn | |
| 5,348,876 A | 9/1994 | Michaelsen et al. | |
| 5,576,184 A | 11/1996 | Better et al. | |
| 5,585,089 A | 12/1996 | Queen et al. | |
| 5,624,821 A | 4/1997 | Winter et al. | |
| 5,648,260 A | 7/1997 | Winter et al. | |
| 5,698,449 A | 12/1997 | Baumann et al. | |
| 5,723,584 A | 3/1998 | Schatz | |
| 5,736,135 A | 4/1998 | Goeddel et al. | |
| 5,736,137 A | 4/1998 | Anderson et al. | |
| 5,874,239 A | 2/1999 | Schatz | |
| 5,932,433 A | 8/1999 | Schatz | |
| 5,985,599 A | 11/1999 | Mckenzie et al. | |
| 6,025,485 A | 2/2000 | Kamb et al. | |
| 6,114,147 A | 9/2000 | Frenken et al. | |
| 6,165,745 A | 12/2000 | Ward et al. | |
| 6,194,551 B1 | 2/2001 | Idusogie et al. | |
| 6,242,195 B1 | 6/2001 | Idusogie et al. | |
| 6,277,375 B1 | 8/2001 | Ward | |
| 6,300,065 B1 | 10/2001 | Kieke et al. | |
| 6,423,538 B1 | 7/2002 | Wittrup et al. | |
| 6,451,309 B2 * | 9/2002 | Hooper et al. ............. 424/147.1 |
| 6,455,263 B2 | 9/2002 | Payan | |
| 6,492,123 B1 | 12/2002 | Hollinger et al. | |
| 6,528,624 B1 | 3/2003 | Idusogie et al. | |
| 6,538,124 B1 | 3/2003 | Idusogie et al. | |
| 6,620,412 B2 | 9/2003 | Hooper et al. | |
| 6,737,056 B1 | 5/2004 | Presta | |
| 6,821,505 B2 | 11/2004 | Ward | |
| 7,122,646 B2 | 10/2006 | Hollinger et al. | |
| 7,914,788 B2 * | 3/2011 | Chen et al. ............... 424/141.1 |
| 7,943,742 B2 * | 5/2011 | Violette et al. ............ 530/387.3 |
| 2002/0176871 A1 * | 11/2002 | Hooper et al. ............ 424/232.1 |
| 2003/0077282 A1 | 4/2003 | Bigler et al. | |
| 2003/0158389 A1 | 8/2003 | Idusogie et al. | |
| 2004/0002587 A1 | 1/2004 | Watkins et al. | |
| 2004/0110226 A1 | 6/2004 | Lazar et al. | |
| 2004/0132101 A1 | 7/2004 | Lazar et al. | |
| 2004/0185045 A1 | 9/2004 | Koenig et al. | |
| 2004/0220388 A1 * | 11/2004 | Mertens et al. ............ 530/388.8 |
| 2005/0037000 A1 | 2/2005 | Stavenhagen et al. | |
| 2005/0054832 A1 | 3/2005 | Lazar et al. | |
| 2005/0064514 A1 | 3/2005 | Stavenhagen et al. | |
| 2005/0215767 A1 | 9/2005 | Koenig et al. | |
| 2005/0260213 A1 | 11/2005 | Koenig et al. | |
| 2007/0004904 A1 * | 1/2007 | Nissen et al. ................ 530/300 |
| 2007/0004909 A1 | 1/2007 | Johnson et al. | |
| 2007/0036799 A1 | 2/2007 | Stavenhagen et al. | |
| 2007/0077246 A1 | 4/2007 | Koenig et al. | |
| 2007/0244303 A1 | 10/2007 | Johnson et al. | |

FOREIGN PATENT DOCUMENTS

| | | |
|---|---|---|
| EP | 0 327 378 | 8/1989 |
| WO | WO 88/07089 | 9/1988 |
| WO | WO 89/07142 | 8/1989 |
| WO | WO 92/16562 | 10/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 97/28267 | 8/1997 |
| WO | WO 97/34631 | 9/1997 |

(Continued)

OTHER PUBLICATIONS

Fogg, et al. Protective Immunity to Vaccinia Virus Induced by Vaccination with Multiple Recombinant Outer Membrane Proteins of Intracellular and Extracellular Virions. J. Virol. 2004; 78(19): 10230-10237.*

Sawyer, L.A. Antibodies for the prevention and treatment of viral diseases. Antivir. Res. 2000; 47(2): 57-77.*

Holliger and Hudson Nature Biotech. Engineered antibody fragments and the rise of single domains. 2005; 23(9): 1126-1136.*

Lu et al. Di-diabody: a novel tetravalent bispecific antibody molecule by design. J Immunol Methods. Aug. 2003;279(1-2):219-32.*

US 6,331,391, 12/2001, Wittrup et al. (withdrawn).

(Continued)

*Primary Examiner* — Michelle S Horning

(74) *Attorney, Agent, or Firm* — William C. Schrot; Jeffrey I. Auerbach; Auerbach Schrot LLC

(57) ABSTRACT

The present invention relates to improved compositions for the prevention and treatment of smallpox, and in particular to the use of compositions containing an antibody that binds to an epitope found on the MV form of the smallpox virus and an antibody that binds to an epitope found on the EV form of the smallpox virus. The invention relates to such compositions, especially to non-blood derived antibody compositions, such as chimeric or humanized antibodies, and to methods for their use in imparting passive immunity against smallpox infection to individuals at risk of smallpox virus infection or who exhibit smallpox.

19 Claims, 39 Drawing Sheets

(56) References Cited

FOREIGN PATENT DOCUMENTS

| | | |
|---|---|---|
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 00/42072 | 7/2000 |
| WO | 02/02781 A1 | 1/2002 |
| WO | WO 02/060919 | 8/2002 |
| WO | WO 02/086070 | 10/2002 |
| WO | WO 03/074679 | 9/2003 |
| WO | WO 2004/016750 | 2/2004 |
| WO | WO 2004/029207 | 4/2004 |
| WO | WO 2004/065423 | 8/2004 |
| WO | WO 2004/074455 | 9/2004 |
| WO | WO 2004/099249 | 11/2004 |
| WO | WO 2005/070963 | 8/2005 |
| WO | WO 2005/110474 | 11/2005 |
| WO | WO 2006/020114 | 2/2006 |
| WO | WO 2006/066078 | 6/2006 |
| WO | 2009117030 A1 | 9/2009 |

OTHER PUBLICATIONS

Alt et al., "Novel Tetravalent and Bispecific IgG-Like Antibody Molecules Combining Single-Chain Diabodies With the Immunoglobin Gamma 1 Fc or CH3 Region,"FEBS Letters 454: 90-94, 1999.
Altman et al., "Phenotypic Analysis of Antigen-Specific T Lymphocytes", Science 274:94-96, 1996.
Angal et al., "A single amino acid substitution abolishes the heterogeneity of chimeric mouse/human (IgG4) antibody," Mol Immunol 30 :105-108, 1993.
Armour et al., "The contrasting IgG-binding interactions of human and herpes simplex virus Fc receptors," Biochemical Society Transactions 30:495-500, 2002.
Armour et al., "Recombinant human IgG molecules lacking Fcgamma receptor I binding and monocyte triggering activities," Eur J Immunol 29:2613-2624, 1999.
Armour et al., "Differential binding to human FcgammaRIIa and FcgammaRIIb receptors by human IgG wildtype and mutant antibodies," Mol Immunol 40 :585-593, 2003.
Armstrong, S. et al. "Heterogeneity of IgG1 monoclonal anti-Rh(D): an investigation using ADCC and macrophage binding assays," Brit. J. Haematol. 66:257-262 (1987).
Baggiolini M, Dewald B. "Cellular models for the detection and evaluation of drugs that modulate human phagocyte activity," Experientia. Oct. 15;44(10):841-848, 1988.
Boder and Wittrup, 1997, "Yeast surface display for screening combinatorial polypeptide libraries", Nature Biotechnology 15:553-557.
Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder et al., "Directed evolution of antibody fragments with monovalent femtomolar antigen-binding affinity," Proc. Natl. Acad. Sci. USA 97:10701-10705, 2000.
Boruchov et al., "Expression and Modulation of the Inhibitory Fcγ Receptor, FcγRIIB (CD32B), on Human Dendritic Cells (DCs)," Blood 102(11):Abstract #1908, 2003.
Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.

Brown EJ., vol. 45 (Microbes as Tools for Cell Biology) in *Methods in Cell Biololgy*, Russell ed. Academic Press Inc. pp. 147-64, 1994.
Burlmeister et al., "Crystal structure of the complex of rat neonatal Fc receptor with Fc," Nature 372:379-383, 1994.
Burton and Woof, "Human antibody effector function," Advances in Immunology 51:1-84, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Canfield and Morrison, "The binding affinity of human IgG for its high affinity Fc receptor is determined by multiple amino acids in the CH2 domain and is modulated by the hinge region," J Exp Med 173:1483-1491, 1991.
Caron et al., "Engineered humanized dimeric forms of IgG are more effective antibodies," J Exp Med 176 :1191-5, 1992.
Carter et al., "Humanization of an anti-p185HER2 antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99 :754-758, 2002.
Chappel et al., "Identification of the Fc gamma receptor class I binding site in human IgG through the use of recombinant IgG1/IgG2 hybrid and point-mutated antibodies," Proc. Natl. Acad. Sci USA 88:9036-9040, 1991.
Chappel et al., "Identification of a secondary Fc gamma RI binding site within a genetically engineered human IgG antibody," J Biol. Chem 268:25124-25131, 1993.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies trigger inflammation through Fc receptors," Immunity 3:21-26, 1995.
Clynes et al., "Modulation of immune complex-induced inflammation in vivo by the coordinate expression of activation and inhibitory Fc receptors," J Exp Med 189:179-185, 1999.
Clynes et al , "Inhibitory Fc receptors modulate in vivo cytoxicity against tumor targets," Nature Medicine 6 :443-446, 2000.
Clynes et al., "Fc receptors are required in passive and active immunity to melanoma," Proc. Natl. Acad. Sci USA 95:652-656, 1998.
Clynes et al., "Uncoupling of immune complex formation and kidney damage in autoimmune glomerulonephritis," Science 279:1052-1054, 1998.
de Haas, Wien Kin "IgG-Fc receptors and the clinical relevance of their polymorphisms," Wien Klin Wochenscha 113:825-831, 2001.
Deisenhofer, "Crystallographic refinement and atomic models of a human Fc fragment and its complex with fragment B of protein A from *Staphylococcus aureus* at 2.9- and 2.8-A resolution," Biochem. 20:2361-2370, 1981.
Deo et al., "Clinical significance of IgG Fc receptors and Fc gamma R-directed immunotherapies," Immunology Today 18:127-135, 1997.
Duncan and Winter, "The binding site for C1q on IgG," Nature 332 :738-740, 1988.
Duncan and Winter, "Localization of the binding site for the human high-affinity Fc receptor on IgG," Nature 332:563-564, 1988.
Edberg et al., "Modulation of Fcgamma and Complement Receptor Function by the Glycosyl-Phosphatidylinositol-Anchored Form of FcgammaRIII," Journal of Immunology 152: 5826-5835, 1994.
Flesch and Neppert, "Functions of the Fc receptors for immunoglobulin G," J Clin Lab Anal 14:141-156, 2000.
Gergeley et al., "Fc receptors on lymphocytes and K cells," Biochemical Society Transactions 12:739-743, 1984.
Gergely and Sarmay, "The two binding-site models of human IgG binding Fc gamma receptors," FASEB J 4:3275-3283, 1990.
Greenwood and Clark, Effector functions of matched sets of recombinant human IgG subclass antibodies. (final version edited Feb. 11, 1993).
Greenwood et al., "Structural motifs involved in human IgG antibody effector functions," Eur J Immunol 23:1098-1104, 1993.
Greenwood et al., "Engineering multiple-domain forms of the therapeutic antibody CAMPATH-1H: effects on complement lysis," Therapeutic Immunology 1:247-255, 1994.

(56) References Cited

OTHER PUBLICATIONS

Hadley et al., "The functional activity of Fc gamma RII and Fc gamma RIII on subsets of human lymphocytes," Immunology 76:446-451, 1992.
Hatta et al., "Association of Fc gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.
Hogarth et al., "Characterization of FcR Ig-binding sites and epitope mapping," Immunomethods 4 :17-24, 1994.
Holler et al., "In vitro evolution of a T cell receptor with high affinity for peptide/MHC," Proc. Natl. Acad. Sci. U.S.A. 97 :5387-92, 2000.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Hulett et al., "Chimeric Fc receptors identify functional domains of the murine high affinity receptor for IgG," J Immunol 147 :1863-1868, 1991.
Idusogie et al., "Mapping of the C1q binding site on rituxan, a chimeric antibody with a human IgG1 Fc," J Immunol 164: 4178-4184, 2000.
Idusogie et al., "Engineered antibodies with increased activity to recruit complement," J Immunol 166 :2571-2575, 2001.
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.
Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jassal et al., "Remodeling glycans on IgG by genetic re-engineering," Biochem Soc Trans 26 :S113, 1998.
Jefferis and Lund, "Interaction sites on human IgG-Fc for FcgammaR: current models," Immunology Letters 82 :57-65, 2002.
Jefferis et al., "Recognition sites on human IgG for Fc gamma receptors: the role of glycosylation," Immunol Lett 44 :111-7, 1995.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jendeberg et al., "Engineering of Fc(1) and Fc(3) from human immunoglobulin G to analyse subclass specificity for staphylococcal protein A," J Immunological Methods 201 :25-34, 1997.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kadar et al., "Modulatory effect of synthetic human IgG Fc peptides on the in vitro immune response of murine spleen cells," Int J Immunpharmacol 13 :1147-55, 1991.
Kato et al., "Structural basis of the interaction between IgG and Fcγ receptors," J Mol Biol 295:213-224, 2000.

Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.
Kieke et al., "Selection of functional T cell receptor mutants from a yeast surface-display library," Proc. Natl. Acad. Sci. U.S.A. 96 :5651-56, 1999.
Kim et al., "Analysis of FcγRIII and IgG Fc polymorphism reveals functional and evolutionary implications of protein-protein interaction," J Mol Evol 53:1-9, 2001.
Klein et al., "Expression of biological effector functions by immunoglobulin G molecules lacking the hinge region," Proc. Natl. Acad. Sci. U.S.A. 78 :524-528, 1981.
Koene et al., "Fc gammaRIIIa-158V/F polymorphism influences the binding of IgG by natural killer cell Fc gammaRIIIa, independently of the Fc gammaRIIIa-48L/R/H phenotype," Blood 90 :1109-1114, 1997.
Kranz et al., "Mechanisms of ligand binding by monoclonal anti-fluorescyl antibodies," J. Biol. Chem. 257:6987-6995, 1982.
Kumpel, B.M. Brit. "Human monoclonal anti-D antibodies," J. Haematol. 71:415-420 (1989).
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Li et al., "Reconstitution of human Fc gamma RIII cell type specificity in transgenic mice," J Exp Med 183 :1259-1263, 1996.
Liu et al., "Production of a mouse-human chimeric monoclonal antibody to CD20 with potent Fc-dependent biologic activity," J. Immunol. 139:3521-3526, 1987.
Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.
Lund et al., "Oligosaccharide-protein interactions in IgG can modulate recognition by Fc gamma receptors," FASEB J 9 :115-119, 1995.
Lund et al., "Human Fc gamma RI and Fc gamma RII interact with distinct but overlapping sites on human IgG," J Immunol 147 :2657-62, 1991.
Lund et al., "Multiple interactions of IgG with its core oligosaccharide can modulate recognition by complement and human Fc gamma receptor I and influence the synthesis of its oligosaccharide chains," J Immunol 157 :4963-4969, 1996.
Lund et al., "Multiple binding sites on the CH2 domain of IgG for mouse Fc gamma R11," Molecular Immunology 29:53-59, 1992.
Maenaka et al., "The human low affinity Fcgamma receptors IIa, IIb, and III bind IgG with fast kinetics and distinct thermodynamic properties," J Biol Chem 48 :44898-904, 2001.
Michaelsen et al., "One disulfide bond in front of the second heavy chain constant region is necessary and sufficient for effector functions of human IgG3 without a genetic hinge," Immunolgy 91 :9243-9247, 1994.
Morgan et al., "The N-terminal end of the CH2 domain of chimeric human IgG1 anti-HLA-DR is necessary for C1q, Fc gamma RI and Fc gamma RIII binding," Immunology 86 :319-324, 1995.
Morrison et al., "Structural determinants of IgG structure," Immunologist 2 :119-124, 1994.
Munn et al., "Phagocytosis of tumor cells by human monocytes cultured in recombinant macrophage colony-stimulating factor," J Exp Med. 172(1):231-7, 1990.
Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.
Neuberger et al., "Recombinant antibodies possessing novel effector functions," Nature 312 :604-608, 1984.
Norderhaug et al., "Chimeric mouse human IgG3 antibodies with an IgG4-like hinge region induce complement-mediated lysis more efficiently than IgG3 with normal hinge," Eur J Immunol 21:2379-84, 1991.

(56) References Cited

OTHER PUBLICATIONS

Nose and Leanderson, "Substitution of asparagine324 with aspartic acid in the Fc portion of mouse antibodies reduces their capacity for C1q binding," Eur J Immunol 19 :2179-81, 1989.
Okazaki et al., "Fucose depletion from human IgG1 oligosaccharide enhances binding enthalpy and association rate between IgG1 and FcgammaRIIIa," J Mol Biol 336 :1239-1249, 2004.
Orfao and Ruiz-Arguelles, "General concepts about cell sorting techniques," Clinical Biochem. 29:5-9, 1996.
Partridge et al., "The use of anti-IgG monoclonal antibodies in mapping the monocyte receptor site on IgG," Mol Immunol. 23(12):1365-72, 1986.
Perussia "Human Natural Killer Cell Protocols" in *Methods Molecular Biology*. vol. 121 (Campbell et al. eds.) Humana Press Inc., Totowa, NJ. 179-92, 2000.
Radaev and Sun, "Recognition of immunoglobulins by Fcgamma receptors," Molecular Immunology 38 :1073-1083, 2001.
Ravetch and Bolland, "IgG Fc receptors," Annu Rev Immunol 19:275-90, 2001.
Ravetch and Clynes, "Divergent roles for Fc receptors and complement in vivo," Annu Rev Immunol 16:421-432, 1998.
Ravetch and Kinet, "Fc receptors," Annu Rev Immunol 9:457-492, 1991.
Ravetch and Lanier, "Immune inhibitory receptors," Science 290:84-89, 2000.
Redpath et al., "The influence of the hinge region length in binding of human IgG to human Fcgamma receptors," Hum Immunol 59 :720-727, 1998.
Reff et al., "Depletion of B cells in vivo by a chimeric mouse human monoclonal antibody to CD20," Blood 83:435-445, 1994.
Reff et al., "A review of modifications to recombinant antibodies: attempt to increase efficacy in oncology applications," Critical Reviews in Oncology/Hematology 40: 25-35; 2001.
Riechmann et al., "Reshaping human antibodies for therapy," Nature. 332(6162):323-7, 1988.
Sarmay et al., "The effect of synthetic peptides corresponding to Fc sequences in human IgG1 on various steps in the B cell activation pathway," Eur J Immunol 18 :289-294, 1988.
Sarmay et al., "Ligand inhibition studies on the role of Fc receptors in antibody-dependent cell-mediated cytotoxicity," Mol Immunol 21 :43-51, 1984.
Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.
Sautes-Fridman et al., "Fc gamma receptors: a magic link with the outside world," ASHI Quarterley, 4th Quarter:148-151, 2003.
Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).
Schatz et al., "Use of peptide libraries to map the substrate specificity of a peptide-modifying enzyme: a 13 residue consensus peptide specifies biotinylation in *Escherichia coli*," Bio/Technology 11:1138-1143, 2000.
Sensel et al., "Amino acid differences in the N-terminus of C(H)2 influence the relative abilities of IgG2 and IgG3 to activate complement," Molecular Immunology 34:1019-1029, 1997.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Yeast polypeptide fusion surface display levels predict thermal stability and soluble secretion efficiency," J Mol Biol 292:949-956, 1999.
Shusta et al., "Increasing the secretory capacity of *Saccharomyces cerevisiae* for production of single-chain antibody fragments," Nature Biotechnology 16:773-777, 1998.
Shusta et al., "Directed evolution of a stable scaffold for T-cell receptor engineering," Nature Biotechnology 18:754-759, 2000.
Smith and Morrison, "Recombinant polymeric IgG: an approach to engineering more potent antibodies," Bio/Technology 12:683-688, 1994.
Sondermann and Oosthuizen, "The structure of Fc receptor/Ig complexes: considerations on stoichiometry and potential inhibitors," Immunology Letters, 82:51-56, 2002.
Sondermann et al., "Molecular basis for immune complex recognition: a comparison of Fc-receptor structures," J. Mol. Biol. 309:737-749, 2001.
Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "The 3.2-A crystal structure of the human IgG1 Fc fragment-Fc gammaRIII complex," Nature 406:267-273, 2000.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Strohmeier et al., "Role of the Fc gamma R subclasses Fc gamma RII and Fc gamma RIII in the activation of human neutrophils by low and high valency immune complexes," J Leukocyte Biol 58:415-422, 1995.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "FcR gamma chain deletion results in pleiotrophic effector cell defects," Cell 76 :519-529, 1994.
Takai et al., "Augmented humoral and anaphylactic responses in Fc gamma RII-deficient mice," Nature 379:346-349, 1996.
Takai, "Roles of Fc receptors in autoimmunity," Nature Reviews 2:580-592, 2002.
Tamm et al., "The IgG binding site of human FcγRIIIB receptor involves CC' and FG loops of the membrane-proximal domain," J Biol Chem 271:3659-3666, 1996.
Tao et al., "The differential ability of human IgG1 and IgG4 to activate complement is determined by the COOH-terminal sequence of the CH2 domain," J Exp Med 173:1025-1028, 1991.
Tao et al., "Structural features of human immunoglobulin G that determine isotype-specific differences in complement activation," J Exp Med 178:661-667, 1993.
Tridandapandi et al., "Regulated Expression and Inhibitory Function of FcgammaRIIB in Human Monocytic Cells," Journal of Biological Chemistry 277(7): 5082-5089, 2002.
Van Sorge et al., "FcgammaR polymorphisms: Implications for function, disease susceptibility and immunotherapy," Tissue Antigens 61:189-202, 2003.
VanAntwerp and Wittrup, "Fine affinity discrimination by yeast surface display and flow cytometry," Biotechnol Prog 16:31-37, 2000.
Vidarte, "Serine 132 is the C3 covalent attachment point on the CH1 domain of human IgG1," J Biol Chem 276:38217-38233, 2001.
Ward and Ghetie, "The effector functions of immunoglobulins: implications for therapy," Therapeutic Immunology 2:77-94, 1995.
Weng and Levy, "Two immunoglobulin G fragment C receptor polymorphisms independently predict response to rituximab in patients with follicular lymphoma," J Clin Oncol 21:3940-3947, 2003.
Wiener, E. et al. "Differences between the activities of human monoclonal IgG1 and IgG3 anti-D antibodies of the Rh blood group system in their abilities to mediate effector functions of monocytes," Immunol. 65:159-163 (1988).
Wing et al., "Mechanism of first-dose cytokine-release syndrome by CAMPATH 1-H: Involvement of CD16 (FcγRIII) and CD11a/CD18 (LFA-1) on NK cells," J Clin Invest 98 :2819-2826, 1996.

(56) References Cited

OTHER PUBLICATIONS

Wingren et al., "Comparison of surface properties of human IgA, IgE, IgG and IgM antibodies with identical and different specificities," Scand J Immunol 44:430-436, 1996.
Wittrup, "The single cell as a microplate well," Nat Biotechnol 18:1039-1040, 2000.
Witttrup, "Protein engineering by cell-surface display," Curr, Opin. Biotechnol. 12:395-399, 2001.
Woof et al., "Localisation of the monocyte-binding region on human immunoglobulin G," Mol Immunol 23 :319-330, 1986.
Wu et al., "A novel polymorphism of FcγRIIIa (CD16) alters receptor function and predisposes to autoimmune disease," J Clin Invst 100 :1059-1070, 1997.
Xu et al., "Residue at position 331 in the IgG1 and IgG4 CH2 domains contributes to their differential ability to bind and activate complement," J Biol Chem 269 :3469-3474, 1994.
Yeung and Wittrup, "Quantitative screening of yeast surface-displayed polypeptide libraries by magnetic bead capture," Biotechnol Prog 18:212-220, 2002.
Zeidler et al., "The Fc-region of a new class of intact bispecific antibody mediates activation of accessory cells and NK cells and induces direct phagocytosis of tumour cells," British J Cancer 83:261-266, 2000.
Zuckier et al., "Chimeric human-mouse IgG antibodies with shuffled constant region exons demonstrate that multiple domains contribute to in vivo half-life," Cancer Res 58 :3905-3908, 1998.
Abrahams, B.C. et al. (2004) "Anticipating Smallpox and Monkeypox Outbreaks: Complications of the Smallpox Vaccine," Neurologist 10(5):265-274.
Anderson, S.G. et al. (1970) "The International Standard for Anti-Smallpox Serum," Bull. World Health Organ. 42 (4):515-523.
Anonymous; Centers for Disease Control and Prevention (2003) "Update: Cardiac-Related Events During the Civilian Smallpox Vaccination Program—United States, 2003," Morbidity Mortality Weekly Rep. 52:492-496.
Appleyard, G. et al. (1974) "Neutralizing Activities of Antisera to Poxvirus Soluble Antigens," J. Gen. Virol. 23 (2):197-200.
Artenstein, A.W. et al. (2005) "A Novel, Cell Culture-Derived Smallpox Vaccine in Vaccinia-Naive Adults," Vaccine 23 (25):3301-3309.
Asano, R. et al. (Epub Jul. 19, 2007) "Highly Effective Recombinant Format of a Humanized Igg-Like Bispecific Antibody for Cancer Immunotherapy With Retargeting of Lymphocytes to Tumor Cells," J. Biol. Chem. 282 (38):27659-27665.
Barbas, C.F. III, et al. (1991) "Assembly of combinatorial antibody libraries on phage surfaces: the gene III site," Proc. Natl. Acad. Sci. (U.S.A.) 88(18):7978-7982.
Bolken, T.C. et al. (Epub Aug. 15, 2007) "Discovery and Development of Antiviral Drugs for Biodefense: Experience of a Small Biotechnology Company," Antiviral Res. 77(1):1-5.
Bray, M. et al. (2003) "Progressive Vaccinia," Clin. Infect. Dis. 36(6):766-774.
Buller, R.M. et al. (1991) "Poxvirus Pathogenesis," Microbiol. Rev. 55(1):80-122.
Buller, R.M. et al. (2004) "Efficacy of Oral Active Ether Lipid Analogs of Cidofovir in a Lethal Mousepox Model," Virology 318(2):474-481.
Casadevall, A. et al. (2004) "Passive Antibody Therapy for Infectious Diseases," Nat. Rev. Microbiol. 2(9):695-703.
Chaudhri, G. et al. (2006) "Obligatory Requirement for Antibody in Recovery From a Primary Poxvirus Infection," J. Virol. 80(13):6339-6344.
Chen, Z. et al. (2006) "Chimpanzee/Human Mabs to Vaccinia Virus B5 Protein Neutralize Vaccinia and Smallpox Viruses and Protect Mice Against Vaccinia Virus," Proc. Natl. Acad. Sci. (U.S.A.) 103(6):1882-1887.
Chen, Z. et al. (Jun. 20, 2007) "Characterization of Chimpanzee/Human Monoclonal Antibodies to Vaccinia Virus A33 Glycoprotein and Its Variola Virus Homolog in Vitro and in a Vaccinia Virus Mouse Protection Model," J. Virol. 81 (17):8989-8995.

Cho, C.T. et al. (1973) "Monkeypox Virus," Bacteriol. Rev. 37(1):1-18.
Dall'Acqua, W.F. et al. (2002) "Increasing the Affinity of a Human IgG1 for the Neonatal Fc Receptor: Biological Consequences," J. Immunol. Nov. 1, 2002;169(9):5171-80.
De Clercq, E. et al. (2008) "Emerging Antiviral Drugs," Expert. Opin. Emerg. Drugs 13(3):393-416.
Di Giulio, D.B. et al. (2004) "Human Monkeypox: An Emerging Zoonosis," Lancet Infect. Dis. 4(1):15-25 (Erratum; Lancet Infect. Dis. (2004) 4(4):251).
Downie, A.W. et al. (1958) "The Antibody Response in Man Following Infection With Viruses of the Pox Group. III. Antibody Response in Smallpox," J. Hyg. (Lond) 56(4):479-487.
Earl, P.L. et al. (2003) "Development and Use of a Vaccinia Virus Neutralization Assay Based on Flow Cytometric Detection of Green Fluorescent Protein," J. Virol. 77(19):10684-10688.
Edghill-Smith, Y. et al. (2005) "Smallpox Vaccine Does Not Protect Macaques With AIDS From a Lethal Monkeypox Virus Challenge," J. Infect. Dis. 191(3):372-381.
Edghill-Smith, Y. et al. (2005) "Smallpox Vaccine-Induced Antibodies Are Necessary and Sufficient for Protection Against Monkeypox Virus," Nat. Med. 11(7):740-747.
Esteban, D.J. et al. (2005) "Ectromelia Virus: The Causative Agent of Mousepox," J. Gen. Virol. 86(10):2645-2659.
Fogg, C. et al. (2004) "Protective Immunity to Vaccinia Virus Induced by Vaccination With Multiple Recombinant Outer Membrane Proteins of Intracellular and Extracellular Virions," J. Virol. 78(19):10230-10237.
Fulginiti, V.A. et al. (2003) "Smallpox Vaccination: A Review, Part II. Adverse Events," Clin. Infect. Dis. 37(2):251-271.
Garcia, A.D. et al. (Epub Jun. 27, 2007) "Characterization and use of mammalian-expressed vaccinia virus extracellular membrane proteins for quantification of the humoral immune response to smallpox vaccines," Clin. Vaccine Immunol. 14(8):1032-1044.
Geddes, A.M. (2006) "The History of Smallpox," Clin. Dermatol. 24(3):152-157.
Hammarlund, E. et al. (2003) "Duration of Antiviral Immunity After Smallpox Vaccination," Nat. Med. 9(9):1131-1137.
Hanna, W. et al. (2002) "Studies in Smallpox and Vaccination 1913," Rev. Med. Virol. 12(4):201-209.
Heeney, J.L. (2006) "Zoonotic Viral Diseases and the Frontier of Early Diagnosis, Control and Prevention," J. Intern. Med. 260(5):399-408.
Henderson, D.A. (1998) "Bioterrorism As a Public Health Threat," Emerg. Infect. Dis. Jul.-Sep. 1998;4(3):488-492.
Henderson, D.A. et al. (1999) "Smallpox As a Biological Weapon: Medical and Public Health Management. Working Group on Civilian Biodefense," J. Amer. Med. Assn. 281(22):2127-2137.
Heymann, D.L. et al. (1998) "Re-Emergence of Monkeypox in Africa: A Review of the Past Six Years," Brit. Med. Bull. 54(3):693-702.
Hooper, J.W. et al. (2000) "DNA Vaccination With Vaccinia Virus L1R and A33R Genes Protects Mice Against a Lethal Poxvirus Challenge," Virology 266(2):329-339.
Hooper, J.W. et al. (2003) "Four-Gene-Combination DNA Vaccine Protects Mice Against a Lethal Vaccinia Virus Challenge and Elicits Appropriate Antibody Responses in Nonhuman Primates," Virology 306(1):181-195.
Hooper, J.W. et al. (2004) "Smallpox DNA Vaccine Protects Nonhuman Primates Against Lethal Monkeypox," J. Virol. 78(9):4433-4443.
Hopkins, R.J. et al. (2004) "Safety and Pharmacokinetic Evaluation of Intravenous Vaccinia Immune Globulin in Healthy Volunteers," Clin. Infect. Dis. 39(6):759-766.
Kretzschmar, M. et al. (2004) "Ring Vaccination and Smallpox Control," Emerg. Infect. Dis. 10(5):832-841.
Kretzschmar, M. et al. (2006) "Frequency of Adverse Events after Vaccination with Different Vaccinia Strains," PLoS Medicine 3(8):e272 doi:10.1371/ journal.pmed.0030272.
Law, M. et al. (2001) "Antibody Neutralization of the Extracellular Enveloped Form of Vaccinia Virus," Virology 280 (1):132-142.

(56) References Cited

OTHER PUBLICATIONS

Law, M. et al. (2005) "An Investigation of the Therapeutic Value of Vaccinia-Immune IgG in a Mouse Pneumonia Model," J. Gen. Virol. 86(Pt 4):991-1000.
Lawrence, S.J. et al. (2007) "Antibody Responses to Vaccinia Membrane Proteins After Smallpox Vaccination," J. Infect. Dis. 196(2):220-229.
Ligon, B.L. (2004) "Monkeypox: a review of the history and emergence in the Western hemisphere," Semin. Pediatr. Infect. Dis. 15(4)280-287.
Lustig, S. et al. (2004) "Synergistic Neutralizing Activities of Antibodies to Outer Membrane Proteins of the Two Infectious Forms of Vaccinia Virus in the Presence of Complement," Virology 328(1):30-35.
Mack, T.M. et al. (1972) "A Prospective Study of Serum Antibody and Protection Against Smallpox," Amer. J. Trop. Med. Hyg. 21(2):214-218.
Marvin, J.S. et al. (2005) "Recombinant Approaches to IgG-like Bispecific Antibodies," Acta Pharmacol. Sin. 26(6):649-658.
McClain, D.J. (1997) "Smallpox," In: Textbook of Military Medicine (Zatjchuk R, ed.); Washington, DC: Office of the Surgeon General, Walter Reed Medical Center; pp. 539-559).
Nalca, A. et al. (2005) "Reemergence of Monkeypox: Prevalence, Diagnostics, and Countermeasures," Clin. Infect. Dis. 41(12):1765-1771.
Parker, S. (Epub Sep. 4, 2007) "Efficacy of Therapeutic Intervention With an Oral Ether-Lipid Analogue of Cidofovir (CMX001) in a Lethal Mousepox Model," Antiviral Res. 77(1):39-49.
Prichard, M.N. et al. (2005) "Orthopoxvirus Targets for the Development of Antiviral Therapies," Curr. Drug Targets Infect. Disord. 5(1):17-28.
Quenelle, D.C. et al. (Epub Aug. 27, 2007) "Synergistic Efficacy of the Combination of ST-246 With CMX001 Against Orthopoxviruses," Antimicrob Agents Chemother. 51(11):4118-4124.
Robbins, S.J. et al. (2005) "The Efficacy of Cidofovir Treatment of Mice Infected With Ectromelia (Mousepox) Virus Encoding Interleukin-4," Antiviral Res. 66(1):1-7.
Sale, T.A. et al. (2006) "Monkeypox: An Epidemiologic and Clinical Comparison of African and US Disease," J. Am. Acad. Dermatol. 55(3):478-481.
Sarkar, J.K. et al. (1978) "The Minimum Protective Level of Antibodies in Smallpox," Bull. Who. 52:307-311.
Schmaljohn, C. (1999) "Production and Characterization of Human Monoclonal Antibody Fab Fragments to Vaccinia Virus From a Phage-Display Combinatorial Library," Virology 258(1):189-200.
Schofield, D.J. et al. (2002) "Four Chimpanzee Monoclonal Antibodies Isolated by Phage Display Neutralize Hepatitis A Virus," Virology 292(1):127-136.
Shearer, J.D. et al. (2005) "Biological Activity of an Intravenous Preparation of Human Vaccinia Immune Globulin in Mouse Models of Vaccinia Virus Infection," Antimicrob. Agents Chemother. 49(7):2634-2641.
Stittelaar, K.J. et al. (2005) "Modified Vaccinia Virus Ankara Protects Macaques Against Respiratory Challenge With Monkeypox Virus," J. Virol. 79(12):7845-7851.
Su, H.P. et al. (2007) "Structural Basis for the Binding of the Neutralizing Antibody, 7D11, to the Poxvirus L1 Protein," Virology 368(2):331-341.
Thorne, C.D. et al. (2003) "Emergency Medicine Tools to Manage Smallpox (Vaccinia) Vaccination Complications: Clinical Practice Guideline and Policies and Procedures," Ann. Emerg. Med. 42(5):665-680.
Turner, G.S. et al. (1971) "Inactivated Smallpox Vaccine: Immunogenicity of Inactivated Intracellular and Extracellular Vaccinia Virus," J. Gen. Virol. 13(1):19-25).
Viner, K.M. et al. (2005) "Activity of Vaccinia Virus-Neutralizing Antibody in the Sera of Smallpox Vaccines," Microbes Infect 7(4):579-583.
Vollmar, J. et al. (2006; Epub Nov. 28, 2005) "Safety and Immunogenicity of IMVAMUNE, A Promising Candidate as a Third Generation Smallpox Vaccine," Vaccine 24(12):2065-2070.
Wittek, R. (2006) "Vaccinia Immune Globulin: Current Policies, Preparedness, and Product Safety and Efficacy," Int. J. Infect. Dis. 10(3):193-201.
Wolffe, E.J. et al. (1995) "A Myristylated Membrane Protein Encoded by The Vaccinia Virus L1R Open Reading Frame is the Target of Potent Neutralizing Monoclonal Antibodies," Virology 211(1):53-63.
Wu, C. et al. (Epub Oct. 14, 2007) "Simultaneous Targeting of Multiple Disease Mediators by a Dual-Variable-Domain Immunoglobulin," Nature Biotechnol. 25(11):1290-1297.
International Search Report, PCT/US08/87390 (Nov. 18, 2009); pp. 1-6.
Written Opinion, PCT/US08/87390 (Nov. 18, 2009); pp. 1-5.
Mertens, N. et al., "New Recombinant Bi- and Trispecific Antibody Derivatives," In: Novel Frontiers in the Production of Compounds for Biomedical Use, vol. 1; van Broekhoven, A. et al. (Eds.); Kluwer Academic Publishers, Dordrecht, The Netherlands.
Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.
Anonymous, "MacroGenics Enters Global Research Collaboration and License Agreement with Pfizer;" Press Release of MacroGenics, Inc.; Oct. 26, 2010; 2 pages.
Asano, R. et al. (2004) "*A Diabody for Cancer Immunotherapy and Its Functional Enhancement by Fusion of Human Fc Region*," Abstract 3P-683, J. Biochem. 76(8):992.
Mertens, N. et al., "*New Recombinant Bi- and Trispecific Antibody Derivatives*," In: Novel Frontiers in the Production of Compounds for Biomedical Use, A. VanBroekhoven et al. (Eds.), Kluwer Academic Publishers, Dordrecht, The Netherlands (2001), pp. 195-208.
Lu et al. (2005) "*A Fully Human Recombinant IgG-Like Bispecific Antibody to Both the Epidermal Growth Factor Receptor and the Insulin-Like Growth Factor Receptor for Enhanced Antitumor Activity*," J. Biol. Chem. 280(20):19665-19672.

\* cited by examiner

```
              ┌─────────────── FR1 ───────────────┐  ┌CDR1┐
    mVH       QVQLQQSGAELAKPGASVKMSCKASGYTFT         RYWMH
    hVH       ----V------VK--------V----------       -----
              └──────────────────────────────────┘  └────┘
                              VH1-18

┌───── FR2 ─────┐    ┌──────── CDR2 ────────┐
    mVH       WVKQRPGQGLEWIG        YINPSTGYTEYNQKFKD
    hVH       ----A-------M-        -----------------
              └───────────────┘
                    VH1-18

┌──────────────── FR3 ────────────────┐
    mVH       KATLTADKSSSTVYMQLSSLTSEDSAVYYCAR
    hVH       RV-I-----T--A--E-R--R-D-T-------
              └─────────────────────────────────────┘
                              VH1-69

┌── CDR3 ──┐    ┌─── FR4 ───┐
    mVH       TTVDGYDFAY      WGQGTLVTVSA
    hVH       ----------      ----------S
```

Figure 1

```
              ┌─────────── FR1 ───────────┐
    mVL       DMVMSQSPSSLAVSAGEKVSMSC
    hVL       -I--T---D-----L--RATIN-

┌────── CDR1 ──────┐   ┌────── FR2 ──────┐
    mVL       KSSQTLLNSRTRKNYLA     WYQQKPGQSPKLLIY
    hVL       -----------------     --------P------

┌─CDR2─┐   ┌─────────── FR3 ───────────┐
    mVL       WASTRES    GVPDRFTGSGSGTDFTLTISSVQAEDLAVYYC
    hVL       -------    ------S---------------L----V-----

┌─CDR3──┐  ┌── FR4 ──┐
    mVL       KQSYNLWT   FGGGTKLEIK
    hVL       --------   --Q-------
```

Prophylaxis and Treatment of ECTV-infected Mice

1: -virus vehicle -24h
2: +virus vehicle -24h
3: +virus mAb 1mg/kg -24h
4: +virus mAb 1mg/kg +24h
5: +virus mAb 10mg/kg -24h
6: +virus mAb 10mg/kg +24h
7: +virus mAb 100mg/kg -24h
8: +virus mAb 100mg/kg +24h
9: +virus CDV 100mg/kg -24h
10: +virus CDV 100mg/kg +24h

Figure 12

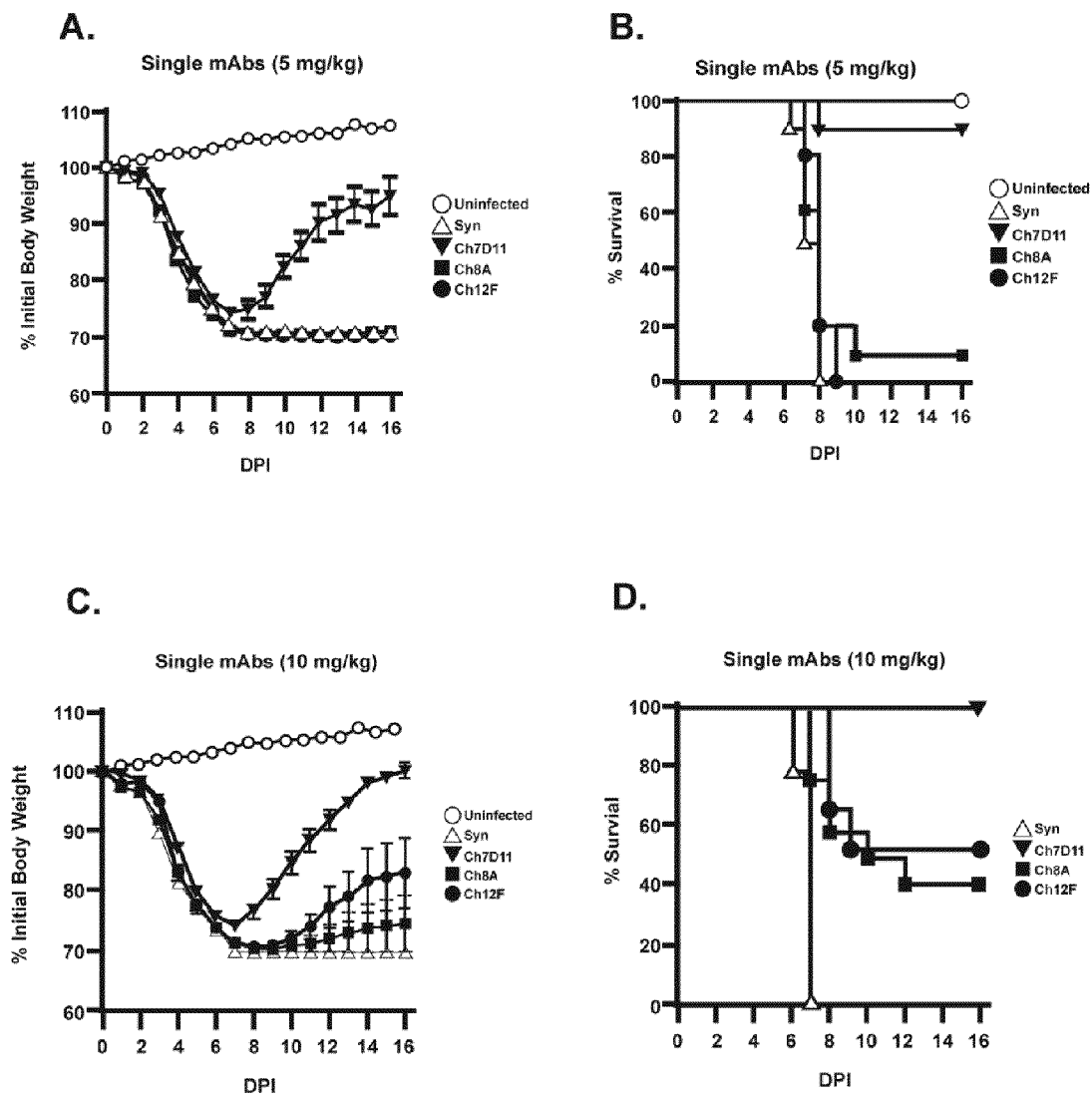
Figure 16 (A-D)

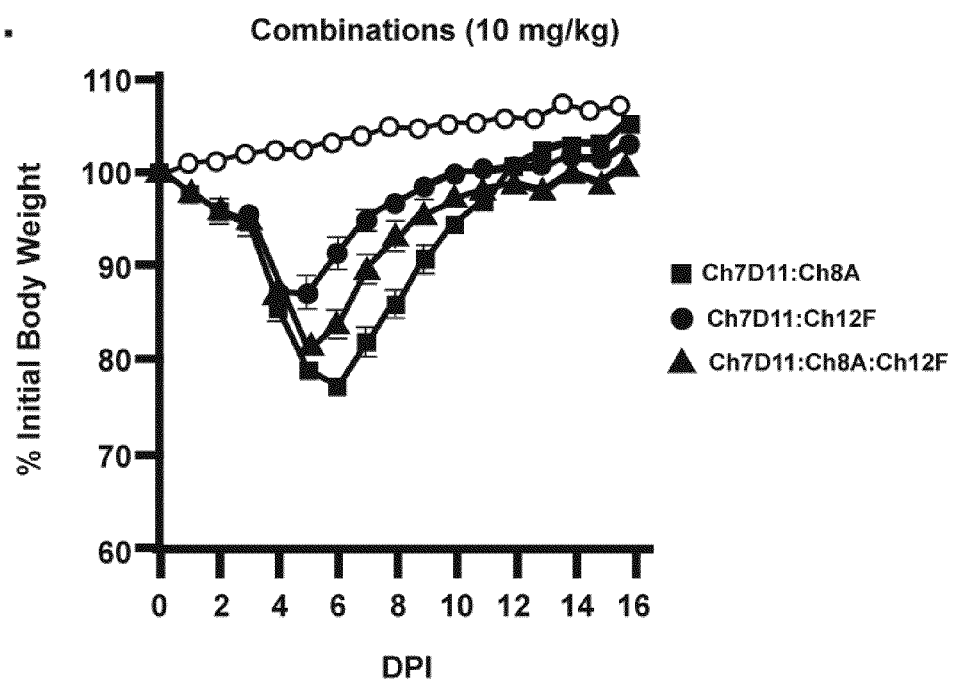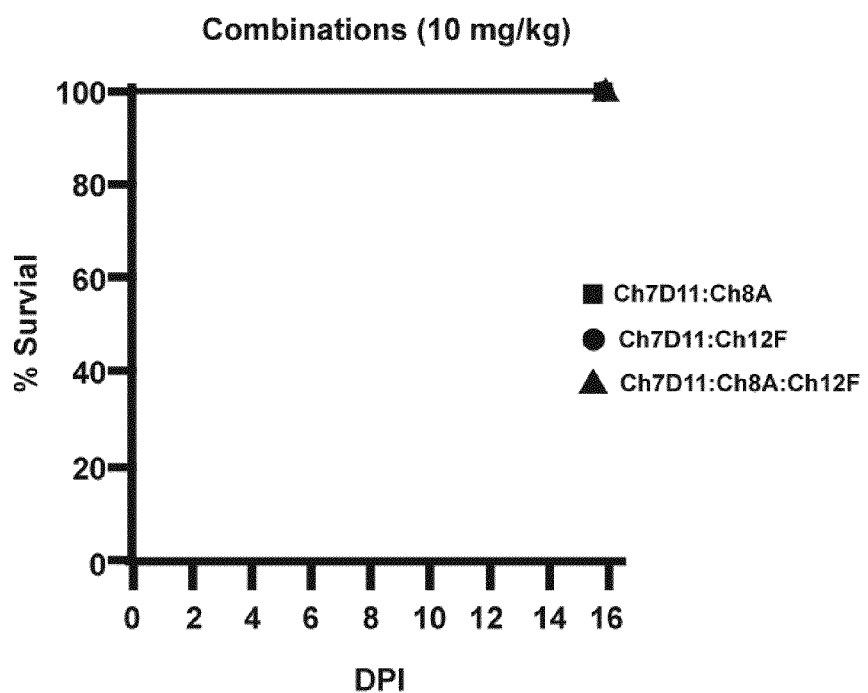
Figure 16 (E-F)

A.
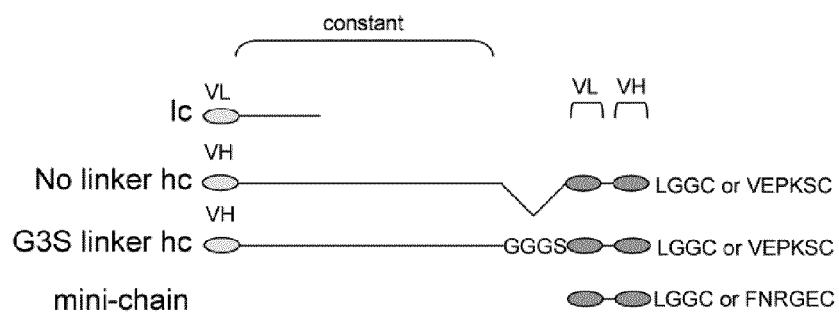
B.
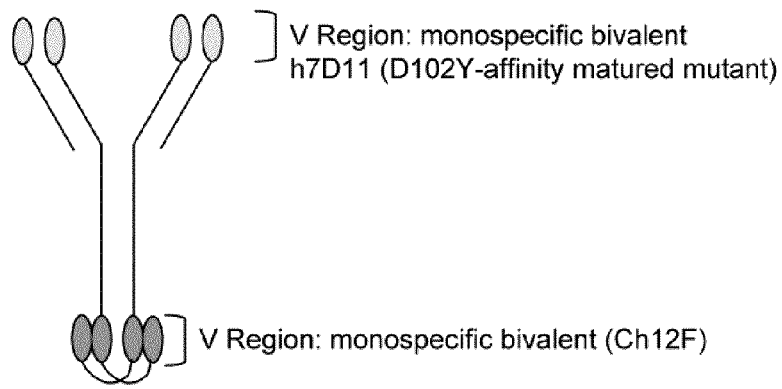
C.
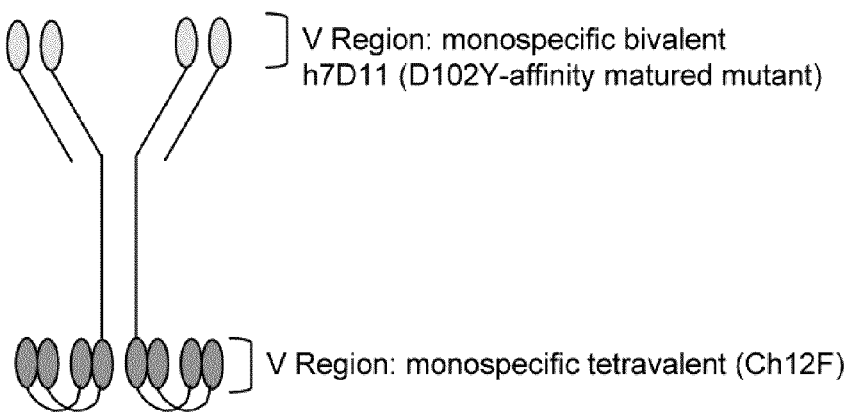
FIGURE 25

A.

B.

A.
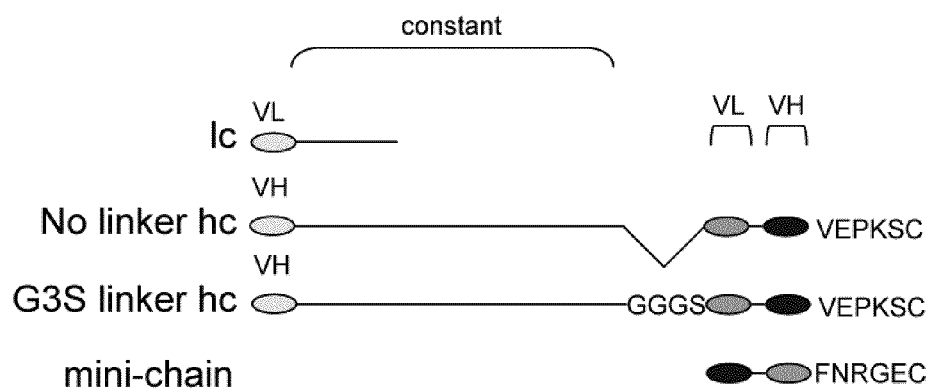
B.
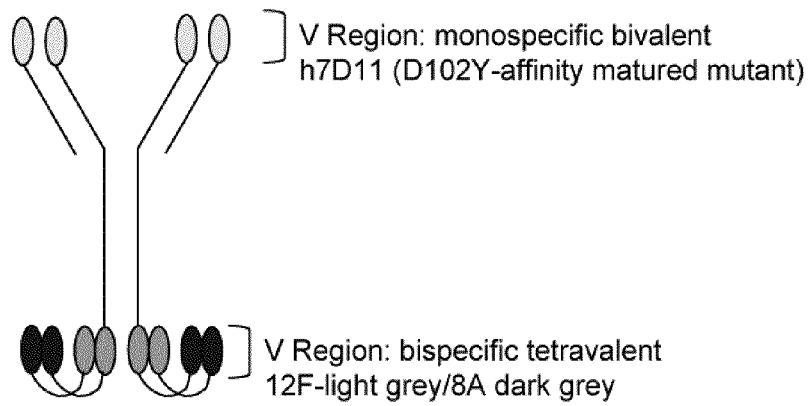
FIGURE 28

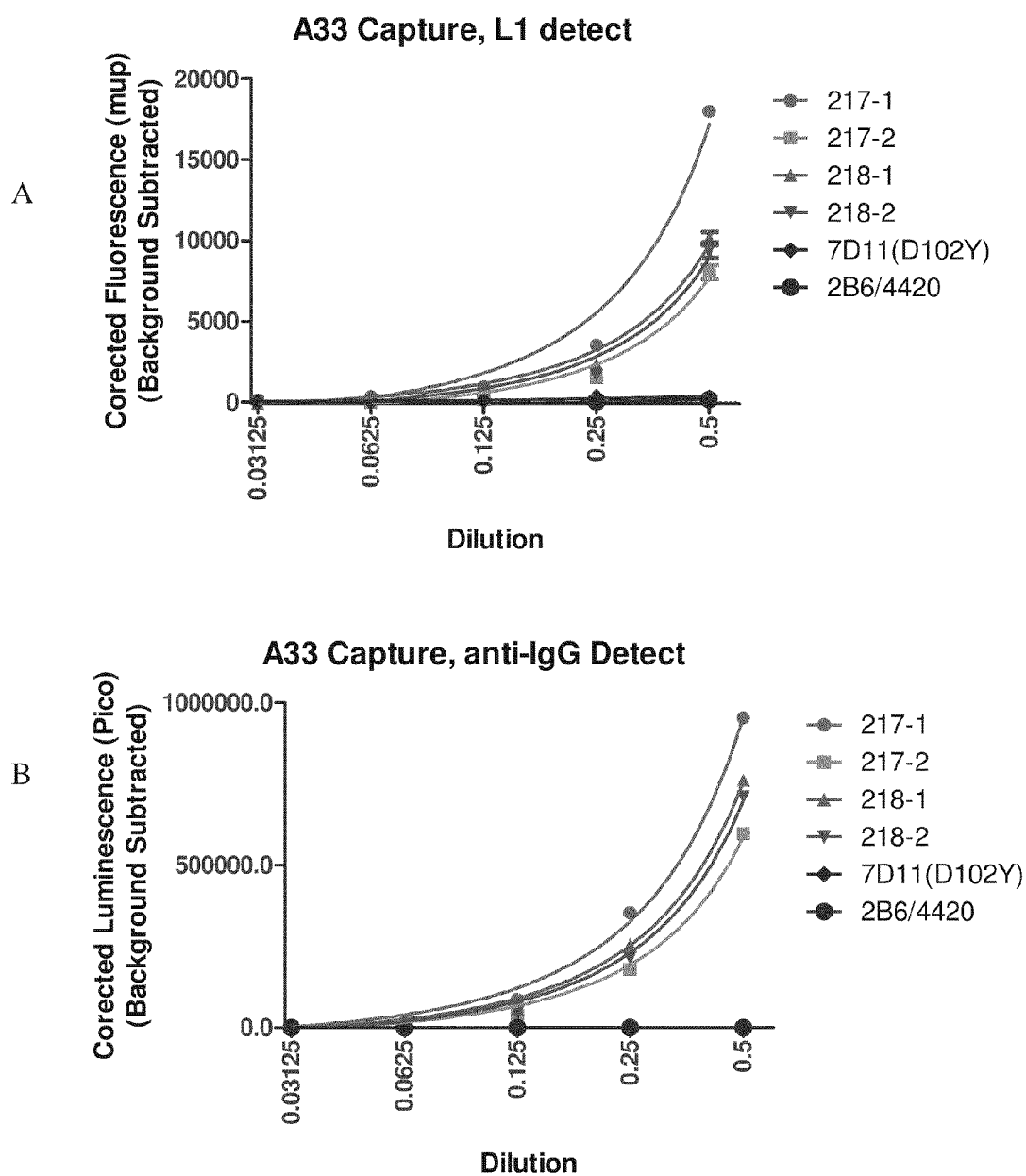
Figure 29(A-B)

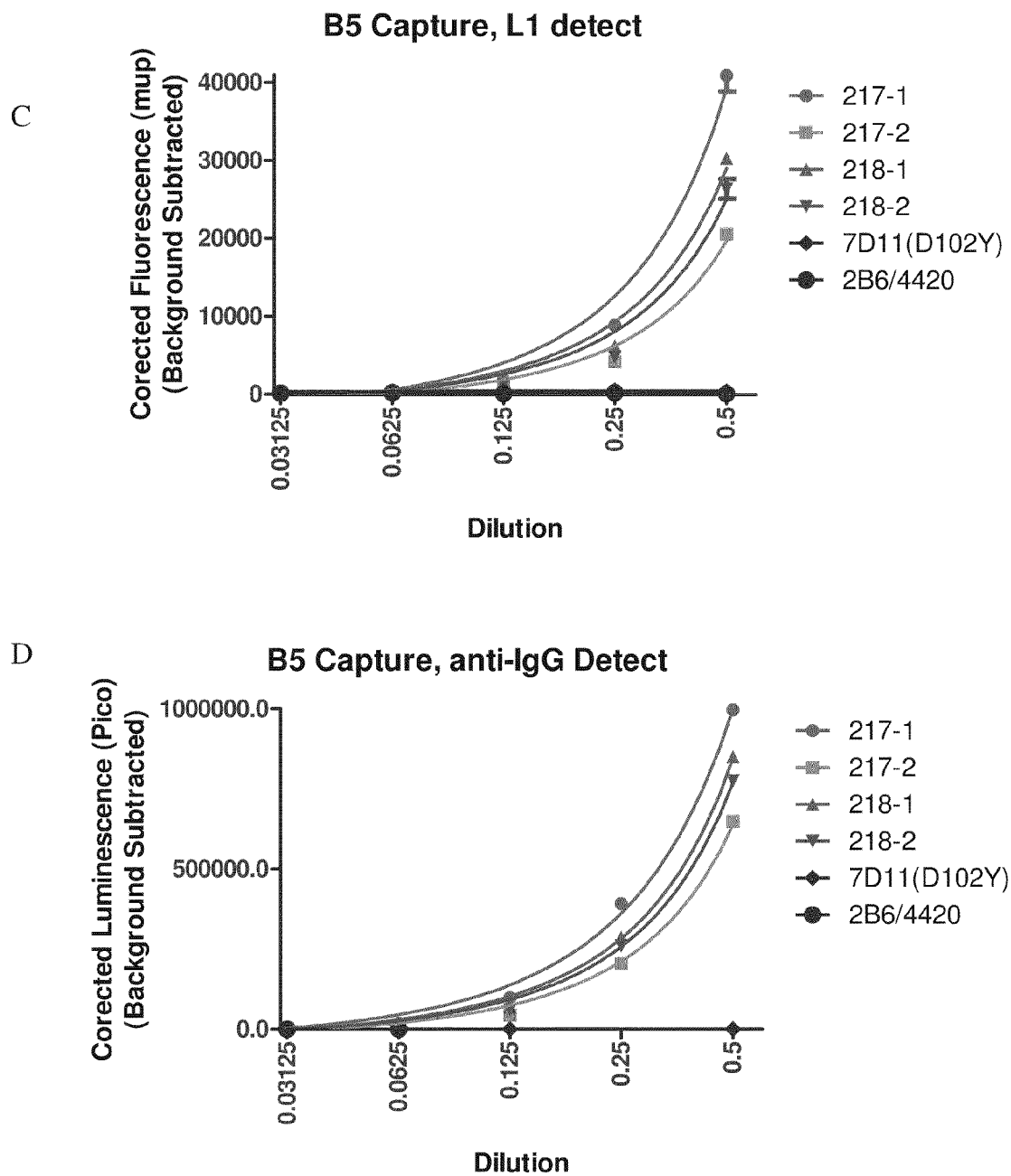
Figure 29(C-D)

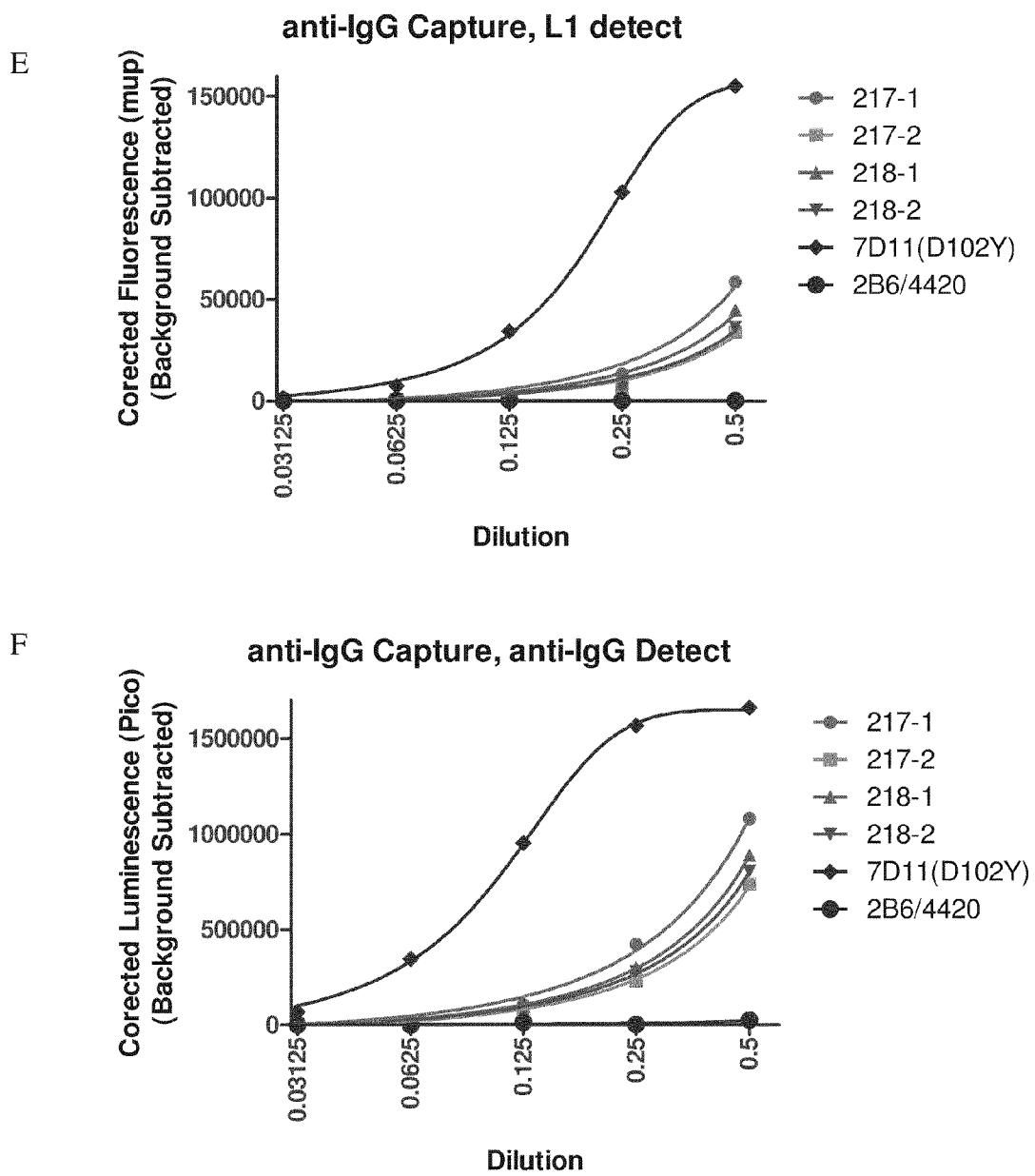
Figure 29(E-F)

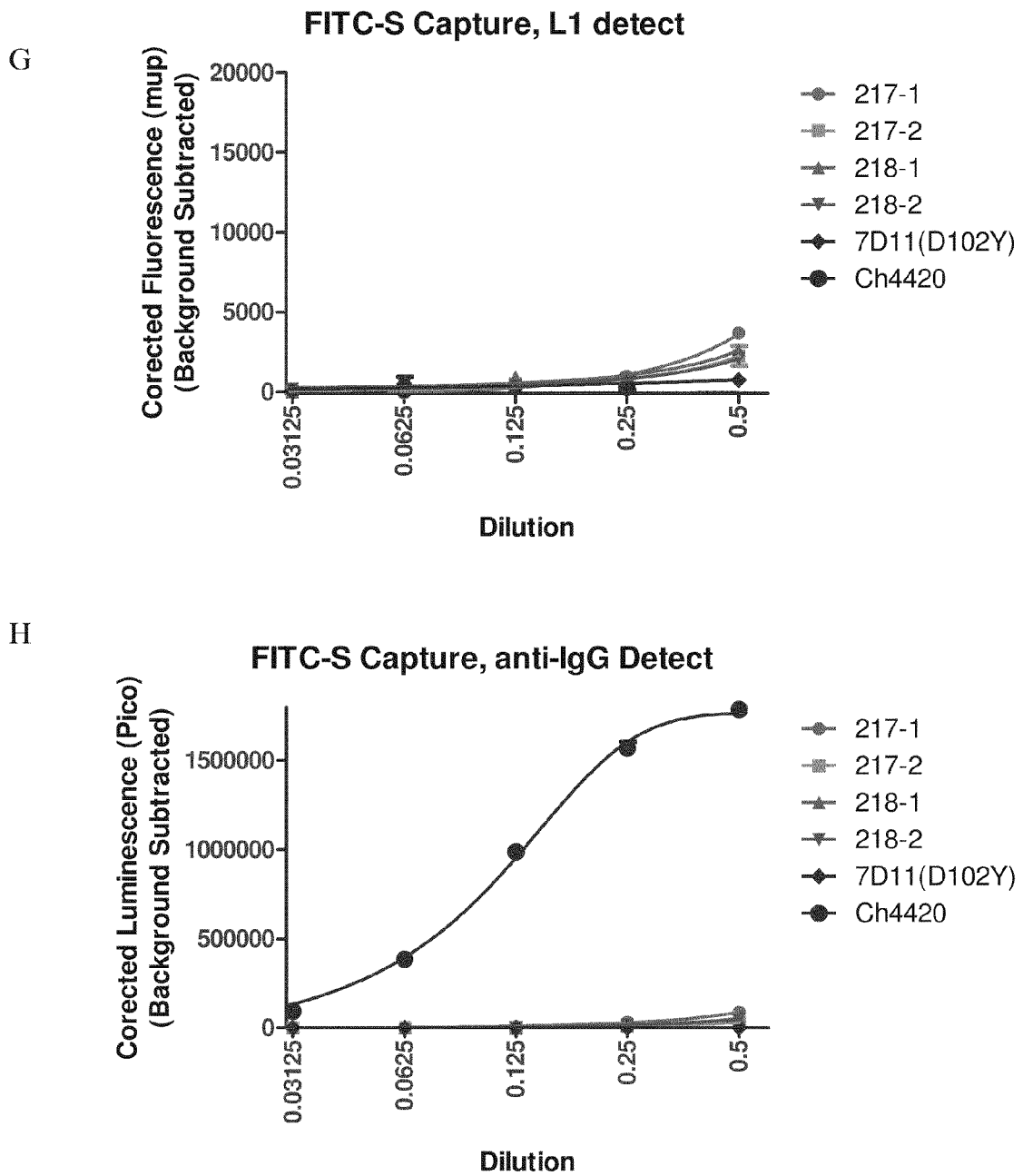
Figure 29(G-H)

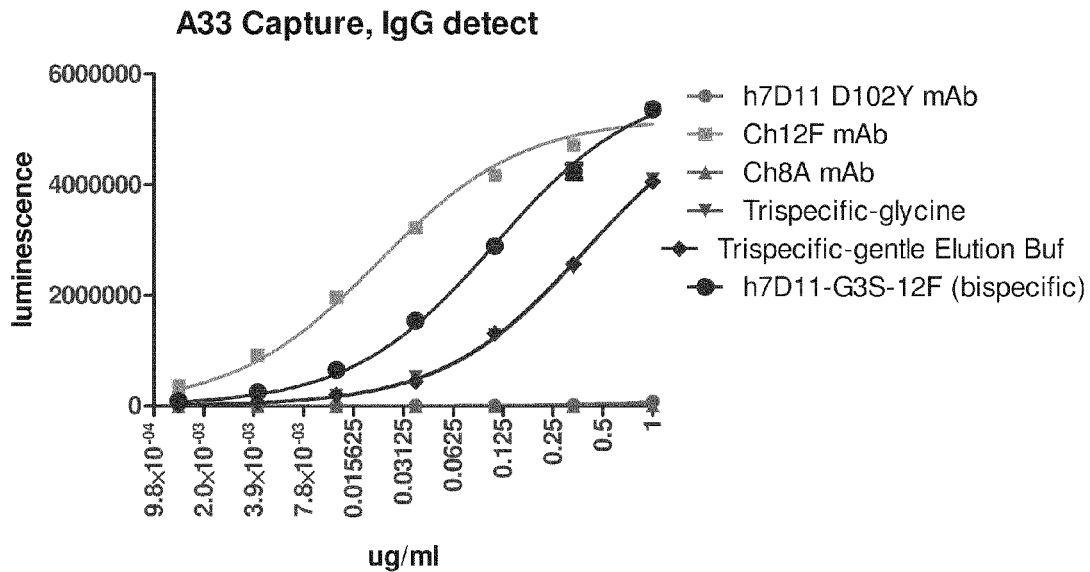
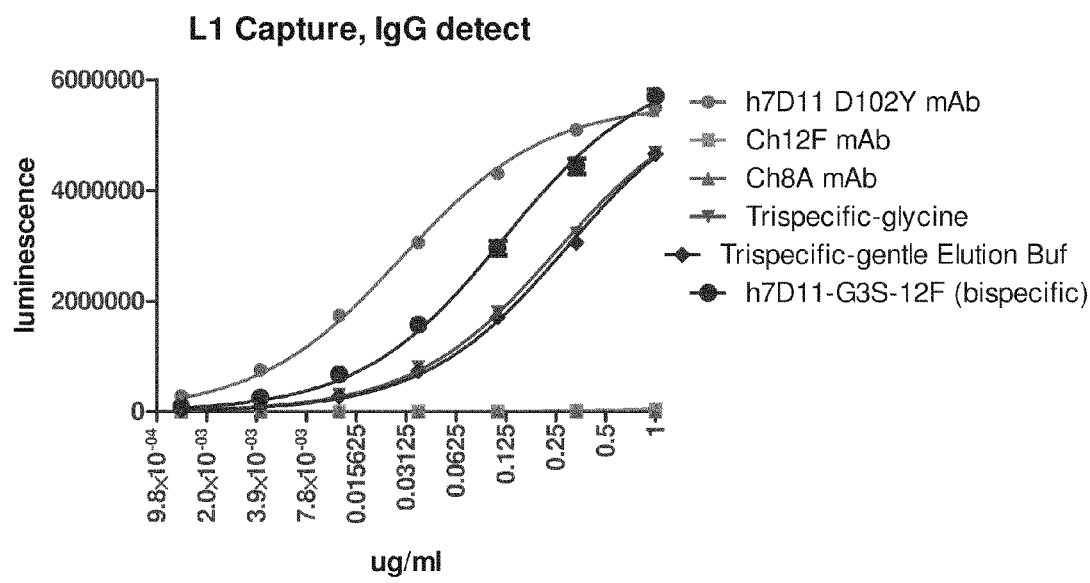
Figure 30 (A-B)

A 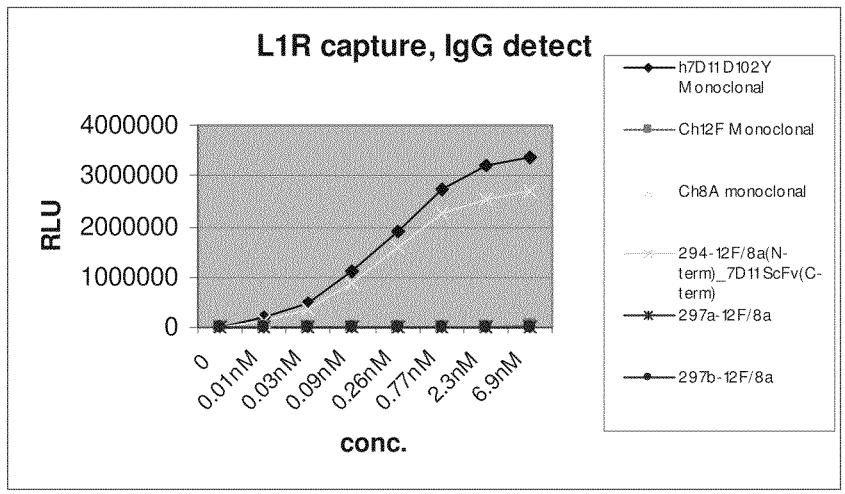
B 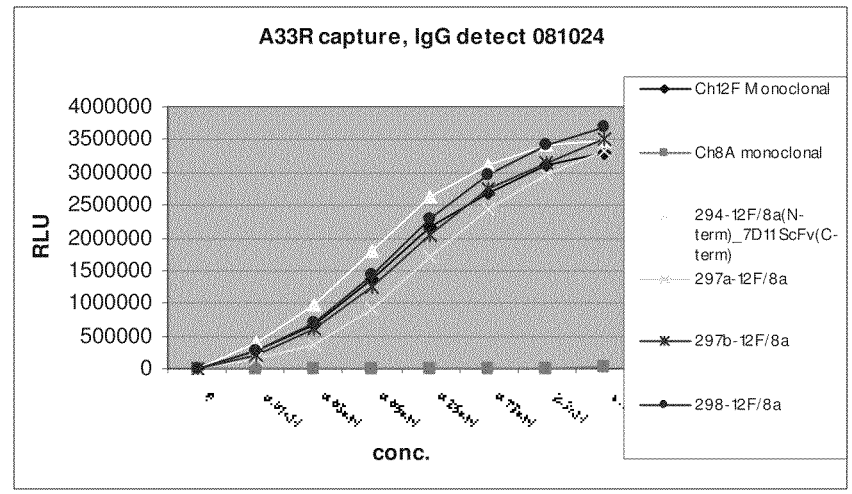
C 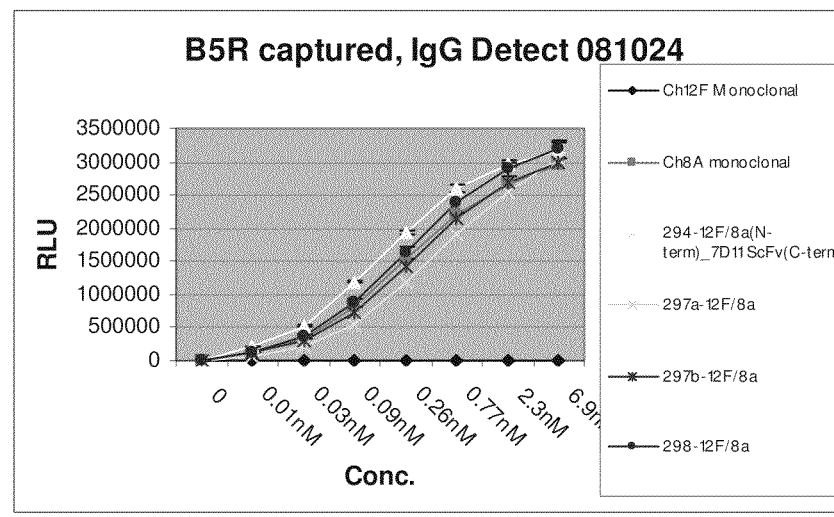
Figure 33

A
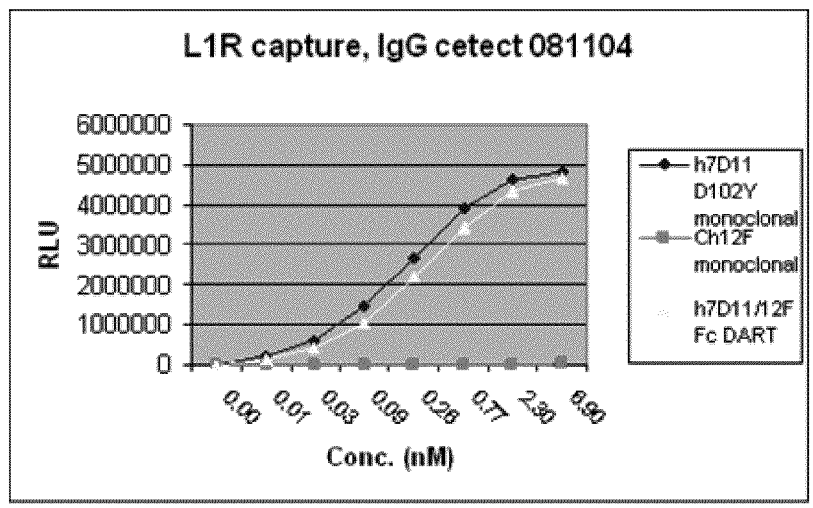
B
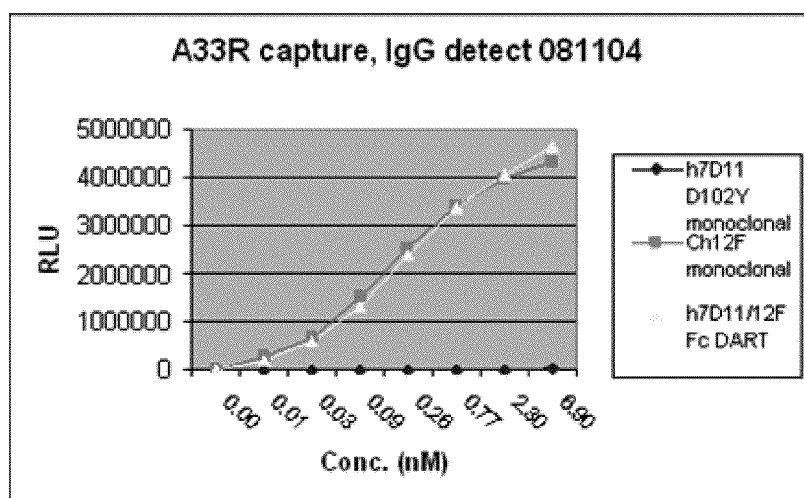
C
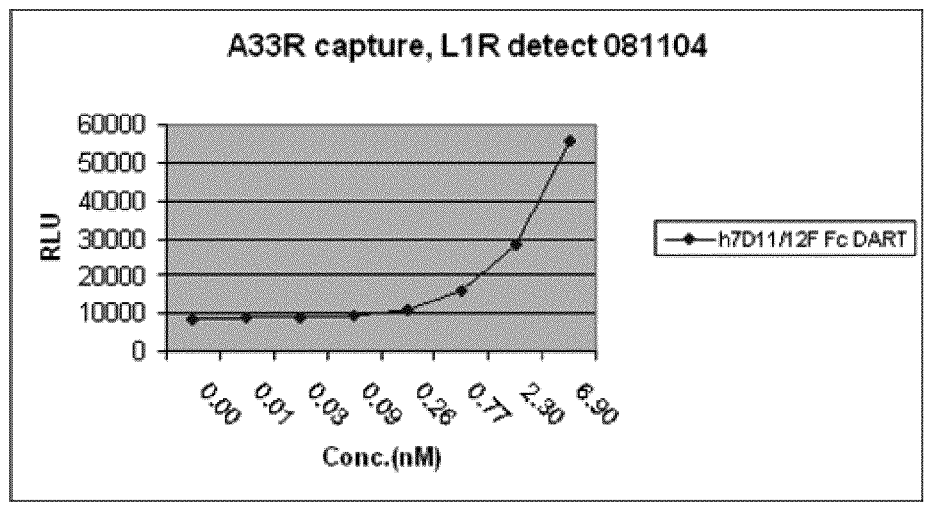
Figure 34

COMPOSITIONS FOR THE PREVENTION AND TREATMENT OF SMALLPOX

CROSS-REFERENCE TO RELATED APPLICATIONS

This application claims priority to U.S. Provisional Patent Application Ser. No. 61/015,106 filed on Dec. 19, 2007, which is incorporated herein by reference in its entirety.

INCORPORATION-BY-REFERENCE OF SEQUENCE LISTING

This application contains a paper copy of a Sequence Listing and a computer readable Sequence Listing (one electronically submitted text file), which Sequence Listings are incorporated herein by reference in their entirety.

BACKGROUND OF THE INVENTION

1. Field of the Invention

The present invention relates to improved compositions for the prevention and treatment of smallpox, and in particular to the use of compositions containing an antibody that binds to an epitope found on the MV form of the smallpox virus and an antibody that binds to an epitope found on the EV form of the smallpox virus. The invention relates to such compositions, especially to non-blood derived antibody compositions, such as chimeric or humanized antibodies, and to methods for their use in imparting passive immunity against smallpox infection to individuals at risk of smallpox virus infection or who exhibit smallpox.

2. Description of Related Art

"Smallpox" (also known by the Latin names Variola or *Variola vera*) is a disease caused by viruses ("smallpox viruses") of the family poxyiridae, subfamily chordopoxyirinae. The lifecycle of poxviruses is complicated by having multiple infectious forms, with differing mechanisms of cell entry. It is a large virus, with a double stranded DNA genome of about 200 kilobases, making it more complicated than the smallest bacteria.

The infectious dose of variola virus is very small, possibly only a few virions. Respiratory infection is characterized by non-infectious incubation and prodromal periods that normally last 12-14 and 2-4 days, respectively (McClain, D. J. (1997) "Smallpox," In: TEXTBOOK OF MILITARY MEDICINE (Zatjchuk R, ed.); Washington, D.C.: Office of the Surgeon General, Walter Reed Medical Center; pp. 539-559). This non-infectious period may represent the window of opportunity for post-exposure treatment by a neutralizing monoclonal antibody product. Variola travels from the upper to lower respiratory tract to regional lymph nodes where it replicates. Asymptomatic viremia occurs on about the third or fourth day after infection and variola then disseminates systemically to other lymphoid tissues, spleen, liver, bone marrow and lung. A second viremia begins at about the eighth day. The prodromal period, which begins about day 12, is characterized by high fever, malaise, backache and headache. At this time, the virus, contained in leukocytes, localizes in small blood vessels of the dermis and beneath the oral and pharyngeal mucosa and subsequently infects adjacent cells. The onset of the infectious state is characterized by the appearance of enanthem (oropharyngeal lesions) and soon followed by exanthem (skin lesions) on the face, hands and forearms. The lesions on mucous membranes shed infected epithelial cells and give rise to infectious oropharyngeal secretions, which are the most important means of virus transmission to contacts. Rash spreads centrally during the next week to the trunk and lesions progress from macules to papules to pustular vesicles. Lesions display a centrifugal distribution and generally remain in a synchronous stage of development in various segments of the body. Scab formation occurs 10-14 days after onset of rash and scab separation occurs during the following 14 days. Because virus can be isolated from scabs, patients are considered infectious until all scabs separate. Smallpox has little effect on the vital organs in the body. Death, which generally occurs during the second week of illness, is usually the result of the toxemia associated with circulating immune complexes and soluble variola antigens, which leads to disseminated intravascular coagulation, hypotension and cardiovascular collapse.

Person-to-person transmission of smallpox is initiated by the deposition of virus in the respiratory tract of the contact; the virus having originated from oropharyngeal secretions of a person with a rash. Epidemiological studies have implicated large-particle aerosol droplets, resuspension of virus particles, and droplet nuclei as possibly important in natural transmission of variola virus (Downie, A. W. et al. (1958) "*The Antibody Response In Man Following Infection With Viruses Of The Pox Group. III. Antibody Response In Smallpox*," J. Hyg. (Lond) 56(4):479-487). The large-particle aerosol droplets are thought to infect the upper respiratory tract, where as the droplet nuclei may initiate infection in the lower respiratory tract. A bioterrorist release of variola or monkeypox viruses is likely to be by droplet nuclei, and thus the lower respiratory tract may be a site of infection. The intranasal and aerosol methods of infection mimic large-particle droplet and droplet nuclei modes of infection, respectively.

Smallpox virus infection is associated with very high morbidity and high overall mortality rates. The classic (or ordinary) form of variola major infection resulted in fatality rates of 30% for unvaccinated individuals and 3% for vaccinated individuals (McClain, D. J. (1997) "*Smallpox*," In: TEXTBOOK OF MILITARY MEDICINE (Zatjchuk R, ed.); Washington, D.C.: Office of the Surgeon General, Walter Reed Medical Center; pp. 539-559). Approximately 2-5% of cases presented as flat-type smallpox, which was associated with severe systemic toxicity and fatality rates of 95% for unvaccinated individuals and 66% for vaccinated individuals. Fewer than 3% of cases presented as hemorrhagic-type smallpox, which was uniformly fatal; death occurred before typical pox lesions developed. Infection with variola minor, a less virulent variant of the variola virus, resulted in fatality rates of 1% in unvaccinated individuals. Patients who recovered from smallpox may be left with serious sequelae, including extensive scarring of the skin, hearing loss or blindness or, more rarely, other organ damage. Smallpox was highly contagious; infection invariably resulted in symptomatic disease. The aerosolized virus was capable of spreading over considerable distances, and of inducing infection even at low viral doses.

Smallpox was responsible for an estimated 300-500 million deaths in the 20th century alone. In light of the enormous medical and social significance of the disease, a concerted worldwide inoculation campaign was initiated to eradicate smallpox. In 1979, the World Health Organization certified that the campaign to eliminate naturally occurring smallpox had been successful (Geddes, A. M. (2006) "The *History of Smallpox*," Clin. Dermatol. 24(3):152-157). Smallpox remains the sole human infectious disease to have been completely eradicated from nature (see, e.g., Bazin, H. (2000) THE ERADICATION OF SMALLPOX: EDWARD JENNER AND THE FIRST AND ONLY ERADICATION OF A HUMAN INFECTIOUS DISEASE; Academic Press, NY).

The occurrence of the 2001 U.S. Postal anthrax spore incident has demonstrated the possibility that biological agents might be used by terrorists against population centers. Because bioterrorism has moved from a theoretical risk to a reality, Governments have recognized the importance of taking steps to protect their populations from the consequences of biological and other unconventional terrorist attacks.

Of the organisms that might potentially be used as bioweapons, smallpox poses one of the most formidable risks to public health (Henderson, D. A. (1998) "Bioterrorism as a public health threat," Emerg. Infect. Dis. 1998 July-September; 4(3):488-92; Wittek, R. (2006) "*Vaccinia Immune Globulin Current Policies, Preparedness, And Product Safety And Efficacy*," Int. J. Infect. Dis. 10(3):193-201). As discussed above, the disease exhibits high morbidity, mortality and contagiousness even at low doses. Vaccinations against smallpox were stopped in light of the eradication of the naturally occurring disease. Thus, most people have not been vaccinated and among those who have been vaccinated, immunity to the virus is declining due to the passage of time. As a consequence, U.S. and world populations are now highly susceptible to smallpox. In light of the latency period associated with the disease, if virus was released in an unnoticeable manner—for example, by exploding a light bulb containing virus in a city subway system (Henderson, D. A. (1998) "*Bioterrorism As A Public Health Threat*," Emerg. Infect. Dis. 1998 July-September; 4(3):488-492)—the resultant infections would be undetected for approximately 2 weeks and could thus easily be spread to numerous contacts. Significantly, the inexperience of current-day physicians with diagnosing smallpox would introduce additional delays in effecting treatment and thus would allow further spread to occur. As stated above, vaccination at the time of appearance of symptoms would be too late to provide effective protection. Accordingly, despite the eradication of naturally occurring smallpox, a need exists for modalities capable of protecting world populations from a smallpox bioweapons attack.

One approach for achieving such protection would be to re-initiate a vaccination regimen. First generation, conventional smallpox vaccines used live vaccinia virus prepared from calf lymph (e.g., Dryvax® (Wyeth Laboratories) or Lister Elstree (Kretzschmar, M. et al. (2006) "*Frequency of Adverse Events after Vaccination with Different Vaccinia Strains*," PLoS Medicine 3(8):e272 doi:10.1371/journal.pmed.0030272). Although these vaccines were employed to eradicate smallpox worldwide, they cause a relatively high level of complications and are contraindicated in populations such as the immunosuppressed, pregnant females and the very young (Fulginiti, V. A. et al. (2003) "*Smallpox Vaccination: A Review, Part II. Adverse Events*," Clin. Infect. Dis. 37(2):251-271). In addition, due to the emergence of myo/pericarditis in vaccinees in recent civilian and military vaccination programs, contraindications have been updated to include persons with cardiac disease or certain risk factors for cardiac disease (Centers for Disease Control and Prevention (2003) "*Update: Cardiac-Related Events During The Civilian Smallpox Vaccination Program—United States, 2003*," Morbidity Mortality Weekly Rep. 52:492-496). Thus, live vaccinia virus vaccines prepared from calf lymph are no longer considered acceptable by current standards for human biologicals.

In the event of an imminent bioterrorist attack, vaccinia virus vaccine could be administered prophylactically. In case of exposure from a bioterrorist attack, post-exposure vaccination can be effective, particularly when utilized in a ring vaccination strategy (Kretzschmar, M. et al. (2004) "*Ring Vaccination And Smallpox Control*," Emerg. Infect. Dis. 10(5):832-841). However, the window of opportunity for treatment of infected individuals is short—the vaccine must be administered within 4 days of first exposure to offer some protection against acquiring infection and significant protection against fatal outcome (Dixon, C. W. (1962) S$_{MALLPOX}$ (1$^{st}$ Ed.) London: Churchill Ltd.; Henderson, D. A. et al. (1999) "*Smallpox As A Biological Weapon: Medical And Public Health Management. Working Group On Civilian Biodefense*," J. Amer. Med. Assn. 281(22):2127-2137). The ineffectiveness of vaccination at later times most likely reflects the inability to generate a robust antibody response within the 2 week period prior to the onset of disease. Studies with monkeypox virus in rhesus monkeys have established that neutralizing antibodies are the most critical arm of a protective immune response against orthopoxvirus infection (Edghill-Smith, Y. et al. (2005) "*Smallpox Vaccine Does Not Protect Macaques With AIDS From A Lethal Monkeypox Virus Challenge*," J. Infect. Dis. 191(3):372-381; Edghill-Smith, Y. et al. (2005) "*Smallpox Vaccine-Induced Antibodies Are Necessary And Sufficient For Protection Against Monkeypox Virus*," Nat. Med. 11(7):740-747).

Second generation vaccines are being developed in light of such deficiencies. ACAM2000™ (Acambis Inc.) is a live vaccinia virus vaccine derived from a Dryvax plaque and produced from large scale Vero cell bioreactors under serum-free conditions. ACAM2000™, however, has been reported to have a vaccination success rate, antibody response, and safety profile similar to that of Dryvax® (Artenstein, A. W. et al. (2005) "*A Novel, Cell Culture-Derived Smallpox Vaccine In Vaccinia-Naive Adults*," Vaccine 23(25):3301-3309). ACAM2000® has been approved by the U.S. Food & Drug Administration for use in persons determined to be at high risk of smallpox infection.

MVA-BN® (Bavarian Nordic) (or IMVAMUNE® (Bavarian Nordic)) is a third generation smallpox vaccine candidate being developed for use in individuals, such as immunocompromised individuals, who are contraindicated for the conventional vaccine. MVA (modified vaccinia virus Ankara) is a highly attenuated virus, having been passaged more than 500 times in chicken embryo fibroblast cells. MVA is replication deficient in most mammalian cell lines and subcutaneous vaccination with MVA does not result in a "vaccine take" (pustule, scab, and scar) (Stittelaar, K. J. et al. (2005) "*Modified Vaccinia Virus Ankara Protects Macaques Against Respiratory Challenge With Monkeypox Virus*," J. Virol. 79(12): 7845-7851). Vaccinations with MVA-BN® are reported to be well-tolerated and to lead to seroconversion at high dose, indicating that the vaccine appears to be efficacious (see Vollmar, J. et al. (2006; Epub 2005 Nov. 28) "*Safety And Immunogenicity Of IMVAMUNE, A Promising Candidate As A Third Generation Smallpox Vaccine*," Vaccine 24(12): 2065-2070). Significantly, MVA-BN is administered by injection instead of by pricking the skin with a bifurcated needle, thus, unlike conventional vaccines it is not easy to distinguish vaccinated individuals from unvaccinated individuals. The vaccine's effectiveness in "at-risk" individuals has not yet been determined. Moreover, it is not known whether any of the second or third generation vaccines would be capable of eliciting protective immunity rapidly enough to protect populations in the event of a smallpox bioweapon attack.

Passive antibody products have been proposed as an alternative approach for defending against biological weapons. Such products may be used either as a prophylactic or as a therapeutic regime in the period immediately following bioweapon exposure (Casadevall, A. et al. (2004) "*Passive Antibody Therapy for Infectious Diseases*," Nat. Rev. Microbiol.

2(9):695-703; Henderson, D. A. et al. (1999) "*Smallpox As A Biological Weapon: Medical And Public Health Management. Working Group On Civilian Biodefense*," J. Amer. Med. Assn. 281(22):2127-2137).

Vaccinia-immune globulin (VIG) has been recommended for the treatment of serious complications of smallpox vaccination, although its therapeutic value has not been fully proven (Kempe, C. H. (1960) "*Studies Smallpox And Complications Of Smallpox Vaccination*," Pediatrics 26:176-189; Kempe, C. H. et al. (1961) "*The Use Of Vaccinia Hyperimmune Gamma-Globulin In The Prophylaxis Of Smallpox*," Bull World Health Organ. 25:41-48; Bray, M. et al. (2003) "*Progressive Vaccinia*," Clin. Infect. Dis. 36(6):766-774; Thorne, C. D. et al. (2003) "*Emergency Medicine Tools To Manage Smallpox (Vaccinia) Vaccination Complications: Clinical Practice Guideline And Policies And Procedures*," Ann. Emerg. Med. 42(5):665-680; Hopkins, R. J. et al. (2004) "*Clinical Efficacy Of Intramuscular Vaccinia Immune Globulin: A Literature Review*," Clin. Infect. Dis. 39(6):819-826; U.S. CDC (2002) "*Vaccinia Immune Globulin: Indications, Precautions & Contraindications*,"). VIG is a pool of γ-globulin that was originally collected from convalescent patients, but is now collected from vaccinees (Kempe, C. H. et al. (1956) "*Hyperimmune Vaccinal Gamma Globulin; Source, Evaluation, And Use In Prophylaxis And Therapy*," Pediatrics 18(2):177-188; Anderson, S. G. et al. (1970) "*The International Standard For Anti-Smallpox Serum*," Bull. World Health Organ. 42(4):515-523). Because initial preparations of VIG contained a high proportion of aggregated protein, it could not be administered intravenously (IV), but was instead needed to be injected intramuscularly (IM). After certification of the eradication of smallpox, no international stockpile of VIG was constituted or maintained, and national stocks were not renewed as they aged and decreased in potency. However, the emergence of HIV has placed restrictions on the safe and effective use of smallpox vaccines and made the need for VIG, or an alternative immunotherapeutic preparation, an important consideration for outbreak control.

VIGIV is a new formulation of VIG that is suitable for IV administration; it is prepared from the plasma of vaccinated military personnel. VIGIV was approved by the FDA in 2005 (Shearer, J. D. et al. (2005) "*Biological Activity Of An Intravenous Preparation Of Human Vaccinia Immune Globulin In Mouse Models Of Vaccinia Virus Infection*," Antimicrob. Agents Chemother. 49(7):2634-2641; Hopkins, R. J. et al. (2004) "*Safety And Pharmacokinetic Evaluation Of Intravenous Vaccinia Immune Globulin In Healthy Volunteers*," Clin. Infect. Dis. 39(6):759-766). According to CDC estimates, 21-247 VIG-treatable complication will be encountered per million vaccinees. Thus, for a U.S. population of 302,000,000, a stockpile of 6,300-75,000 doses of VIG would be required.

In patients infected with smallpox, VIG has been suggested to suppress the secondary viremia and to ameliorate the disease (Kempe, C. H. et al. (1956) "*Hyperimmune Vaccinal Gamma Globulin; Source, Evaluation, And Use In Prophylaxis And Therapy*," Pediatrics 18(2):177-188). In a murine model in which onset of disease occurs approximately 4 days following intranasal vaccinia virus infection, VIG was effective when administered prior to the appearance of disease (Law, M. et al. (2005) "*An Investigation Of The Therapeutic Value Of Vaccinia-Immune IgG In A Mouse Pneumonia Model*," J. Gen. Virol. 86(Pt 4):991-1000). These data are consistent with the limited studies of the 1950's and 1960's that show that VIG appears to be effective in variola virus-infected human subjects if administered at or before the onset of disease (Kempe, C. H. et al. (1956) "*Hyperimmune Vacci-nal Gamma Globulin; Source, Evaluation, And Use In Prophylaxis And Therapy*," Pediatrics 18(2):177-188; Kempe, C. H. et al. (1961) "*The Use Of Vaccinia Hyperimmune Gamma-Globulin In The Prophylaxis Of Smallpox*," Bull World Health Organ. 25:41-48). VIG contains relatively high titers of anti-A33, anti-B5 and anti-A27 antibodies, but is relatively deficient in anti-L1 antibodies (Lawrence, S. J. et al. (2007) "*Antibody Responses To Vaccinia Membrane Proteins After Smallpox Vaccination*," J. Infect. Dis. 196(2):220-229). Unfortunately, blood-derived products, such as VIG and VIGIV, have inherent deficiencies, are variable in activity and are limited in supply.

Monkeypox is a disease caused by an orthopoxvirus (monkeypox virus) (Bricaire, F. et al. (2006) "*Emerging Viral Diseases*," Bull. Acad. Natl. Med. 190(3):597-608, 609, 625-627; Heeney, J. L. (2006) "*Zoonotic Viral Diseases And The Frontier Of Early Diagnosis, Control And Prevention*," J. Intern. Med. 260(5):399-408; Sale, T. A. et al. (2006) "*Monkeypox: An Epidemiologic And Clinical Comparison Of African And US Disease*," J. Am. Acad. Dermatol. 55(3):478-481; Nalca, A. et al. (2005) "*Reemergence Of Monkeypox: Prevalence, Diagnostics, And Countermeasures*," Clin. Infect. Dis. 41(12):1765-1771; Prichard, M. N. et al. (2005) "*Orthopoxvirus Targets For The Development Of Antiviral Therapies*," Curr. Drug Targets Infect. Disord. 5(1):17-28; Ligon, B. L. (2004) "Monkeypox: a review of the history and emergence in the Western hemisphere," Semin. Pediatr. Infect. Dis. 15(4):280-287; Abrahams, B. C. et al. (2004) "*Anticipating Smallpox And Monkeypox Outbreaks: Complications Of The Smallpox Vaccine*," Neurologist 10(5):265-274; Di Giulio, D. B. et al. (2004) "*Human Monkeypox: An Emerging Zoonosis*," Lancet Infect. Dis. 4(1):15-25 (Erratum; Lancet Infect. Dis. (2004) 4(4):251); Heymann, D. L. et al. (1998) "*Re-Emergence Of Monkeypox In Africa: A Review Of The Past Six Years*," Brit. Med. Bull. 54(3):693-702; Cho, C. T. et al. (1973) "*Monkeypox Virus*," Bacteriol. Rev. 37(1):1-18).

Cases of human monkeypox are increasing in Africa, and an outbreak even occurred in the U.S. in 2003 (Parker, S. et al. (2007) "*Human Monkeypox: An Emerging Zoonotic Disease*," Future Microbiol. 2:17-34). Monkeypox presents as a smallpox-like rash preceded by a 10-14 day incubation period. A prodromal fever, malaise and severe lymphadenopathy are common; mortality is approximately 10%. Monkeypox may be transmitted from human-to-human. However, unlike variola virus, which has no nonhuman host, monkeypox virus is amplified and maintained in wild-animal populations, such as rodents and nonhuman primates. Because of the higher prevalence of immunocompromised individuals, particularly in Sub-Saharan Africa as a result of the spread of HIV infection, the impact of human vaccination as an effective control measure is declining. The increased frequency of human monkeypox infections, especially in immunocompromised individuals, might permit the monkeypox virus to evolve and maintain itself independently in human populations. Monkeypox virus could also be used as a bioweapon; it is readily available in Africa and its genome could be manipulated to increase its virulence, such as by inserting an IL-4 gene (Parker, S. et al. (2007) "*Human Monkeypox: An Emerging Zoonotic Disease*," Future Microbiol. 2:17-34).

In sum, despite all prior advances, a need remains for compositions that could be used to provide a rapid and effective response to an orthopox virus (e.g., smallpox virus, monkeypox virus, etc.) bioweapon attack. The present invention, which provides a cocktail of neutralizing monoclonal antibodies is directed to this and related needs.

SUMMARY OF THE INVENTION

The present invention relates to improved compositions for the prevention and treatment of smallpox, and in particular to the use of compositions containing an antibody that binds to an epitope found on the MV form of the smallpox virus and an antibody that binds to an epitope found on the EV form of the smallpox virus. The invention relates to such compositions, especially to non-blood derived antibody compositions, such as chimeric or humanized antibodies, and to methods for their use in imparting passive immunity against smallpox infection to individuals at risk of smallpox virus infection or who exhibit smallpox.

In detail, the invention provides a composition comprising:
(A) a non-blood derived antibody, or fragment thereof, wherein the antibody or the fragment immunospecifically binds to an epitope found on an MV form of the smallpox virus; and
(B) a non-blood derived antibody, or fragment thereof, wherein the antibody or the fragment that immunospecifically binds to an epitope found on an EV form of the smallpox virus.

The invention additionally concerns the embodiment of such composition wherein the non-blood derived antibody (A) and/or is the non-blood derived antibody (B) is/are selected from the group consisting of a chimeric antibody and a humanized antibody.

The invention additionally concerns the embodiment of such composition wherein the composition comprises a DART that comprises such fragment of such non-blood derived antibody (A), that comprises such fragment of such non-blood derived antibody (B), or that comprises such fragment of both such non-blood derived antibodies (A) and (B).

The invention additionally concerns the embodiment of the above-described compositions wherein the DART is an IgDART that immunospecifically binds to:
(A) an epitope found on an MV form of the smallpox virus; and
(B) an epitope found on an EV form of the smallpox virus.

The invention additionally concerns the embodiments of such compositions wherein the non-blood derived antibody (A) immunospecifically binds to an epitope of an L1 protein of the smallpox virus (especially an epitope of the L1 protein located within non-contiguous domains of L1, the domains having the amino acid sequences of SEQ ID NOS:13-15).

The invention additionally concerns the embodiments of such compositions wherein the non-blood derived antibody (B) immunospecifically binds to an epitope of an A33 protein of the smallpox virus (especially an epitope of the A33 protein located within a domain of A33, the domain having the amino acid sequence of SEQ ID NO:40), or to an epitope of a B5 protein of the smallpox virus (especially an epitope of the B5 protein located within a domain of B5, the domain having the amino acid sequence of SEQ ID NO:41).

The invention additionally concerns the embodiments of such compositions wherein the non-blood derived antibody (A) is the chimeric antibody Ch7D11, or is a humanized 7D11 antibody (especially the humanized 7D11 antibody h7D11, or a variant of the humanized antibody h7D11, and in particular, an: (A) M48I; (B) I69L; (C) M48I and I69L; (D) V67A; (E) V67A and I69L; or (F) M48I, V67A and I69L variant of the humanized 7D11 antibody h7D11).

The invention additionally concerns the embodiments of such compositions wherein the non-blood derived antibody (B) is the chimeric antibody Ch12F, the chimeric antibody Ch6C or the chimeric antibody Ch8AH8AL.

The invention additionally concerns a non-blood derived antibody selected from the group consisting of Ch7D11, h7D11, Ch12F, Ch6C and Ch8AH8AL. The invention additionally concerns a non-blood derived antibody that is the chimeric antibody Ch7D11, or is a humanized 7D11 antibody (especially the humanized 7D11 antibody h7D11, or a variant of the humanized antibody h7D11, and in particular, an: (A) M48I; (B) I69L; (C) M48I and I69L; (D) V67A; (E) V67A and I69L; or (F) M48I, V67A and I69L variant of the humanized 7D11 antibody h7D11).

The invention additionally concerns a method of imparting passive immunity against smallpox to an individual, wherein the method comprises providing to the individual an effective amount of a composition comprising:
(A) a non-blood derived antibody, or fragment thereof, wherein the antibody or the fragment immunospecifically binds to an epitope found on an MV form of the smallpox virus; and
(B) a non-blood derived antibody, or fragment thereof, wherein the antibody or the fragment that immunospecifically binds to an epitope found on an EV form of the smallpox virus.

The invention additionally concerns the embodiments of such method:
I. wherein the composition is provided to an individual not infected with smallpox virus, and the effective amount imparts prophylactic passive immunity against smallpox; and
II. wherein the composition is provided to an individual infected with smallpox virus, and the effective amount imparts therapeutic passive immunity against smallpox.

The invention additionally concerns the embodiments of such methods wherein the non-blood derived antibody (A) and/or the non-blood derived antibody (B) is/are selected from the group consisting of a chimeric antibody and a humanized antibody.

The invention additionally concerns the embodiment of such method wherein the composition comprises a DART that comprises such fragment of such non-blood derived antibody (A), that comprises such fragment of such non-blood derived antibody (B), or that comprises such fragment of both such non-blood derived antibodies (A) and (B).

The invention additionally concerns the embodiment of the above-described methods wherein the DART is an IgDART that immunospecifically binds to:
(A) an epitope found on an MV form of the smallpox virus; and
(B) an epitope found on an EV form of the smallpox virus.

The invention additionally concerns embodiments of such methods wherein the non-blood derived antibody (A) immunospecifically binds to an epitope of an L1 protein of the smallpox virus (especially an epitope of the L1 protein located within non-contiguous domains of L1, the domains having the amino acid sequences of SEQ ID NOS:13-15).

The invention additionally concerns the embodiments of such methods wherein the non-blood derived antibody (B) immunospecifically binds to an epitope of an A33 protein of the smallpox virus (especially an epitope of the A33 protein located within a domain of A33, the domain having the amino acid sequence of SEQ ID NO:40), or to an epitope of a B5 protein of the smallpox virus (especially an epitope of the B5 protein located within a domain of B5, the domain having the amino acid sequence of SEQ ID NO:41).

The invention additionally concerns the embodiments of such methods wherein the non-blood derived antibody (A) is the chimeric antibody Ch7D11, or is a humanized 7D11 antibody (especially the humanized 7D11 antibody h7D11, or a variant of the humanized antibody h7D11, and in particular, an: (A) M48I; (B) I69L; (C) M48I and I69L; (D) V67A; (E) V67A and I69L; or (F) M48I, V67A and I69L variant of the humanized 7D11 antibody h7D11).

The invention additionally concerns the embodiments of such methods wherein the non-blood derived antibody (B) is the chimeric antibody Ch12F, the chimeric antibody Ch6C or the chimeric antibody Ch8AH8AL.

BRIEF DESCRIPTION OF THE FIGURES

FIG. 1 shows the alignment of mouse 7D11 VH (mVH) (SEQ ID NO:4) and humanized 7D11 VH (hVH) (SEQ ID NO:10).

The doses required for efficacy in post-exposure treatment studies are higher than those required in pre-exposure prophylaxis studies.

FIG. 12 (Panels A-B) shows the results of a study to assess the therapeutic and prophylactic activity of a mAb cocktail composed of a 1:1 mixture of anti-MV+anti-EV mAbs (Ch7D11:Ch12F:Ch6C:Ch8A, 3:1:1:1) in an ectromelia virus intranasal infection of A/NCR mice. Mice were inoculated with ECTV and treated with the antibodies as described in Table 4 or with cidofovir. Animals were monitored for weight loss (Panel A) and survival (Panel B). Because of animal mortality, the weight recovery curves are derived from variable numbers of animals. Survival curves were generated using the Kaplan-Meier method and differences between curves were compared using the log-rank statistic. *$P<0.05$, $P<0.01$, *$P<0.001$, compared to the vehicle treated animals (Cage 2).

FIG. 13 (Panels A-B) provides schematic representations of antibody and DART constructs. Panel A: Antibodies consist of two copies each of two polypeptide chains, light chain (Lc) and heavy chain (Hc). The chains are covalently linked by disulfide bonds (narrow black lines). Each chain has a variable (VL or VH; gray) region and a constant region (CL or CH; black). On each arm of an antibody, the VL and VH make intermolecular contacts to create the antigen binding site (Fv). There are two binding sites per antibody. The Fc region of the antibody consists of the C-terminal part of the constant sequence of the heavy chain. Panel B: Bispecific bivalent DARTs comprise V-regions and linker sequences. As in a conventional antibody, the VL and VH on opposing chains comes together to form an antigen binding site. In this molecule, two distinct antigen binding sites are formed immediately adjacent to each other. Panel C: Monospecific bivalent DARTs are similar to the DARTs described in Panel B, but they have two identical binding sites. For all panels, the amino-(N) and carboxy (C)-termini are indicated.

FIG. 14 (Panels A-C) provide schematic representations of antibody and DART constructs. Panel A: Tetravalent bispecific FcDART units are expressed by appending one chain to the C-terminus of IgG1 Fc and coexpressing the other DART-chain: Fc-[Linker]-VL1-[Linker]-VH2-[C-Terminal Fusion] and VL2-[Linker]-VH1-[C-Terminal Fusion]. The linker can be, for example, GGGSGGGG, and the C-Terminal Fusion can be LGGC. Panel B: Tetravalent monospecific IgDART was made by appending one DART chain to the N terminus of an antibody CH chain and the other to the N terminus of the antibody's CL chain. Panel C: Tetravalent bispecific IgDART constructed as described in Panel B, but with a bispecific DART unit instead of a monospecific one.

FIG. 15 (Panels A-D) shows the synergistic prophylactic and therapeutic activity of combinations of MV and EV mAbs of the present invention. Balb/c mice were injected IP with individual mAbs or 1:1 mAb combinations at a total dose of 100 mg/kg one day prior (Panel A), two days after (Panels B and C) or three days after (Panel D) being infected intratracheally with $1.25\times10^5$ pfu (Panels A, C and D) or with $0.25\times10^5$ pfu (Panel B) of vaccinia virus WR. Animals were monitored for survival for 16 days. Ch7D11 is a chimeric (mouse/human) mAb that targets the L1 protein of MV particles. Ch8A and Ch12F are chimeric (chimp/human) mAbs that target the B5 and A33 proteins, respectively, of EV particles. VIGIV is vaccinia immune globulin intravenous, which was administered at a dose of 500 mg/kg.

FIG. 16 (Panels A-F) shows the prophylactic activity of single mAbs or combinations of mAbs. Balb/c mice were infected intratracheally with $1\times10^5$ pfu vaccinia virus WR. One day prior to infection, 5 mg/kg (Panels A and B), 10 mg/kg single mAbs (Panels C and D) and 10 mg/kg combination mAbs (Panels E and F) were administered by IP injection. The combinations were Ch7D11:Ch8A [1:1], Ch7D11:Ch12F [1:1] and Ch7D11:Ch8A:Ch12F [2:1:1]. Each combination contained an equal ratio of MV and EV mAbs. Animals were monitored for weight loss (Panels A, C, E) and survival (Panels B, D, F) for 16 days post-infection (DPI).

FIG. 17 (Panels A-F) illustrates the dose response of mAbs administered therapeutically at 2 DPI to mice challenged with vaccinia virus at $2.5\times10^4$ pfu. Balb/c mice were infected intratracheally with $2.5\times10^4$ pfu vaccinia virus WR. At 2 days post-infection, saline or mAb combinations were administered by IP injection at a total dose of 0.3 (Panels A and B), 3 (Panels C and D) or 30 (Panels E and F) mg/kg. Animals were monitored for weight loss (Panels A, C, E) and survival (Panels B, D, F) for 16 days post-infection (DPI).

FIG. 18 (Panels A-D) illustrates the dose response of mAbs administered therapeutically at 2 DPI to mice challenged with vaccinia virus at $1.25\times10^5$ pfu. Balb/c mice were infected intratracheally with $1.25\times10^5$ pfu vaccinia virus WR. At 2 days post-infection, mAb combinations Ch7D11:Ch12F (Panels A and B) and Ch7D11:Ch8A (Panels C and D) were administered by IP injection at a total dose of 1, 3, 10 or 30 mg/kg. Animals were monitored for weight loss (Panels A and C) and survival (Panels B and D) for 16 days post-infection (DPI).

FIG. 19 (Panels A-F) illustrates the dose response of mAbs administered therapeutically at 3 DPI to mice challenged with vaccinia virus at $1.25\times10^5$ pfu. Balb/c mice were infected intratracheally with $1.25\times10^5$ pfu vaccinia virus WR. At 3 days post-infection, mAb combinations Ch7D11:Ch12F (Panels A and B), and Ch7D11:Ch8A (Panels C and D) were administered by IP injection at a total dose of 1, 10 or 100 mg/kg. Control reactions (Panels E and F) were administered at 100 mg/kg. Animals were monitored for weight loss (Panels A, C, E) and survival (Panels B, D, F) for 16 days post-infection (DPI).

FIG. 20 (Panels A-D) illustrates the dose response curves for prevention of mortality and estimation of ED50 values. Panel A: Prophylactic administration at −1 DPI. The virus challenge dose was $1\times10^5$ pfu. Panel B: Therapeutic treatment at 2 DPI. The virus challenge dose was $2.5\times10^4$ pfu. Panel C: Therapeutic treatment at 2 DPI. The virus challenge dose was $1.25\times10^5$ pfu. Panel D: Therapeutic treatment at 3 DPI. The virus challenge dose was $1.25\times10^5$ pfu. Prior to their treatment at 3 DPI, the mice exhibited a weight loss of approximately 10%. For data obtained from more than one study, mean values are presented in the figures.

FIG. 21 (Panels A-B) illustrates the optimization of the anti-MV:anti-EV mAb ratio. Balb/c mice were infected intratracheally with $1.25\times10^5$ pfu vaccinia virus WR. At 2 days post-infection, various ratios of Ch7D11:Ch12F (Panel A) or Ch7D11:Ch8A (Panel B) were administered by IP injection at a total dose of 5 mg/kg. This dose corresponds to the ED50 that was defined in FIG. 20, Panel C. This dose was selected to allow detection of either increases or decreases in therapeutic potency. Animals were monitored for survival for 16 days.

FIG. 22 illustrates a C-terminal FcDART that binds two antigens simultaneously. FcDART was produced by transient transfection of 293H cells. IgG content was measured by ELISA, compared to a standard curve (not shown). New ELISA plates were then coated with antigen "A," bound by cell supernatants containing FcDART (anti-A×anti-B) as in FIG. 14 (Panel A) or a bivalent monospecific DART directed against antigen "B" (as in FIG. 13 (Panel C). Binding was then detected using biotinylated antigen "B" followed by streptavidin-HRP and developed with TMB.

Figure 23:
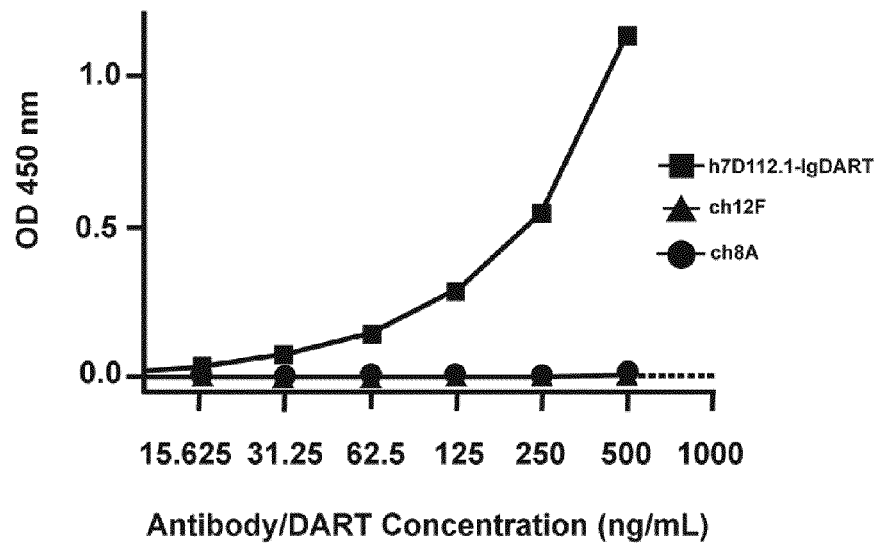

FIG. 23 shows that an h7D11 homodimeric IgDART binds L1 antigen. L1 was bound to the ELISA plate, then purified h7D11 IgDART was bound and detected using an HRP-conjugated anti-IgG antibody and TMB substrate. h7D11 IgDART binds the antigen, while the anti-EV antibodies do not.

Figure 13:
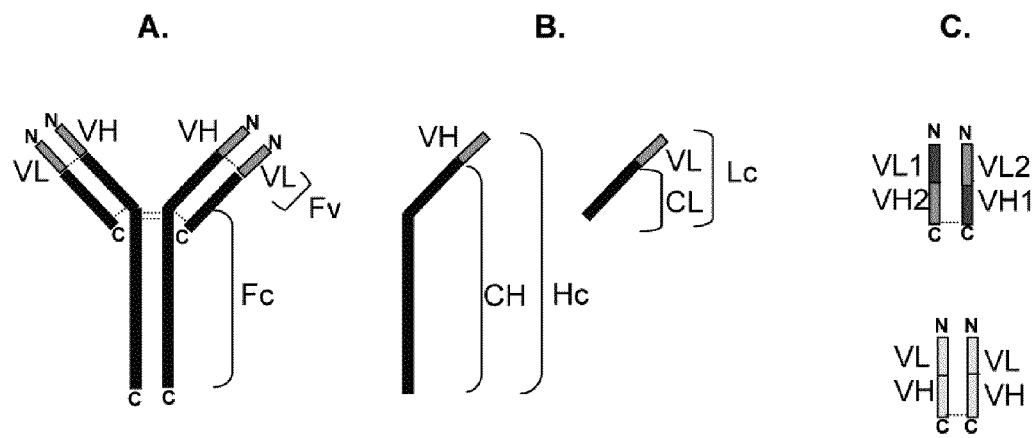
Figure 14:
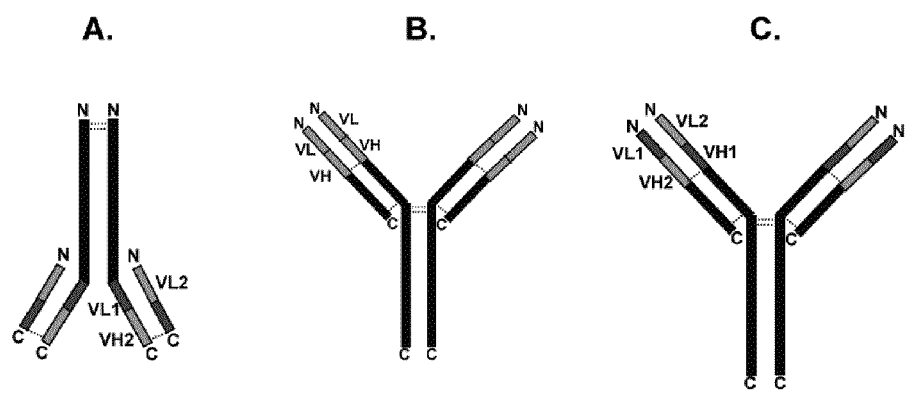
Figure 24:
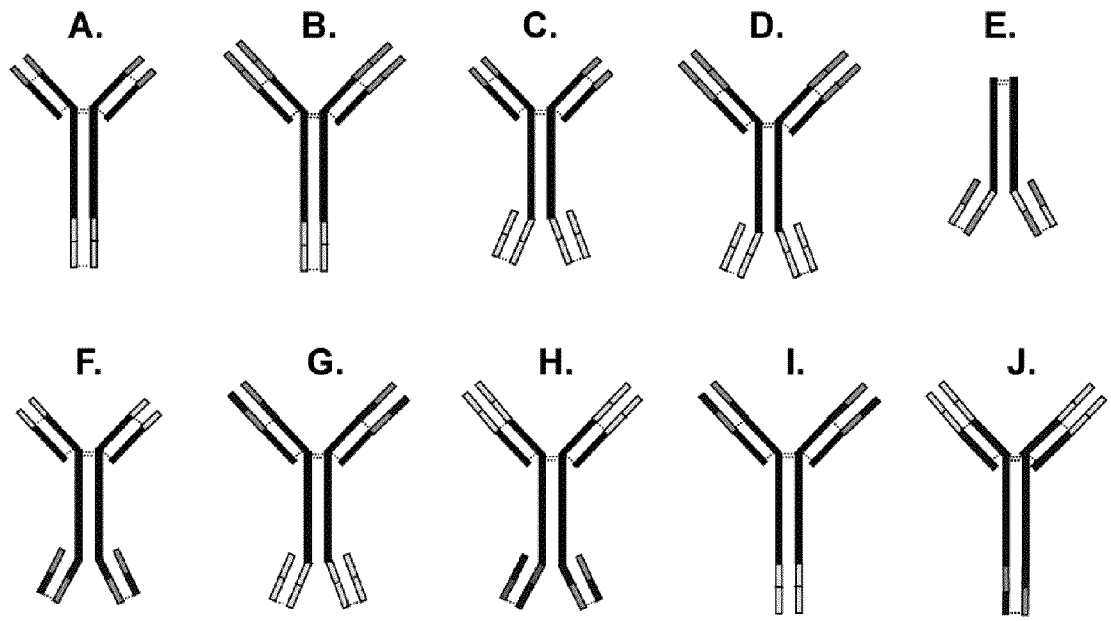

FIG. 24 (Panels A-J) provides schematic representations of IgDART molecules. Specificity is indicated by shade, constant regions are black, and disulfide bonds are indicated by dotted black lines. The N-termini of all protein chains are oriented toward the top of the figure, while the C-termini are oriented toward the bottom. Panels A-E are bispecific and Panels F-J are trispecific. Panels A and E are tetravalent; Panels B, C, F, I, and J are hexavalent; Panels D, G, and H are octavalent. Refer to FIGS. 13 and 14 for detailed descriptions of individual domains.

FIG. 25 (Panels A-C) illustrates structural features of bispecific IgDARTS. Panel A is a schematic depicting different types of linker sequences utilized in constructing bispecific IgDARTS. Panel B illustrates an IgDART containing a monospecific bivalent (Ch7D11) N-terminus and a monospecific bivalent C terminus (Ch12F). Panel C depicts a bispecific IgDART, in which a monospecific bivalent N terminus (Ch7D11) is linked to a monospecific tetravalent C terminus (Ch12F).

Figure 26A:
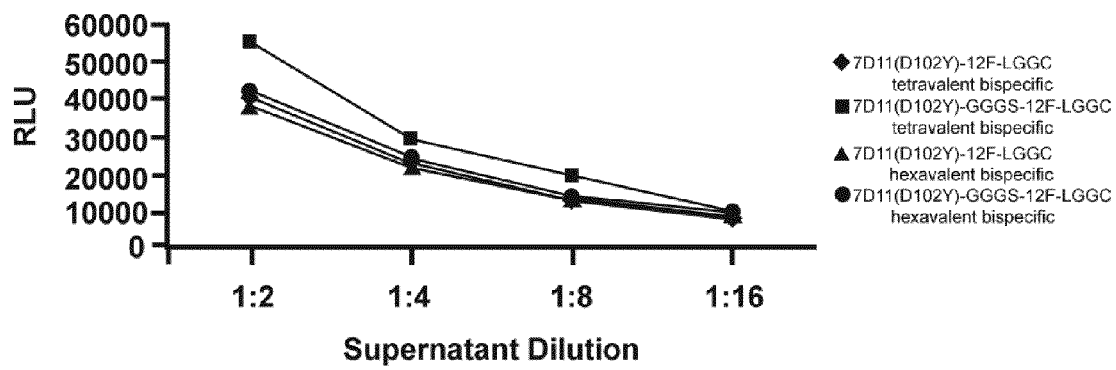
Figure 26B:
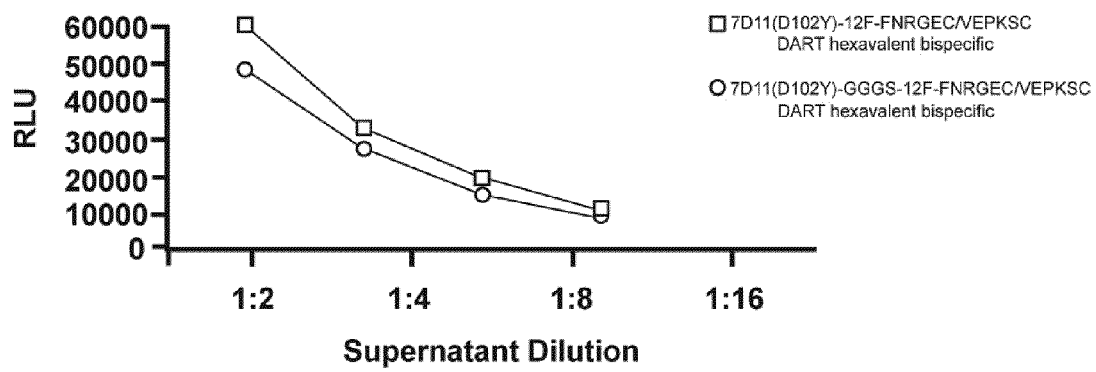
Figure 27A:
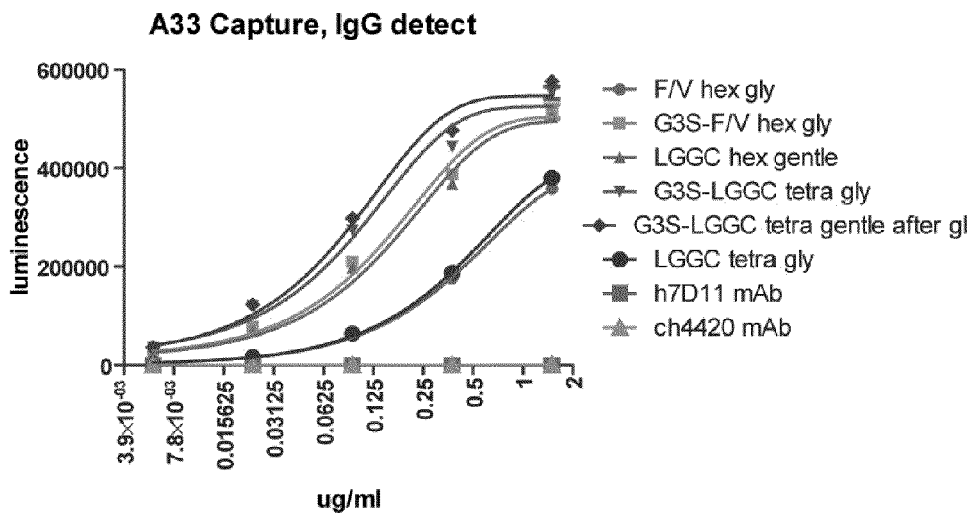
Figure 27B:
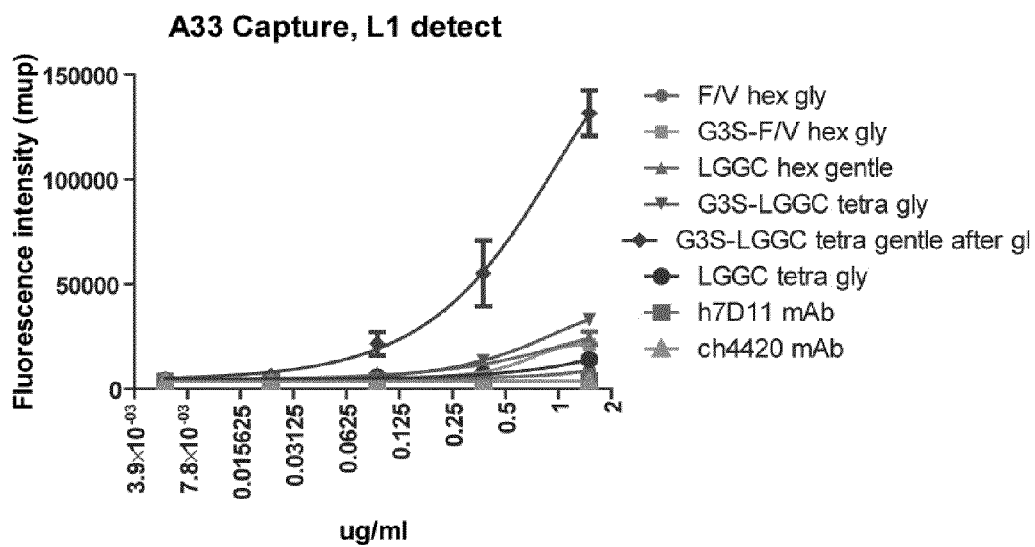
Figure 27C:
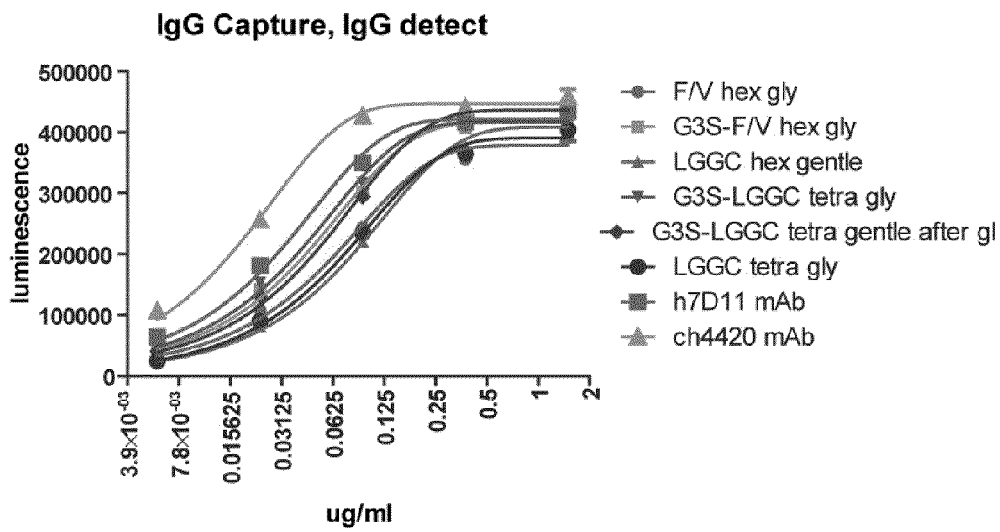
Figure 27D:
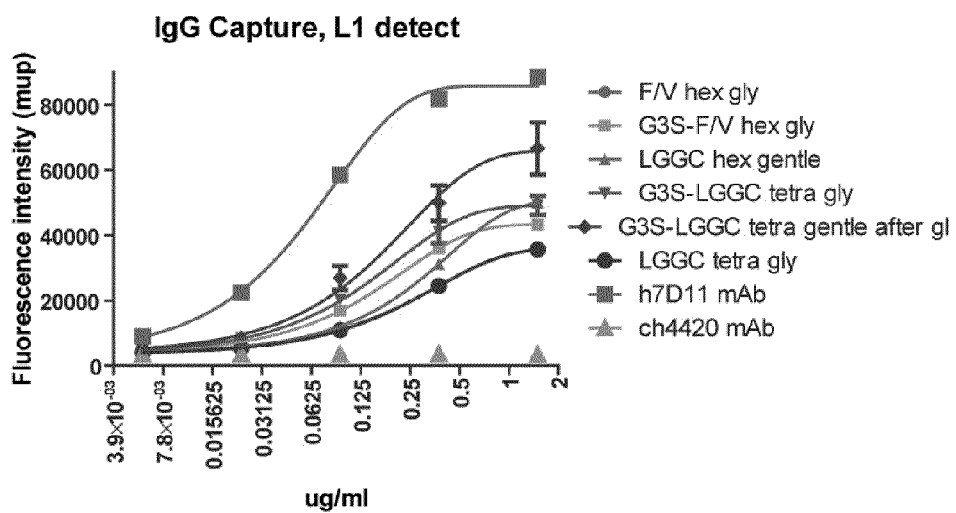

FIG. 26 (Panels A-B) illustrates specificity ELISA assays. ELISA assays to test for dual specificity were performed on crude supernatants containing the following samples: Panel A: 7D11(D102Y)-12F-LGGC tetravalent bispecific; 7D11 (D102Y)-GGGS-12F-LGGC tetravalent bispecific; 7D11 (D102Y)-12F-LGGC hexavalent bispecific; 7D11(D102Y)-GGGS-12F-LGGC hexavalent bispecific; Panel B: 7D11 (D102Y)-12F-FNRGEC/VEPKSC hexavalent bispecific; and 7D11 (D102Y)-GGGS-12F-FNRGEC/VEPKSC hexavalent bispecific IgDARTs. Assay background is around 4000 units.

FIG. 27 (Panels A-B) shows the ability of such bispecific IgDARTS to capture A33 or IgG. ELISAs demonstrated that such IgDARTS did not bind to B5, a finding consistent with the fact that these DARTS do not have a B5 binding epitope.

FIG. 28 (Panels A-B) illustrates the structures of two trispecific IgDARTS. Panel A: IgDART substituents; Panel B: assembled IgDART.

FIG. 29 (Panels A-H) shows the results of ELISAs employing the trispecific IgDARTS, and demonstrates their ability to bind to A33 (Panels A and B), B5 (Panels C and D), IgG (Panels E and F) and FITC-S (Panels G and H).

Figure 30:
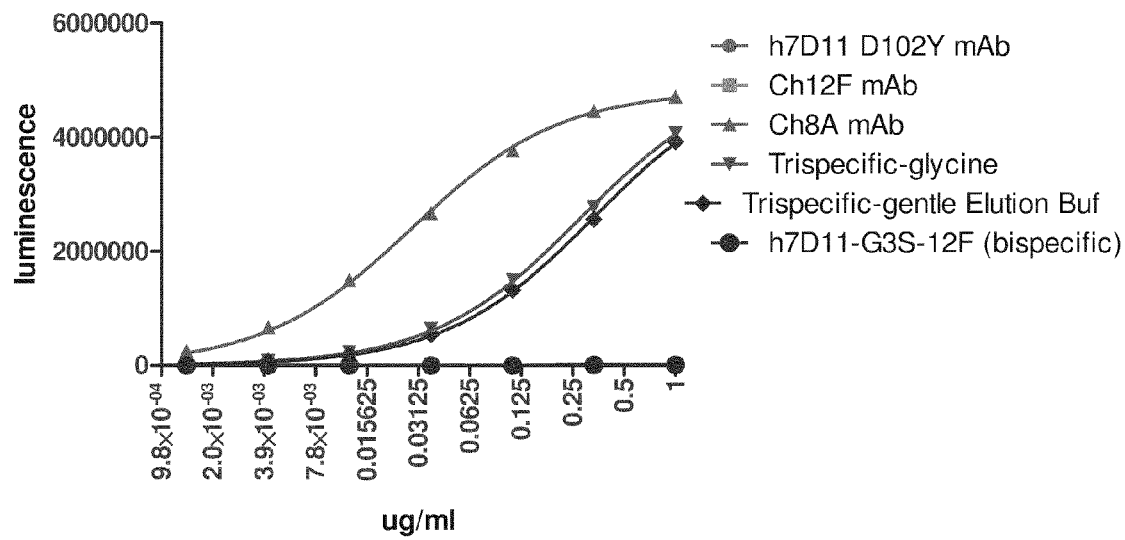

FIG. 30, Panels A-C shows the results of ELISAs employing IgDARTS, and demonstrates the ability of exemplary IgDARTS to bind to A33 (Panel A), L1 (Panel B) and B5 (Panel C).

Figure 31:
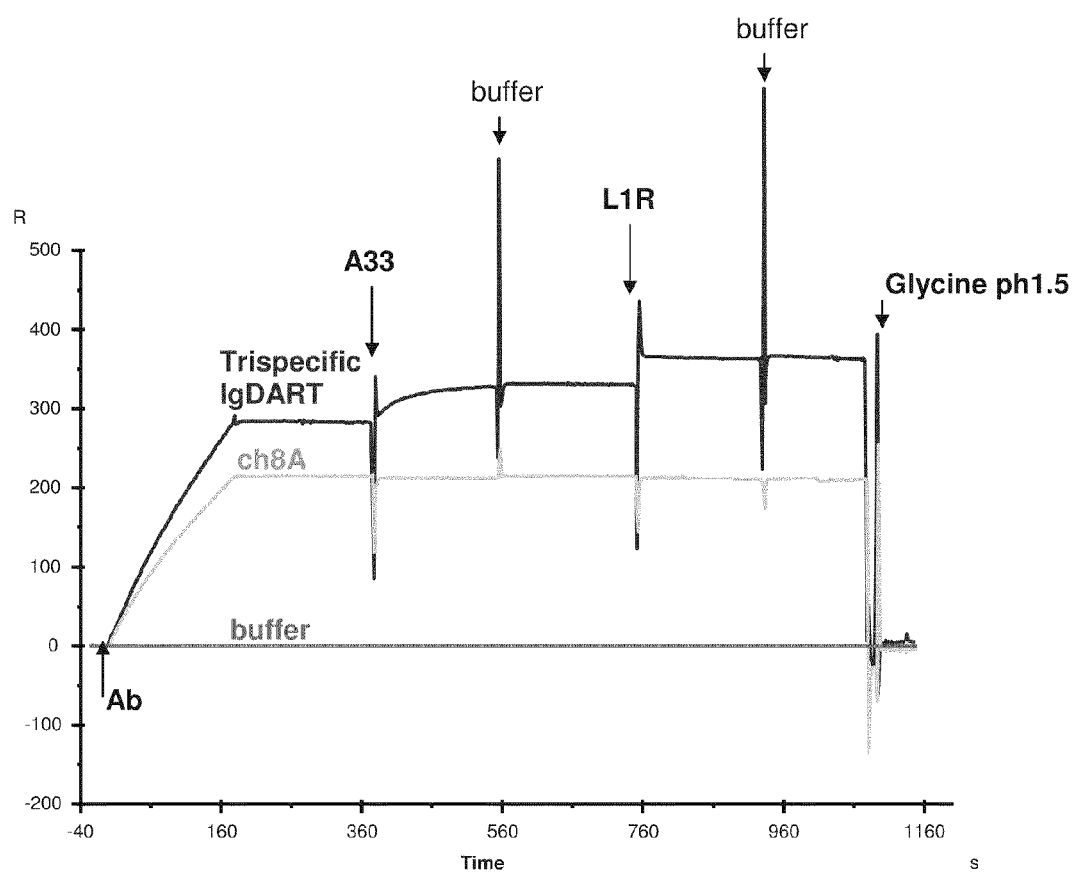

FIG. 31 provides the results of a sequential antigen binding assay. B5 was immobilized on a surface, followed by injection of antibody or buffer over the surface; A33 and L1R were injected consequently, and the complex was washed out from the surface with pulse injection of Glycine pH 1.5. Binding curve started with buffer was subtracted as blank.

Figure 32:
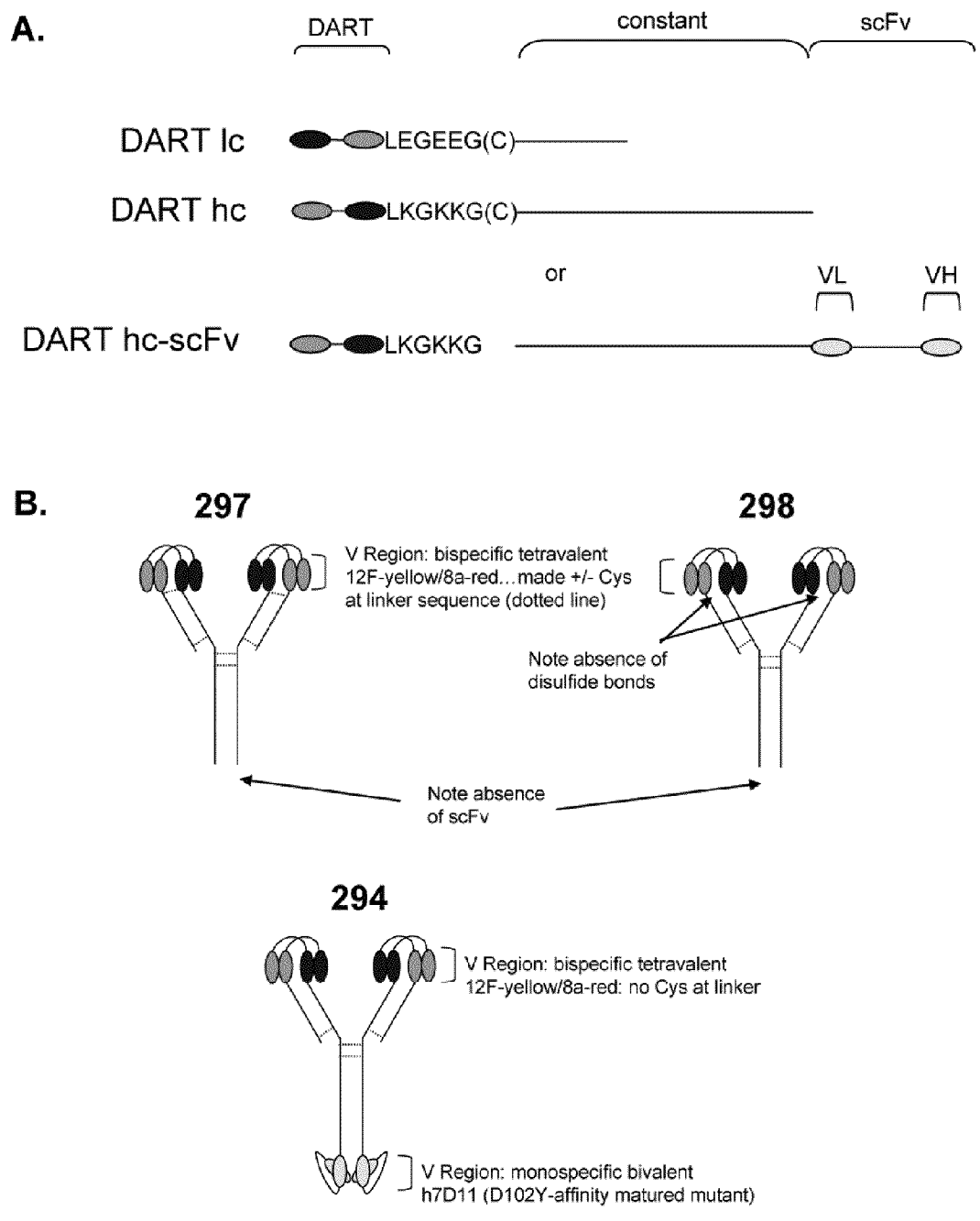

FIG. 32 (Panels A-B) illustrates the structures of exemplary IgDARTS. Panel A is a schematic depicting different types of linker sequences utilized in constructing Ch12F: Ch8A IgDARTs. Panel B: 12F/8a N-term IgDART with and without C-term h7D11 scFv. The left-hand constructs (297 and 298) below were made+/−Cys at the DART-Ig junction. The right hand construct (294) was made only in the absence of Cys.

FIG. 33 (Panels A-C) illustrates binding analyses (ELISAs) conducted using IgDARTS. ELISA assays were performed with IgDARTs to demonstrate binding to L1R (Panel A), A33R (Panel B) and B5R (Panel C). Results show that moving the epitope binding sites of the DARTS did not affect binding ability (i.e., full activity was retained).

FIG. 34 (Panels A-C) illustrates binding analyses (ELISAs) conducted using IgDARTS. ELISA assays were performed with IgDARTs to demonstrate binding to L1R and IgG (Panel A), A33R and IgG (Panel B) and A33R and L1R (Panel C).

DETAILED DESCRIPTION OF THE INVENTION

The present invention relates to improved compositions for the prevention and treatment of smallpox, and in particular to the use of compositions containing an antibody that binds to an epitope found on the MV form of the smallpox virus and an antibody that binds to an epitope found on the EV form of the smallpox virus. The invention relates to such compositions, especially to non-blood derived antibody compositions, such as chimeric or humanized antibodies, and to methods for their use in imparting passive immunity against smallpox infection to individuals at risk of smallpox virus infection or who exhibit smallpox.

As discussed above, blood-derived γ-immunoglobulin products, such as VIG and VIGIV, have inherent deficiencies, are variable in activity and are limited in supply. A stable, chemically defined, humanized monoclonal antibody (mAb) product would thus be preferable, particularly because monoclonal antibody preparations would be expected to be more concentrated in neutralizing activity and therefore more potent. Indeed, as discussed below, high affinity anti-vaccinia mAbs are significantly more protective than VIG in vaccinia virus challenge studies in mice (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995.

I. The Infectious Forms of the Smallpox Virus

Orthopoxviruses, such as smallpox, produce two primary infectious forms: intracellular mature virions (MV) and extracellular enveloped virions (EV). MV particles have a single membrane, are released after cell lysis, are relatively stable in the environment, represent the majority of infectious particles and play a predominant role in host-to-host transmission. By contrast, EV particles have an additional outer membrane, are released from infected cells, are unstable in the environment, but are responsible for direct cell-to-cell and long-range virus spread within a host (Moss, B. (2001) "*Poxviridae: The Viruses And Their Replication*," In: FIELDS VIROLOGY (4th Ed.) Fields, B. N. et al., Eds., Lippincott Williams & Wilkens, Publishers, Philadelphia; pp 2849-2883; Fogg, C. et al. (2004) "*Protective Immunity To Vaccinia Virus Induced By Vaccination With Multiple Recombinant Outer Membrane Proteins Of Intracellular And Extracellular Virions*," J. Virol. 78(19):10230-10237).

Vaccinia virus preparations consist mainly of MV particles. Because live vaccinia virus vaccines replicate following immunization, they produce MV and EV particles, elicit neutralizing immune responses to both forms, which induces protective immunity. By contrast, immunizations with inactivated, non-replicating vaccinia virus vaccines produce neutralizing antibodies against MV but not against EV, and thus fail to induce protective immunity (Appleyard, G. et al. (1974) "*Neutralizing Activities Of Antisera To Poxvirus Soluble Antigens,*" J. Gen. Virol. 23(2):197-200; Turner, G. S. et al. (1971) "*Inactivated Smallpox Vaccine: Immunogenicity Of Inactivated Intracellular And Extracellular Vaccinia Virus,*" J. Gen. Virol. 13(1):19-25).

In individuals vaccinated against smallpox with live vaccinia virus, there is a positive correlation between antibody titer and resistance to infection (Downie, A. W. et al. (1958) "*The Antibody Response In Man Following Infection With Viruses Of The Pox Group. III. Antibody Response In Smallpox,*" J. Hyg. (Lond) 56(4):479-487; Mack, T. M. et al. (1972) "*A Prospective Study Of Serum Antibody And Protection Against Smallpox,*" Amer. J. Trop. Med. Hyg. 21(2):214-218; Sarkar, J. K. et al. (1978) "*The Minimum Protective Level Of Antibodies In Smallpox,*" Bull. Who. 52:307-311) and levels of virus neutralizing antibodies are maintained for many years. In fact, serum levels of antibodies that neutralize the MV form of vaccinia virus remain relatively constant for up to 75 years post-vaccination (Hammarlund, E. et al. (2003) "*Duration Of Antiviral Immunity After Smallpox Vaccination*," Nat. Med. 9(9):1131-1137), whereas levels of antibodies that neutralize EV decline after 20 years post-vaccination (Viner, K. M. et al. (2005) "*Activity Of Vaccinia Virus-Neutralizing Antibody In The Sera Of Smallpox Vaccines*," Microbes Infect. 7(4):579-583). An analysis of 1,163 cases from the 1902-1903 smallpox outbreak in Liverpool, England revealed that individuals vaccinated more than 20 years previously developed more severe disease and deaths than ones vaccinated within the previous 10-20 years (Hanna, W. et al. (2002) "*Studies in Smallpox and Vaccination* 1913," Rev. Med. Virol. 12(4):201-209). The gradual loss of EV-neutralizing capacity in human serum over time correlates with the reduced protection observed in these historical studies (Viner, K. M. et al. (2005) "*Activity Of Vaccinia Virus-Neutralizing Antibody In The Sera Of Smallpox Vaccines*," Microbes Infect. 7(4):579-583). The data suggest that protection from smallpox infection may be restored if neutralizing EV antibody levels can be reestablished.

II. Preferred Compositions of the Present Invention

The compositions of the present invention preferably comprise non-blood derived, antibodies that immunospecifically bind to epitopes of the smallpox virus. Preferably, such compositions will comprise both antibodies that bind to epitopes found on the MV form of the smallpox virus and antibodies that bind to epitopes on the EV form of the smallpox virus. As used herein, the terms "immunospecifically binds," refers to the specificity of binding that characterizes the specific interaction between an antibody and an antigen (e.g., to an epitope or immune complex). An antibody that immunospecifically binds to an antigen may bind to other peptides or polypeptides with lower affinity as determined by, e.g., immunoassays, BIAcore, or other assays known in the art. Preferably, molecules that specifically bind an antigen do not cross-react with other proteins. Molecules that specifically bind an antigen can be identified, for example, by immunoassays, BIAcore, or other techniques known to those of skill in the art.

As used herein, the term "epitope" refers to a fragment of a polypeptide or protein or a non-protein molecule having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "antibody" refers to monoclonal antibodies, multispecific antibodies, human antibodies, humanized antibodies, synthetic antibodies, chimeric antibodies, polyclonal antibodies, camelized antibodies, single-chain Fvs (scFv), single chain antibodies, Fab fragments, F(ab') fragments, disulfide-linked bispecific Fvs (sdFv), intrabodies, and diabodies, including diabodies that are dual affinity retargeting reagents ("DARTs"). As used herein, "DARTS" are diabody molecules comprising a first and a second polypeptide chain. The first DART polypeptide chain comprises:

(A) a domain (I) comprising a binding region of a light chain variable domain of a first immunoglobulin (VL1) specific for a first epitope;

(B) a domain (II) comprising a binding region of a heavy chain variable domain of a second immunoglobulin (VH2) specific for a second epitope; and optionally, (C) a domain (III) comprising: an Fc domain or portion thereof, and/or a hinge region;

wherein domains (I) and (II) are covalently linked to one another such that they do not associate to form an epitope binding site, and optionally, domain (III) is N-terminal to both domain (I) and domain (II);

The second DART polypeptide comprises:

(A) a domain (IV) comprising a binding region of a light chain variable domain of the second immunoglobulin (VL2);

(B) a domain (V) comprising a binding region of a heavy chain variable domain of the first immunoglobulin (VH1); and optionally, (C) a domain (VI) comprising an Fc domain or at least the C-terminal 2 to 8 amino acid residues of a human light chain constant domain;

wherein domains (IV) and (V) are covalently linked to one another such that they do not associate to form an epitope binding site.

Domains (I) and (V) of the DART associate with one another to form a first binding site (VL1)(VH1), which binds the first epitope; and domains (II) and (IV) associate with one another to form a second binding site (VL2)(VH2), which binds the second epitope. "DARTS" may monospecific, bispecific, trispecific, etc., thus being able to simultaneously bind one, two, three or more different epitopes (which may be of the same or of different antigens). "DARTS" may additionally be monovalent, bivalent, trivalent, tetravalent, pentavalent, hexavelent, etc., thus being able to simultaneously bind one, two, three, four, five, six or more molecules.

In particular, the antibodies of the present invention include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$, and $IgA_2$) or subclass (see, e.g., United States Patent Publication Nos.: 20040185045; 20050037000; 20050064514; 20050215767; 20070004909; 20070036799; 20070077246; and 20070244303). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

As used herein, the term "non-blood derived" antibodies is intended to denote that the antibodies are produced or obtained from a source other than mammalian plasma. The non-blood derived antibodies of the present invention may thus be obtained, for example, synthetically (see, e.g., Dawson, P. E. et al. (2000) "*Synthesis Of Native Proteins By Chemical Ligation,*" Ann. Rev Biochem. 69:923-960; Wilken, J. et al. (1998) "*Chemical Protein Synthesis,*" Curr. Opin. Biotechnol. 9(4):412-426; Kochendoerfer, G. G. et al. (1999) "*Chemical Protein Synthesis,*" Curr. Opin. Chem. Biol. 3(6): 665-671), recombinantly or transgenically (Wang, M. et al. (2007) "*The Rapid Discovery Of Engineered Antibodies,*" IDrugs 10(8):562-565; Aubrey, N. et al. (2006) "*Recombinant Antibodies: Towards A New Generation Of Antivenoms?*" J. Soc. Biol. 200(4):345-354; Laffly, E., et al. (2006) "*Monoclonal Antibodies, 30 Years Of Success*" J. Soc. Biol. 200(4):325-343; Hagemeyer, C. E. et al. (2007) "*Single-Chain Antibodies As New Antithrombotic Drugs,*" Semin. Thromb. Hemost. 33(2):185-195; Rasmussen, S. K. et al. (2007) "*Manufacture Of Recombinant Polyclonal Antibodies,*" Biotechnol. Lett. 29(6):845-852; Gasser, B. et al. (2007) "*Antibody Production With Yeasts And Filamentous Fungi: On The Road To Large Scale?*" Biotechnol. Lett. 29(2):201-212; Jefferis, R. (2005) "*Glycosylation Of Recombinant Antibody Therapeutics,*" Biotechnol Prog. 21(1):11-16; Smith, K. A. et al. (2004) "*Demystified . . . . Recombinant Antibodies,*" J. Clin. Pathol. 57(9):912-917; Kipriyanov, S. M. et al. (2004) "*Generation And Production Of Engineered Antibodies,*" Mol. Biotechnol. 26(1):39-60; Fischer, R. et al. (2003) "*Production Of Antibodies In Plants And Their Use For Global Health,*" Vaccine 21(7-8):820-825; Maynard, J. et al. (2000) "*Antibody Engineering,*" Ann. Rev. Biomed. Eng. 2:339-376; Young, M. W. et al. (1998) "*Production Of Recombinant Antibodies In The Milk Of Transgenic Animals,*" Res. Immunol. 149(6):609-610; Hudson, P. J. (1998) "*Recombinant Antibody Fragments,*" Curr. Opin. Biotechnol. 9(4):395-402), via cell (e.g., hybridoma) culture (Laffly, E., et al. (2006) "*Monoclonal Antibodies, 30 Years Of Success*" J. Soc. Biol. 200(4):325-343; Aldington, S. et al. (2007) "*Scale-Up Of Monoclonal Antibody Purification Processes,*" J. Chromatogr. B Analyt. Technol. Biomed. Life Sci. 848(1): 64-78; Farid, S. S. (2006) "*Process Economics Of Industrial Monoclonal Antibody Manufacture,*" J. Chromatogr. B Analyt. Technol. Biomed. Life Sci. 848(1):8-18; Birch, J. R. et al. (2006) "*Antibody Production,*" Adv. Drug Deliv. Rev. 58(5-6):671-685; Even, M. S. et al. (2006) "*Serum-Free Hybridoma Culture: Ethical, Scientific And Safety Considerations,*" Trends Biotechnol. 24(3):105-108; Graumann, K. et al. (2006) "*Manufacturing Of Recombinant Therapeutic Proteins In Microbial Systems,*" Biotechnol. J. 1(2):164-186; U.S. Pat. No. 7,112,439; United States Patent Publications Nos. 20070037216 and 20040197866), or by other means.

In more preferred embodiments, the compositions of the present invention comprise a mixture of an anti-MV neutralizing mAb and an anti-EV neutralizing mAb. The anti-MV and anti-EV mAbs are mixed in a ratio by weight, which ratio may be, for example, 50:1, 25:1; 10:1, 5:1, 2:1; 1:1, 1:2, 1:5, 1:10, 1:25 or 1:50. A ratio of 1:1 is preferred.

Animal studies show that good protection from orthopoxvirus infection requires anti-EV and anti-MV immune responses. DNA immunization studies show that a mixture of four plasmids (two encoding MV proteins L1 and A27; two encoding EV proteins B5 and A33) protected mice against challenge with vaccinia virus better than immunization with any individual plasmid (Hooper, J. W. et al. (2003) "*Four-Gene-Combination DNA Vaccine Protects Mice Against A Lethal Vaccinia Virus Challenge And Elicits Appropriate Antibody Responses In Nonhuman Primates,*" Virology 306 (1):181-195). This "4pox DNA vaccine" also protected rhesus macaques from lethal monkeypox infection, whereas animals vaccinated with a single gene developed severe disease (Hooper, J. W. et al. (U.S. Pat. No. 6,451,309). Similarly, animals vaccinated with mixtures of MV and EV recombinant proteins (e.g., A33:B5:L1 or A33:L1) were more highly protected than those immunized with single proteins or combinations of just MV (or just EV) proteins (Fogg, C. et al. (2004) "*Protective Immunity To Vaccinia Virus Induced By Vaccination With Multiple Recombinant Outer Membrane Proteins Of Intracellular And Extracellular Virions,*" J. Virol. 78(19):10230-10237). Finally, VIG preparations with EV and MV antibodies were more protective in mice than preparations depleted in EV antibodies (Law, M. et al. (2005) "*An Investigation Of The Therapeutic Value Of Vaccinia-Immune IgG In A Mouse Pneumonia Model,*" J. Gen. Virol. 86(Pt 4):991-1000). The consistent feature of all of these studies was the superiority of treatments that contained or induced antibody responses that were MV- and EV-specific.

Without intending to be bound by any mechanism of action, in vitro studies provide insights into a possible mechanism of virus neutralization by combinations of MV- and EV-specific antibodies. Studies have showed that a combination of EV and MV antibodies (anti-A33+anti-L1) act synergistically in the presence of complement to neutralize vaccinia virus (Lustig, S. et al. (2004) "*Synergistic Neutralizing Activities Of Antibodies To Outer Membrane Proteins Of The Two Infectious Forms Of Vaccinia Virus In The Presence Of Complement,*" Virology 328(1):30-35). This data support a model in which complement plus an anti-EV antibody causes lysis of EV membranes, which releases MV particles, which are then neutralized by the anti-MV antibody.

Preferred Anti-MV Antibody.

In a first preferred embodiment, the anti-MV mAb will be the chimeric version of murine antibody 7D11 designated "Ch7D11," and more preferably still, the humanized form of this antibody designated "h7D 11." Antibody h7D11 is a humanized IgG1κ monoclonal antibody directed to an epitope in the L1 protein, a myristoylated transmembrane viral protein that is expressed on the surface of the MV (mature virion) form of vaccinia and other orthopox viruses. Antibody h7D11 is preferably produced through recombinant technology. Antibody h7D11 is composed of two heavy (H) chains and two light (L) chains and has a calculated molecular weight of ~150,000 Daltons. The H and L chain complementarity determining regions (CDRs) are of murine origin and the framework and constant regions are of human origin, resulting in an antibody with 90.27% human and 9.73% murine sequences. The sequences of the variable regions (VL; light chain variable region; HL heavy chain variable region) of antibodies 7D11 (murine) and h7D11 (humanized) are provided below along with the full light and heavy chains of antibody h7D11 (humanized):

SEQ ID NO: 1 (Murine 7D11 VL)
gacatggtga tgtcacagtc tccatcctcc ctggctgtgt
cagcaggaga gaaggtcagt atgagctgca aatccagtca
gactctgctc aacagtagaa cccgaaagaa ctacttggct
tggtaccagc agaaaccagg gcagtctcct aaaactactga
tctactggga tccactagg gaatctgggg tccctgatcg
cttcacaggc agtggatctg gacagattt cactctcacc
atcagcagtg tgcaggctga agacctggca gtttattact
gcaagcaatc ttataatctg tggacgttcg gtggaggcac
caagctggaa atcaaa SEQ ID NO: 2 (Murine 7D11 VL, encoded protein)
DMVMSQSPSS LAVSAGEKVS MSCKSSQTLL NSRTRKNYLA
WYQQKPGQSP KLLIYWASTR ESGVPDRFTG SGSGTDFTLT
ISSVQAEDLA VYYCKQSYNL WTFGGGTKLE IK SEQ ID NO: 3 (Murine 7D11 VH)
caggtccagc ttcagcagtc tggggctgaa ctggcaaaac
ctggggcctc agtgaagatg tcctgcaagg cttctggcta
cacctttact aggtactgga tgcactgggt aaaacagagg
cctggacagg gtctggaatg gattggatac attaatccta
gcactggtta tactgagtac aatcagaaat tcaaggacaa
ggccacattg actgcggaca atcctccag cacagtctac
atgcaactga gcagcctgac atctgaggac tctgcagtct
attactgtgc aagaactaca gtggatggtt acgactttgc
ttactggggc caagggactc tggtcactgt
ctcggca SEQ ID NO: 4 (Murine 7D11 VH, encoded protein)
QVQLQQSGAE LAKPGASVKM SCKASGYTFT RYWMHWVKQR
PGQGLEWIGY INPSTGYTEY NQKFKDKATL TADKSSSTVY
MQLSSLTSED SAVYYCARTT VDGYDFAYWG QGTLVTVSA SEQ ID NO: 5 (h7D11 VL)
gacatcgtga tgacccaatc tccagactct ttggctgtgt
ctctagggga gagggccacc atcaactgca aatccagtca
gactctgctc aacagtagaa cccgaaagaa ctacttggct
tggtaccaac agaaaccagg acagccaccc aaactcctca
tctactgggc atccactagg gaatctgggg tcccagacag
gtttagtggc agtgggtctg ggacagactt cacccctcacc
atcagcagcc tgcaggctga ggatgtggca gtttattact gcaagcaatc ttataatctg tggacgttcg gacaagggac
caagcttgag atcaaa SEQ ID NO: 6 (h7D11 VL, encoded protein)
DIVMTQSPDS LAVSLGERAT INCKSSQTLL NSRTRKNYLA
WYQQKPGQPP KLLIYWASTR ESGVPDRFSG SGSGTDFTLT
ISSLQAEDVA VYYCKQSYNL WTFGQGTKLE IK SEQ ID NO: 7 (h7D11 Light Chain)
gacatcgtga tgacccaatc tccagactct ttggctgtgt
ctctagggga gagggccacc atcaactgca aatccagtca
gactctgctc aacagtagaa cccgaaagaa ctacttggct
tggtaccaac agaaaccagg acagccaccc aaactcctca
tctactgggc atccactagg gaatctgggg tcccagacag
gtttagtggc agtgggtctg ggacagactt cacccctcacc
atcagcagcc tgcaggctga ggatgtggca gtttattact
gcaagcaatc ttataatctg tggacgttcg gacaagggac
caagcttgag atcaaagtcc tcggtcagcc caaggccaac
cccacagtca cctgttccc gcctcctct gaggagcttc
aagccaacaa ggccacactg gtgtgtctca taagtgactt
ctacccggga gccgtgacag tggcctggaa ggcagatggc
agccccgtca aggcgggagt ggagaccacc acacctcca
aacaaagcaa caacaagtac gcggccagca gctacctgag
cctgacgccc gagcagtgga agtcccacag aagctacagc
tgccaggtca cgcatgaagg gagcaccgtg gagaagacag
tggcccctac agaatgtt SEQ ID NO: 8 (h7D11 Light Chain, encoded protein)
DIVMTQSPDS LAVSLGERAT INCKSSQTLL NSRTRKNYLA
WASTRESGVP DRFSGSGSGT DFTLTISSLQ AEDVAVYYCK
QSYNLWTFGQ GTKLEIKRTV AAPSVFIFPP SDEQLKSGTA
SVVCLLNNFY PREAKVQWKV DNALQSGNSQ ESVTEQDSKD
STYSLSSTLT LSKADYEKHK VYACEVTHQG LSSPVTKSFN RGEC SEQ ID NO: 9 (h7D11 VH)
caggttcagc tggtgcagtc tggagctgag gtgaagaagc
ctggggcctc agtgaaggtc tcctgcaagg cttctggtta
cacctttacc cggtactgga tgcactgggt gcgacaggcc
cctggacaag gcttgagtg gatgggatac attaatccta
gcactggtta tactgagtac aatcagaaat tcaaggacag
agtcacgatt accgcggaca atcaacgag cacagcctac
atggagctga ggagcctgag atctgacgac acggccgtgt
attactgtgc gagaactaca gtggatggtt acgactttgc
ttactggggc caaggaaccc tggtcaccgt ctcctca -continued
SEQ ID NO: 10 (h7D11 VH)
QVQLVQSGAE VKKPGASVKV SCKASGYTFT RYWMHWVKQA

PGQGLEWMGY INPSTGYTEY NQKFKDRVTI TADKSTSTAY

MELRSLRSDD TAVYYCARTT VDGYDFAYWG QGTLVTVSS

SEQ ID NO: 11 (h7D11 Heavy Chain)
caggttcagc tggtgcagtc tggagctgag gtgaagaagc ctggggcctc agtgaaggtc tcctgcaagg cttctggtta cacctttacc cggtactgga tgcactgggt gcgacaggcc cctggacaag ggcttgagtg gatgggatac attaatccta gcactggtta tactgagtac aatcagaaat tcaaggacag agtcacgatt accgcggaca atcaacgag cacagcctac atggagctga ggagcctgag atctgacgac acggccgtgt attactgtgc gagaactaca gtggatggtt acgactttgc ttactggggc caaggaaccc tggtcaccgt ctcctcagcc tccaccaagg gcccatcggt cttcccctg gcacctcct ccaagagcac ctctggggc acagcggcc tgggctgcct ggtcaaggac tacttccccg aaccggtgac ggtgtcgtgg aactcaggcg ccctgaccag cggcgtgcac accttcccgg ctgtcctaca gtcctcagga ctctactccc tcagcagcgt ggtgaccgtg ccctccagca gcttgggcac ccagacctac atctgcaacg tgaatcacaa gcccagcaac accaaggtgg acaagagagt tgagcccaaa tcttgtgaca aaactcacac atgcccaccg tgcccagcac ctgaactcct gggggaccg tcagtcttcc tcttccccc aaacccaag gacaccctca tgatctcccg gaccctgag gtcacatgcg tggtggtgga cgtgagccac gaagaccctg aggtcaagtt caactggtac gtggacggcg tggaggtgca taatgccaag acaaagccgc gggaggagca gtacaacagc acgtaccgtg tggtcagcgt cctcaccgtc ctgcaccagg actggctgaa tggcaaggag tacaagtgca aggtctccaa caaagccctc ccagcccca tcgagaaaac catctccaaa gccaaagggc agccccgaga accacaggtg tacaccctgc ccccatcccg ggatgagctg accaagaacc aggtcagcct gacctgcctg gtcaaaggct tctatcccag cgacatcgcc gtggagtggg agagcaatgg gcagccggag aacaactaca agaccacgcc tcccgtgctg gactccgacg gctccttctt cctctacagc aagctcaccg tggacaagag caggtggcag caggggaacg tcttctcatg ctccgtgatg catgaggctc tgcacaacca ctacacgcag aagagcctct ccctgtctcc gggtaaatga SEQ ID NO: 12 (h7D11 Heavy Chain, encoded protein)
QVQLVQSGAE VKKPGASVKV SCKASGYTFT RYWMHWVKQA

PGQGLEWMGY INPSTGYTEY NQKFKDRVTI TADKSTSTAY

-continued
MELRSLRSDD TAVYYCARTT VDGYDFAYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPELLGGP

SVFLLPPKPK DTLMISRTPE VTCVVVDVSH EDPEVKFNWY

VDGVEVHNAK TKPPEEQYNS TLRVVSILTV LHQDWLNGKE

YKCKVSNKAL PAPIEKTISK AKGQPREPQV YTLPPSRDEL

TKNQVSLTCL VKGFYPSDIA VEWESNGQPE NNYKTTPLVL

DSDGSFFLYS KLTVDKSRWQ QGNVFSCSVM HEALHNHYTQ

KSLSLSPGK

Antibody h7D11 immunospecifically binds the L1 viral protein with moderate affinity (KD of 3.6×10-8 M). 7D11 (the murine parent to h7D11; U.S. Pat. No. 6,562,376) has been shown to bind to a conformational epitope of 12 residues that is positioned at the ends of loops of the ectodomain of the L1 protein (Su, H. P. et al. (2007) "*Structural Basis For The Binding Of The Neutralizing Antibody, 7D11, To The Poxvirus L1 Protein*," Virology 368(2):331-341). The contact residues (underlined) of the non-linear epitope identified by antibody 7D11 and h7D11 is located within three non-contiguous domains of L1 (SEQ ID NOS:13-15):

SEQ ID NO: 13: EA<u>N</u>A<u>SAQTKC</u> <u>D</u>IE  (L1 residues 23-37)

SEQ ID NO: 14: MC<u>SADADAQ</u>       (L1 residues 55-63)

SEQ ID NO: 15: DN<u>KLKI</u>Q         (L1 residues 140-146)

The sequence of the 12-contact residues of the epitope and their adjacent sequences are completely conserved in all orthopox viruses. Thus, antibody that immunospecifically binds to this epitope will be capable of neutralizing all orthopox virus species. Antibody 7D11 has been shown to neutralize variola virus in vitro and a mixture of Ch7D11 and as shown below, anti-EV mAbs neutralized ectromelia virus in vivo. The mechanism of virus neutralization is not understood, but neutralizing activity is retained even when the antibody is added after virus adsorption to cells (Su, H. P. et al. (2007) "*Structural Basis For The Binding Of The Neutralizing Antibody, 7D11, To The Poxvirus L1 Protein*," Virology 368(2):331-341).

Preferred Anti-EV Antibody.

In preferred embodiments, the anti-EV antibody will be a Ch6C, Ch12F, or Ch8AH8AL mAb. Most preferably, the anti-EV mAb will be Ch12F. Because chimpanzee and human VH and L chain sequences are virtually identical (Schofield, D. J. et al. (2002) "*Four Chimpanzee Monoclonal Antibodies Isolated By Phage Display Neutralize Hepatitis A Virus*," Virology 292(1):127-136; Ehrlich, P. H. et al. (1990) "*Potential Of Primate Monoclonal Antibodies To Substitute For Human Antibodies: Nucleotide Sequence Of Chimpanzee Fab Fragments*," Hum. Antibodies Hybridomas 1(1):23-26), humanization of the chimpanzee portion of Ch12F is not necessary. The methods used to isolate these antibodies and detailed descriptions of their properties have been published (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Mono-* clonal Antibodies To Vaccinia Virus A33 Glycoprotein And Its Variola Virus Homolog In Vitro And In A Vaccinia Virus Mouse Protection Model," J. Virol. 81(17):8989-8995).

The sequences of the variable regions (VL; light chain variable region; HL heavy chain variable region) and the full light and heavy chains of antibody Ch6C are provided below:

SEQ ID NO: 16 (ch6C VL):
gagctcgtgt tgacgcagcc gccctcagtg tctgcggccc caggacagaa gatcactatt tcctgctctg gaagcggctc caacattggg aggcattatg tatcctggta ccaacaattc ccaggaacag cccccaaaat cctcatttat gacaatgata agcgaccctc agggatttcc gaccgattct ctggctccaa gtctggcgcg tcagccaccc tggacatcac cggactccag actggggacg aggccgatta ttactgcgca acatgggata ccaacttgag tggtggggtg ttcggcggag ggactaaagt gacc SEQ ID NO: 17 (ch6C VL; encoded protein):
ELVLTQPPSV SAAPGQKITI SCSGSGSNIG RHYVSWYQQF

PGTAPKILIY DNDKRPSGIS DRFSGSKSGA SATLDITGLQ

TGDEADYYCA TWDTNLSGGV FGGGTKVT

SEQ ID NO: 18 (ch6C Light chain):
gagctcgtgt tgacgcagcc gccctcagtg tctgcggccc caggacagaa gatcactatt tcctgctctg gaagcggctc caacattggg aggcattatg tatcctggta ccaacaattc ccaggaacag cccccaaaat cctcatttat gacaatgata agcgaccctc agggatttcc gaccgattct ctggctccaa gtctggcgcg tcagccaccc tggacatcac cggactccag actggggacg aggccgatta ttactgcgca acatgggata ccaacttgag tggtggggtg ttcggcggag ggactaaagt gaccgtccta ggtcagccca aggctgcccc ctcggtcact ctgttcccgc cctcctctga ggagcttcaa gccaacaagg ccacactggt gtgtctcata agtgacttct acccgggagc cgtgacagtg gcctggaagg cagatagcag ccccgtcaag gcgggagtgg agaccaccac accctccaaa caaagcaaca acaagtacgc ggcagcagc tacctgagcc tgacgcccga gcagtggaag tcccacaaaa gctacagctg ccaggtcacg catgaaggga gcaccgtgga agacagtg gcccctacag aatgtt SEQ ID NO: 19 (ch6C Light chain, encoded protein):
ELVLTQPPSV SAAPGQKITI SCSGSGSNIG RHYVSWYQQF

PGTAPKILIY DNDKRPSGIS DRFSGSKSGA SATLDITGLQ

TGDEADYYCA TWDTNLSGGV FGGGTKVTVL GQPKAAPSVT

LFPPSSEELQ ANKATLVCLI SDFYPGAVTV AWKADSSPVK

AGVETTTPSK QSNNKYAASS YLSLTPEQWK SHKSYSCQVT

HEGSTVEKTV APTEC

SEQ ID NO: 20 (ch6C VH):
caggtgcagc tggtgcagtc tgggtctgag gtgaagaagc ctggggcctc agtgaagctt tcctgcaagg cttctggata cacattcact agctactctt tgggctgggt gcgacaggcc cctggacaag gacttgagtg gatgggatgg atcaacacca agactggaaa cccaacttat gcccagggct tcacaggacg gtttgtcttc tccttggaca cgtctgtcaa cacggcatat ctgcagatca ccagcctaaa ggctgaggac actgccgtat atttctgtgc gaaaggaaca ttttactatg gttggggtcc ttactataat tggttcgacc cctggggcca gggagccctg gtcaccgtct cctca SEQ ID NO: 21 (ch6C VH, encoded protein):
QVQLVQSGSE VKKPGASVKL SCKASGYTFT SYSLGWVRQA

PGQGLEWMGW INTKTGNPTY AQGFTGRFVF SLDTSVNTAY

LQITSLKAED TAVYFCAKGT FYYGWGPYYN WFDPWGQGAL VTVSS

SEQ ID NO: 22 (ch6C Heavy Chain):
caggtgcagc tggtgcagtc tgggtctgag gtgaagaagc ctggggcctc agtgaagctt tcctgcaagg cttctggata cacattcact agctactctt tgggctgggt gcgacaggcc cctggacaag gacttgagtg gatgggatgg atcaacacca agactggaaa cccaacttat gcccagggct tcacaggacg gtttgtcttc tccttggaca cgtctgtcaa cacggcatat ctgcagatca ccagcctaaa ggctgaggac actgccgtat atttctgtgc gaaaggaaca ttttactatg gttggggtcc ttactataat tggttcgacc cctggggcca gggagccctg gtcaccgtct cctcagcctc caccaagggc ccatcggtct tccccctggc accctcctcc aagagcacct ctgggggcac agcggccctg ggctgcctgg tcaaggacta cttccccgaa ccggtgacgg tgtcgtggaa ctcaggcgcc ctgaccagcg gcgtgcacac cttcccggct gtcctacagt cctcaggact ctactccctc agcagcgtgg tgaccgtgcc ctccagcagc ttgggcaccc agacctacat ctgcaacgtg aatcacaagc ccagcaacac caaggtggac aagagagttg agcccaaatc ttgtgacaaa actcacacat gcccaccgtg cccagcacct gaactcctgg ggggaccgtc agtcttcctc ttccccccaa aacccaagga caccctcatg atctcccgga cccctgaggt cacatgcgtg gtggtggacg tgagccacga agaccctgag gtcaagttca actggtacgt ggacggcgtg gaggtgcata atgccaagac aaagccgcgg gaggagcagt acaacagcac gtaccgtgtg gtcagcgtcc tcaccgtcct gcaccaggac tggctgaatg gcaaggagta caagtgcaag gtctccaaca aagccctccc agcccccatc gagaaaacca tctccaaagc

```
caaagggcag ccccgagaac cacaggtgta caccctgccc ccatcccggg atgagctgac caagaaccag gtcagcctga cctgcctggt caaaggcttc tatcccagcg acatcgccgt ggagtgggag agcaatgggc agccggagaa caactacaag accacgcctc ccgtgctgga ctccgacggc tccttcttcc tctacagcaa gctcaccgtg gacaagagca ggtggcagca ggggaacgtc ttctcatgct ccgtgatgca tgaggctctg cacaaccact acacgcagaa gagcctctcc ctgtctccgg gtaaatga
```

SEQ ID NO: 23 (ch6C Heavy Chain, encoded protein):
QVQLVQSGSE VKKPGASVKL SCKASGYTFT SYSLGWVRQA

PGQGLEWMGW INTKTGNPTY AQGFTGRFVF SLDTSVNTAY

LQITSLKAED TAVYFCAKGT FYYGWGPYYN WFDPWGQGAL

VTVSSASTKG PSVFPLAPSS KSTSGGTAAL GCLVKDYFPE

PVTVSWNSGA LTSGVHTFPA VLQSSGLYSL SSVVTVPSSS

LGTQTYICNV NHKPSNTKVD KRVEPKSCDK THTCPPCPAP

ELLGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK

The sequences of the variable regions (VL; light chain variable region; HL heavy chain variable region) and the full light and heavy chains of antibody Ch12F are provided below:

SEQ ID NO: 24 (ch12F VL):
```
gagctcgccc tgactcagcc tgcctccgtg tctgggtctc ctggacagtc gatcaccatc tcctgcactg gaaccagcag tgatgttggt ggttataacg ctgtctcctg gtaccaacag cacccaggca agcccccaa actcatgatt tatgaggtca ataagcggcc ctcagggggtt tctaatcgct tctctggctc caagtctggc aacacggcct ccctgaccat ctctgggctc caggctgagg acgaggctga ttattactgc agctcatata gaagcggagg aactgtggta ttcggcggag ggaccaagct gacc
```

SEQ ID NO: 25 (ch12F VL, encoded protein):
ELALTQPASV SGSPGQSITI SCTGTSSDVG GYNAVSWYQQ

HPGKAPKLMI YEVNKRPSGV SNRFSGSKSG NTASLTISGL

QAEDEADYYC SSYRSGGTVV FGGGTKLT

SEQ ID NO: 26 (ch12F Light chain):
```
gagctcgccc tgactcagcc tgcctccgtg tctgggtctc ctggacagtc gatcaccatc tcctgcactg gaaccagcag tgatgttggt ggttataacg ctgtctcctg gtaccaacag cacccaggca agcccccaa actcatgatt tatgaggtca ataagcggcc ctcagggggtt tctaatcgct tctctggctc caagtctggc aacacggcct ccctgaccat ctctgggctc caggctgagg acgaggctga ttattactgc agctcatata gaagcggagg aactgtggta ttcggcggag ggaccaagct gaccgtccta ggtcagccca aggctgcccc ctcggtcact ctgttcccgc cctcctctga ggagcttcaa gccaacaagg ccacactggt gtgtctcata agtgacttct acccgggagc cgtgacagtg gcctggaagg cagatagcag ccccgtcaag gcgggagtgg agaccaccac accctccaaa caaagcaaca acaagtacgc ggccagcagc tacctgagcc tgacgcccga gcagtggaag tcccacaaaa gctacagctg ccaggtcacg catgaaggga gcaccgtgga agacagtg gcccctacag aatgtt
```

SEQ ID NO: 27 (ch12F Light chain, encoded protein):
ELALTQPASV SGSPGQSITI SCTGTSSDVG GYNAVSWYQQ

HPGKAPKLMI YEVNKRPSGV SNRFSGSKSG NTASLTISGL

QAEDEADYYC SSYRSGGTVV FGGGTKLTVL GQPKAAPSVT

LFPPSSEELQ ANKATLVCLI SDFYPGAVTV AWKADSSPVK

AGVETTTPSK QSNNKYAASS YLSLTPEQWK SHKSYSCQVT

HEGSTVEKTV APTEC

SEQ ID NO: 28 (ch12F VH):
```
gaggtgcagc tggtgcagtc tggggcagag gtgaaaaagc ccggggagtc tctgaagata tcctgtaagg gctctggata cacctttgcc agctactgga tcgtctgggt gcgccagatg cccgggaaag gcctggagta catgggggagc atctatcctg gtgactctgg taccagatat agcccgtcct tccgaggcca ggtcaccatc tcagccgaca gtccatcaa caccgcctac ttgcagtggg gcagcctgaa ggcctcggac accgccttct actactgtgc gagacttaag ccccttcgtg ggtcgttatt cggggagcct attgggccct atgactactg gggccaggca accctggtca ccgtctcctc a
```

SEQ ID NO: 29 (ch12F VH, encoded protein):
EVQLLESGAE VKKPGESLKI SCKGSGYTFA SYWIVWVRQM

PGKGLEYMGS IYPGDSGTRY SPSFRGQVTI SADKSINTAY

LQWGSLKASD TAFYYCARLK PLRGSLFGEP IGPYDYWGQA

TLVTVSS

SEQ ID NO: 30 (ch12F Heavy Chain):
```
gaggtgcagc tggtgcagtc tggggcagag gtgaaaaagc ccggggagtc tctgaagata tcctgtaagg gctctggata
```

-continued
```
cacctttgcc agctactgga tcgtctgggt gcgccagatg cccgggaaag gcctggagta catggggagc atctatcctg gtgactctgg taccagatat agcccgtcct tccgaggcca ggtcaccatc tcagccgaca gtccatcaa caccgcctac ttgcagtggg gcagcctgaa ggcctcggac accgccttct actactgtgc gagacttaag ccccttcgtg ggtcgttatt cggggagcct attgggccct atgactactg gggccaggca accctggtca ccgtctcctc agcctccacc aagggcccat cggtcttccc cctggcaccc tcctccaaga gcacctctgg gggcacagcg gccctgggct gcctggtcaa ggactacttc cccgaaccgg tgacggtgtc gtggaactca ggcgccctga ccagcggcgt gcacaccttc ccggctgtcc tacagtcctc aggactctac tccctcagca gcgtggtgac cgtgccctcc agcagcttgg gcacccagac ctacatctgc aacgtgaatc acaagcccag caacaccaag gtggacaaga gagttgagcc caaatcttgt gacaaaactc acacatgccc accgtgccca gcacctgaac tcctggggg accgtcagtc ttcctcttcc ccccaaaacc caaggacacc ctcatgatct cccggacccc tgaggtcaca tgcgtggtgg tggacgtgag ccacgaagac cctgaggtca agttcaactg gtacgtggac ggcgtggagg tgcataatgc caagacaaag ccgcgggagg agcagtacaa cagcacgtac cgtgtggtca gcgtcctcac cgtcctgcac caggactggc tgaatggcaa ggagtacaag tgcaaggtct ccaacaaagc cctcccagcc cccatcgaga aaaccatctc caaagccaaa gggcagcccc gagaaccaca ggtgtacacc ctgcccccat cccgggatga gctgaccaag aaccaggtca gcctgacctg cctggtcaaa ggcttctatc ccagcgacat cgccgtggag tgggagagca atgggcagcc ggagaacaac tacaagacca cgcctcccgt gctggactcc gacggctcct tcttcctcta cagcaagctc accgtggaca gagcaggtg gcagcaggg aacgtcttct catgctccgt gatgcatgag gctctgcaca accactacac gcagaagagc ctctccctgt ctccgggtaa atga
```

SEQ ID NO: 31 (Ch12F Heavy Chain, encoded protein):
EVQLLESGAE VKKPGESLKI SCKGSGYTFA SYWIVWVRQM

PGKGLEYMGS IYPGDSGTRY SPSFRGQVTI SADKSINTAY

LQWGSLKASD TAFYYCARLK PLRGSLFGEP IGPYDWGQA

TLVTVSSAST KGPSVFPLAP SSKSTSGGTA ALGCLVKDYF

PEPVTVSWNS GALTSGVHTF PAVLQSSGLY SLSSVVTVPS

SSLGTQTYIC NVNHKPSNTK VDKRVEPKSC DKTHTCPPCP

APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSRDELTK NQVSLTCLVK GFYPSDIAVE WESNGQPENN

YKTTPPVLDS DGSFFLYSKL TVDKSRWQQG NVFSCSVMHE

ALHNHYTQKS LSLSPGK

The sequences of the variable regions (VL; light chain variable region; HL heavy chain variable region) and the full light and heavy chains of antibody ch8AH8AL are provided below:

SEQ ID NO: 32 (ch8AH8AL VL):
```
gagctcgccc tgactcagcc tgcctccgtg tctgggtctc ctggacagtc gatcaccatc tcctgcactg gaggcagaag tgaccttggt gattctaact ttgtctcctg gtaccaacaa tacccaggca aagcccccaa actcctgatt tatcaggtca ataagaggcc ctcaggggtc cctgatcgct tctctgcgtc caagtctgcc aacacggcct ccctgaccat ctctgggctc caaactgagg acgaggctga ctatttctgc agctcatata caaccaccag tacttatgtc ttcggaattg ggaccaaggt cgtc
```

SEQ ID NO: 33 (ch8AH8AL VL, encoded protein):
ELALTQPASV SGSPGQSITI SCTGGRSDLG DSNFVSWYQQ

YPGKAPKLLI YQVNKRPSGV PDRFSASKSA NTASLTISGL

QTEDEADYFC SSYTTTSTYV FGIGTKVV

SEQ ID NO: 34 (ch8AH8AL Light Chain):
```
gagctcgccc tgactcagcc tgcctccgtg tctgggtctc ctggacagtc gatcaccatc tcctgcactg gaggcagaag tgaccttggt gattctaact ttgtctcctg gtaccaacaa tacccaggca aagcccccaa actcctgatt tatcaggtca ataagaggcc ctcaggggtc cctgatcgct tctctgcgtc caagtctgcc aacacggcct ccctgaccat ctctgggctc caaactgagg acgaggctga ctatttctgc agctcatata caaccaccag tacttatgtc ttcggaattg ggaccaaggt cgtcgtcctc ggtcagccca aggccaaccc cacagtcacc ctgttcccgc cctcctctga ggagcttcaa gccaacaagg ccacactggt gtgtctcata agtgacttct acccgggagc cgtgacagtg gcctggaagg cagatgcag ccccgtcaag gcgggagtgg agaccaccac ccctccaaa caaagcaaca acaagtacgc ggccagcagc tacctgagcc tgacgcccga gcagtggaag tcccacagaa gctacagctg ccaggtcacg catgaaggga gcaccgtgga gaagacagtg gcccctacag aatgtt
```

SEQ ID NO: 35 (ch8AH8AL Light Chain, encoded protein):
ELALTQPASV SGSPGQSITI SCTGGRSDLG DSNFVSWYQQ

YPGKAPKLLI YQVNKRPSGV PDRFSASKSA NTASLTISGL

```
QTEDEADYFC SSYTTTSTYV FGIGTKVVVL GQPKANPTVT

LFPPSSEELQ ANKATLVCLI SDFYPGAVTV AWKADGSPVK

AGVETTTPSK QSNNKYAASS YLSLTPEQWK SHRSYSCQVT

HEGSTVEKTV APTECS

SEQ ID NO: 36 (ch8AH8AL VH):
gaggtgcagc tggtggagtc tggggaggc ttaataaagc ctgggggatc cctgagactc tcctgtgcag cctctggatt catctttagg gactataata tcaactgggt ccgccaggct ccagggaagg ggctggagtg gctaggtttc ataaggacca gagcttcagg ccggtcaaca gagtacagcg catctgtgaa aggcagattc actatctcaa gagatgattc caaaaacatt gcctatctac acatcaatag cctgaaaatg gaggacacag ccgtgtatta ttgtgctaag aaaggggaca gttactacta catggacttc tggggcaaag ggaccgcggt caccgtctcc tca SEQ ID NO: 37 (ch8AH8AL VH, encoded protein):
EVQLVESGGG LIKPGGSLRL SCAASGFIFR DYNINWVRQA

PGKGLEWLGF IRTRASGRST EYSASVKGRF TISRDDSKNI

AYLHINSLKM EDTAVYYCAK KGDSYYYMDF WGKGTAVTVS S

SEQ ID NO: 38 (ch8AH8AL Heavy Chain):
gaggtgcagc tggtggagtc tggggaggc ttaataaagc ctgggggatc cctgagactc tcctgtgcag cctctggatt catctttagg gactataata tcaactgggt ccgccaggct ccagggaagg ggctggagtg gctaggtttc ataaggacca gagcttcagg ccggtcaaca gagtacagcg catctgtgaa aggcagattc actatctcaa gagatgattc caaaaacatt gcctatctac acatcaatag cctgaaaatg gaggacacag ccgtgtatta ttgtgctaag aaaggggaca gttactacta catggacttc tggggcaaag ggaccgcggt caccgtctcc tcagcctcca ccaagggccc atcggtcttc ccctggcac cctcctccaa gagcacctct gggggcacag cggccctggg ctgcctggtc aaggactact tccccgaacc ggtgacggtg tcgtggaact caggcgccct gaccagcggc gtgcacacct tcccggctgt cctacagtcc tcaggactct actccctcag cagcgtggtg accgtgccct ccagcagctt gggcacccag acctacatct gcaacgtgaa tcacaagccc agcaacacca aggtggacaa gagagttgag cccaaatctt gtgacaaaac tcacacatgc ccaccgtgcc cagcacctga actcctgggg ggaccgtcag tcttcctctt ccccccaaaa cccaaggaca ccctcatgat ctcccggacc cctgaggtca catgcgtggt ggtggacgtg agccacgaag accctgaggt caagttcaac tggtacgtgg acggcgtgga ggtgcataat gccaagacaa agccgcggga ggagcagtac aacagcacgt accgtgtggt
```
cagcgtcctc accgtcctgc accaggactg gctgaatggc aaggagtaca agtgcaaggt ctccaacaaa gcctcccag ccccatcga gaaaaccatc tccaaagcca aagggcagcc ccgagaacca caggtgtaca ccctgccccc atcccgggat gagctgacca agaaccaggt cagcctgacc tgcctggtca aaggcttcta tcccagcgac atcgccgtgg agtgggagag caatgggcag ccggagaaca actacaagac cacgcctccc gtgctggact ccgacggctc cttcttcctc tacagcaagc tcaccgtgga caagagcagg tggcagcagg ggaacgtctt ctcatgctcc gtgatgcatg aggctctgca caaccactac acgcagaaga gcctctccct gtctccgggt aaatga SEQ ID NO: 39 (ch8AH8AL Heavy Chain, encoded protein):
EVQLVESGGG LIKPGGSLRL SCAASGFIFR DYNINWVRQA

PGKGLEWLGF IRTRASGRST EYSASVKGRF TISRDDSKNI

AYLHINSLKM EDTAVYYCAK KGDSYYYMDF WGKGTAVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKRVE PKSCDKTHTC PPCPAPELLG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRD

ELTKNQVSLT CLVKGFYPSD IAVEWESNGQ PENNYKTTPP

VLDSDGSFFL YSKLTVDKSR WQQGNVFSCS VMHEALHNHY

TQKSLSLSPG K

Antibody Ch12F is a chimeric chimpanzee/human IgG1κ monoclonal antibody. Antibody Ch12F is preferably produced through recombinant technology. Antibody ch12F is composed of two H chains and two L chains and has a calculated molecular weight of ~150,000 Daltons. The VH region and L chain are of chimpanzee origin and the H chain constant regions are of human origin, resulting in an antibody with 52% human and 48% chimpanzee sequences. Antibody Ch12F immunospecifically binds the A33 viral protein with high affinity (KD of $4.6 \times 10^{-10}$ M). A33 is required for EV formation and it participates in the actin-dependent process by which virus particles are released from the cell.

Both the Ch6C mAb and the Ch12F mAb bind immunospecifically to the A33 viral protein, a glycoprotein expressed on the surface of the EV (enveloped virion) form of vaccinia and other orthopox viruses. The epitope in the A33 viral protein recognized by Ch12F and Ch6C may be overlapping, since studies show that they compete for binding.

The specific epitope in A33 that is recognized by Ch12F has been found to be disulfide-dependent, and to comprise a conformational region located at the C-terminus of the protein. The epitope has been mapped between residues 99 and 185 (SEQ ID NO:40) (Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995)(see GenBank Accession No. P33850). The amino acid sequence of this region is highly conserved in all orthopox viruses, and it is therefore likely that Ch12F will have neutralizing activity against all orthopox viruses, (including variola virus and monkeypox virus). As shown below, a mixture of antibodies that included Ch12F neutralized ectromelia virus in vivo.

```
SEQ ID NO: 40:
SCNGLYYQGS CYILHSDYQL FSDAKANCTA ESSTLPNKSD

VLITWLIDYV EDTWGSDGNP ITKTTSDYQD SDVSQEVRKY

FCVKTMN
```

This epitope-containing region is highly conserved in orthopoxvirus species. The corresponding rabbitpox (RPXV) and horsepox (HPXV) epitopes do not differ from the recognized vaccinia A33 epitope. The corresponding cowpox (CPXV) differs from the recognized vaccinia A33 epitope only by substitutions: L112F and I141T. The corresponding camelpox (CMLV) differs from the recognized vaccinia A33 epitope only by substitutions: L112F, A128T and I141T. The corresponding monkeypox (MPXV) differs from the recognized vaccinia A33 epitope only by substitutions: Q117K, L118S, S120E, T127A and I141T. The corresponding ectromelia (ECTV) differs from the recognized vaccinia A33 epitope only by substitutions: Q117K, L118S, S120E, A128V, S131L, T132I, I141A, I145A, D146E, D165E, Q173R and T183I. The corresponding variola (VARV) differs from the recognized vaccinia A33 epitope only by substitutions: L112F, T127A, A128T, I141T and S164T. The corresponding taterapox (TATV) differs from the recognized vaccinia A33 epitope only by substitutions: S99N, L112F, A128T and I141T.

The ch8AH8AL mAb binds immunospecifically to the B5 viral protein. The epitope in the B5 viral protein recognized by ch8AH8AL has been mapped to residues 20-130 (SEQ ID NO:41), which corresponds to the SCR1 and SCR2 portions of the extracellular domain.

```
SEQ ID NO: 41:
TCTVPTMNNA KLTSTETSFN DKQKVTFTCD QGYHSSDPNA

VCETDKWKYE NPCKKMCTVS DYISELYNKP LYEVNSTMTL

SCNGETKYFR CEEKNGNTSW NDTVTCPNAE C
```

This epitope-containing region is also highly conserved in all orthopox virus species. The corresponding rabbitpox (RPXV) and horsepox (HPXV) epitopes differ from the recognized vaccinia B5 epitope only by substitutions of N for D at position 40 (i.e., D40N) and N for K at position 41 (i.e., K41N). The corresponding monkeypox (MPXV) epitope differs from the recognized vaccinia B5 epitope only by substitutions: Q50S, S55L, I82V, and N87D. The corresponding ectromelia (ECTV) epitope differs from the recognized vaccinia B5 epitope only by substitutions: Q42H, S55L, I82V, N87D, S100R and G103S. The corresponding cowpox (CPXV) epitope differs from the recognized vaccinia B5 epitope only by substitutions: Q50S, H52Y, S55L, K67T, I82V, N87D, S100T, N102K and G103D. The corresponding variola (VARV) epitope differs from the recognized vaccinia B5 epitope only by substitutions: Q50S, H52Y, S55L, I82V, S95A, T96I, M97I, S100T, N102K and G103D. The corresponding camelpox (CMLV) epitope differs from the recognized vaccinia B5 epitope only by substitutions: Q50S, H52Y, S55L, I82V, N87D, S95A, M97I, S100I, N102K, G103D and G115E. The corresponding taterapox (TATV) epitope differs from the recognized vaccinia B5 epitope only by substitutions: Q50S, H52Y, S55L, C61Y, I82V, N87D, S95A, M97I, S100I, N102K and G103D.

In a second preferred embodiment, the antibodies of the present invention are dual affinity retargeting reagents ("DARTs"). Preferably, such DARTS will comprise two covalently linked polypeptides in which each chain contains a VL and a VH that must interact with the VL and VH on the opposite chain to reconstitute a functional Fv (FIG. 13, FIG. 14). These molecules are stable for months under various pH and temperature conditions, and retain activity for over two weeks in human serum in vitro at 37° C. Such DARTS will preferably contain linker sequences of (SEQ ID NO:42) GGGSGGGG between each VL and VH. Further, they may contain C-terminal cysteines that are capable of forming disulfide bonds to covalently link the two chains, or they may lack such terminal cysteines. In some embodiments, the employed DARTs may contain Fc regions. If desired, specific versions of the Fc fragment can be selected to invoke specific immune function. For example, the native or mutated Fc region of a human IgG1 that enhances interactions with the cellular Fc receptor, FcRn may be employed. In adults, these interactions facilitate recycling of IgG molecules taken up through the endocytic pathway and further increase their serum halflife (Dall'Acqua, W. F. et al. (2002) "*Increasing The Affinity Of A Human Igg1 For The Neonatal Fc Receptor: Biological Consequences,*" J. Immunol. 2002 Nov. 1; 169(9):5171-80, Shields, R. L. et al. (2001) "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 276 (9):6591-6604).

As discussed below, pre- and post-exposure efficacy studies in vaccinia virus-infected mice have demonstrated that a mixture (cocktail) of an anti-MV mAb (Ch7D11 or h7D11) and an anti-EV mAb (Ch12F, Ch6C or Ch8A) has greater efficacy than any individual antibody. The data are consistent with the hypothesis that a combination of antibodies to MV and EV particles act synergistically in virus neutralization in vivo. Moreover, cocktails of anti-MV and anti-EV mAbs were found to be efficacious when administered at 3 days post infection, a time when an 8-9% weight loss, an overt sign of viral disease, was evident. These findings indicate that the compositions of the present invention have treatment activity utility even after exposure to vaccinia virus. The post-exposure treatment studies indicate that the mAb cocktails are at least 50-fold more potent than VIGIV (vaccinia immune globulin intravenous).

All of the anti-MV:anti-EV mAb mixtures are highly potent. For the anti-MV component, Ch7D11 and h7D11 appear to have equal potency. Of these, h7D11 is favored because it is humanized. For the anti-EV component, Ch12F, Ch6C and Ch8A appear to have equal potency. Of these, Ch12F is favored because it exhibits high affinity binding (0.46 nM) and high preliminary antibody production yields (1.3 g/L). Thus, the most suitable mAbs for the compositions of the present invention are h7D11 and Ch12F.

III. Uses of the Compositions of the Present Invention

The compositions of the present invention are intended for biodefense situations that involve the post-exposure treatment of patients with smallpox and for the post-exposure prophylaxis of smallpox in individuals who have been exposed to variola virus, the causative agent of smallpox. The compositions of the present invention are also intended for the treatment or prevention of human monkeypox, an emerging zoonotic disease.

The compositions of the present invention are also intended for the treatment or modification of the following conditions (which are approved for use with VIGIV) and which may occur as complications of vaccination with vaccinia virus (smallpox vaccine): Eczema vaccinatum; Progressive vaccinia; Severe generalized vaccinia; vaccinia infections in individuals who have skin conditions such as burns, impetigo, varicella-zoster, or poison ivy; or in individuals who have eczematous skin lesions because of either the activity or extensiveness of such lesions; Aberrant infections induced by vaccinia virus that include its accidental implantation in eyes (except in cases of isolated keratitis), mouth, or other areas where vaccinia infection would constitute a special hazard.

The compositions of the present invention have the potential to be used as a pre-exposure prophylactic agent—to be used as an alternative immunization strategy for individuals who are contraindicated for vaccination with vaccinia virus. These contraindications include: Eczema or atopic dermatitis and other acute, chronic, or exfoliative skin conditions; Diseases or conditions which cause immunodeficiency or immunosuppression; Treatments which cause immunodeficiency or immunosuppression; Pregnancy; Previous allergic reaction to smallpox vaccine or any of the vaccine's components; Moderate or severe acute illness; Infants and children; Breast-feeding; and Heart disease.

IV. Administration of the Compositions of The Present Invention

The compositions of the present invention may be provided to recipients in therapeutically effective amounts to treat smallpox. As used herein, a "therapeutically effective amount" refers to that amount of a composition of the present invention sufficient to treat smallpox (or a related disease, such as monkeypox) or to provide a therapeutic benefit in the treatment or management of such disease. An individual having received a therapeutically effective amount of a composition of the present invention exhibits therapeutic passive immunity to smallpox. As such, the symptoms or severity of smallpox is attenuated and recovery from the disease is accelerated.

The compositions of the present invention may be provided to recipients in prophylactically effective amounts to prevent smallpox or attenuate its symptoms or severity. As used herein, a "prophylactically effective amount" refers to that amount of a composition of the present invention sufficient to prevent smallpox (or a related disease, such as monkeypox) or to attenuate the symptoms or severity of such diseases. An individual having received a prophylactically effective amount of a composition of the present invention exhibits prophylactic passive immunity to smallpox. As such, contagion of the disease is prevented or the symptoms or severity of the disease, or its spread to others, is attenuated.

The compositions of the present invention may be provided alone, on in combination with other antiviral therapies. Antiviral drugs target the inhibition of virus replication (e.g., cidofovir) or the egress of virus particles (e.g., ST-246). In contrast, the antibodies of the compositions of the present invention neutralize circulating virus particles, preventing further infection, or bind and neutralize virus particles that are attached to cell surfaces. When antibody-virus complexes are taken up by cells, virus release into the cytoplasm may be inhibited, resulting in the targeting of the virus particles to lysosomes, where they are degraded. Because the mechanisms of action are different, treatments with the compositions of the present invention and antiviral drugs confer a synergistic benefit to the patient.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

The compositions of the present invention are preferably administered to a patient at dosages of 0.0001 mg/kg to 100 mg/kg of the patient's body weight. Preferably, the dosage administered to a patient is between 0.01 mg/kg and 100 mg/kg, 0.1 mg/kg and 100 mg/kg, 0.1 mg/kg and 50 mg/kg, and 0.1 and 30 mg/kg of the patient's body weight. The dosage and frequency of administration of may be reduced or altered by enhancing uptake and tissue penetration, such as, for example, via lipidation. The selected dose level will preferably be based on the serum levels of antibodies that correlate with post-exposure prophylactic or therapeutic efficacy in animal models (vaccinia virus-infected mice, ectromelia virus-infected mice, monkeypox virus-infected macaques). The $EC_{50}$ (50% effective concentration in serum) may be employed to determine a suitable dose. The $EC_{50}$ may be determined from dose titration studies in which the cocktail is administered post-infection at a time that is as delayed as much as possible but still provides significant benefit (i.e., statistically significant increase in survival). The human dose level is preferably a dosage that results in serum concentrations that meet or exceed the serum target level for 30 days or more. A dose of 30 mg/kg or lower is preferred.

The material may be refrigerated (e.g., 4° C.) or maintained at room temperature. Reconstitution with sterile water (e.g., a 25-100 mg/mL solution) will yield a single-dose solution of the cocktail that is to be diluted into saline for IV infusion or may be used undiluted for IM or SC injection. The lyophilized formulation will preferably contain trehalose, a disaccharide that stabilizes freeze-dried proteins exceptionally well. Lyophilized vials are expected to be stable at room temperature prior to reconstitution for 2 years or longer. Single-use, reconstituted vials of the composition are expected to be stable at room temperature for at least one day. The mean terminal half-live of the antibodies of the compositions in humans is expected to be approximately 21 days. In a particularly preferred embodiment, the compositions of the present invention are formulated as a liquid in PBS-T (phosphate buffered saline with TWEEN-80®) that is to be stored at 2-8° C.

Evidence from a post-exposure prophylactic study in which family contacts of smallpox patients received VIG+ vaccine or vaccine alone (Kempe, C. H. et al. (1961) "*The Use Of Vaccinia Hyperimmune Gamma-Globulin In The Prophylaxis Of Smallpox*," Bull World Health Organ. 25:41-48), and from a pre-exposure prophylactic study in which military recruits received VIG+vaccine or vaccine alone (Nanning, W. (1962) "*Prophylactic Effect Of Antivaccinia Gamma-Globulin Against Post-Vaccinal Encephalitis*," Bull. World Health Organ. 27:317-324), suggests that co-administered VIG does not interfere with vaccine efficacy. Thus, the compositions of the present invention do not adversely interfere with the efficacy of other vaccines. By employing, in the compositions of the present invention, antibodies that bind orthopox viruses immunospecifically, interference with live non-orthopox virus vaccines (such as polio, mumps, measles and rubella) or the activity of orthopox antiviral drugs can be avoided.

Most preferably, the compositions of the present invention will be produced as a sterile, preservative-free lyophilized powder under vacuum for intravenous (IV), intramuscular (IM), subcutaneous (SC) or other administration, depending on viscosity and desired dose. In a preferred regimen, the reconstituted composition will be diluted in a suitable volume (e.g., 250 mL) of saline for IV administration. The IV route of administration is advantageous for treatment because it provides maximal circulating levels of the antibody product in a short period of time, which may be critically important for patients not treated until appearance of overt signs of disease. Slow IV infusion is the preferred route of administration. Pump-controlled 60-minute infusions are generally well tolerated and commonly used for delivering monoclonal antibodies. The ability to administer the antibodies rapidly and conveniently is desirable for military or civil defense situations in which large numbers of individuals will need to receive drug in a short period of time. Accordingly, under such circumstances, rapid IV infusion (performed, for example, using a wide-open, IV drip) is preferred provided that the rate of infusion is set to not adversely affect the patient's condition or his/her ability to tolerate the treatment. Formulations that will allow undiluted antibody (after reconstitution of lyophilized material in sterile water) to be administered by IM dosing in a volume of <5 mL or SC dosing in a volume of ≤1 mL are also desirable for such emergency settings.

Administration of a single dose of the composition should be sufficient for therapeutic and post-exposure prophylactic activity. A single prophylactic administration should provide protection against orthopox infection for 2 months or more. The compositors of the present invention are not immunogenic.

A. Post-Exposure Prophylaxis of Smallpox

When administered as a post-exposure prophylactic (i.e., prior to the appearance of overt signs of smallpox or related diseases), the compositions of the present invention are intended to prevent signs and symptoms of the disease, mitigate the severity of any disease that devels, and reduce the spread of infection. Following variola virus infection, there is an approximately 2 week incubation period before overt signs and symptoms of disease appear and a contagious state is reached; this provides a window of opportunity for post-exposure prophylaxis. Smallpox vaccines have been reported to be effective when administered as late as 4 days post infection, but are ineffective when administered later, because there is insufficient time to generate an active immune response. In contrast, passive immunization with the compositions of the present invention provides immediate circulating levels of neutralizing antibodies. Therefore, the compositions of the present invention may provide benefit even when administered toward the end of the incubation period. The compositions of the present invention are expected to be safe and effective for the entire general population. Thus, they should be well tolerated and efficacious in individuals with conditions that are contraindicated for smallpox vaccination, such as eczema or other skin conditions, immunodeficiency, immunosuppression, young age, heart disease, etc.

B. Post-Exposure Treatment of Smallpox

When administered as a post-exposure treatment (i.e., after the appearance of visible pock lesions or other overt disease signs), the compositions of the present invention are intended to mitigate the severity of disease, lower the incidence of death (the mortality rate for untreated cases of smallpox is ~30%), and reduce the spread of infection. The ability of the compositions of the present invention to be effective when administered as a post-exposure treatment is directly supported by studies in vaccinia virus-infected mice in which the treatment reduced mortality when administered after mice had lost 10% of their body weight, an overt sign of disease.

C. Pre-Exposure Prophylaxis of Smallpox

If the compositions of the present invention are administered to individuals in response to a threat or incident of variola virus release, uninfected subjects are likely to receive the drug. The monoclonal antibody components of the cocktail are expected to have long serum half-lives of approximately 20 days, and, as with most viral infections, lower levels of antibody are required for prevention than for treatment. Thus, if administered to subjects who have not been exposed to variola virus (i.e., pre-exposure prophylaxis), a single administered dose of the cocktail should confer immunity for multiple months. Another important application for the cocktail will be its use as an alternative immunization strategy for individuals who are contraindicated for smallpox (vaccinia virus) vaccination.

D. Post-Exposure Prophylaxis or Treatment of Human Orthopox Viruses

The compositions of the present invention exhibit broad neutralizing activity against all orthopox viruses. The sequence of the epitope recognized by the anti-L1 mAb (7D11 and its humanized versions) is 100% conserved in all known species of orthopox virus and 7D11 has been shown to neutralize variola virus in vitro. The sequences of the epitope-containing regions of the A33 and B5 proteins are highly conserved. Moreover, the chimp/human anti-A33 and anti-B5 mAbs have been shown to neutralize variola virus in vitro (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995). A mixture of Ch7D11 and chimp/human anti-A33 and B5 mAbs was effective in neutralizing ectromelia virus. In summary, the data support the ability of the compositions of the present invention to provide therapeutic and prophylactic neutralizing activity against all orthopox viruses.

In particular, the use of the compositions of the present invention in the prevention or treatment of human monkeypox, an emerging zoonotic disease (Parker, S. et al. (2007) "*Human Monkeypox: An Emerging Zoonotic Disease*," Future Microbiol. 2:17-34) is contemplated. The compositions of the present invention are expected to cross-react with and neutralize monkeypox virus.

Infection of rhesus macaques with monkeypox virus (administered IV) causes disease that is similar to variola infection in humans. The intravenous administration of virus in this model mimics the second wave of viremia that occurs just prior to the onset of disease. This viral challenge model is under consideration as a model for licensure of new smallpox vaccines; it also has been used to measure the protective activity of VIG preparations (Golding, H. (2004) "*Evaluation Of Smallpox Vaccine Potency And Safety-Reducing (Or Managing) The Risk Of Adverse Outcomes*," 2004 FDA Science Forum. Vaccinia-specific B-cell responses are essential for protection of macaques from monkeypox virus, because depletion of B cells, but not CD4+ or CD8+ T cells, abrogated vaccine-induced protection from a lethal intravenous challenge with monkeypox virus (Edghill-Smith, Y. et al. (2005) "*Smallpox Vaccine Does Not Protect Macaques With AIDS From A Lethal Monkeypox Virus Challenge*," J. Infect. Dis. 191(3):372-381; Edghill-Smith, Y. et al. (2005) "*Smallpox Vaccine-Induced Antibodies Are Necessary And Sufficient For Protection Against Monkeypox Virus*," Nat. Med. 11(7):740-747). Moreover, VIG administered four days prior to monkeypox virus challenge was sufficient to protect non-immunized macaques from severe disease (Edghill-Smith, Y. et al. (2005) "*Smallpox Vaccine Does Not Protect Macaques With AIDS From A Lethal Monkeypox Virus Challenge*," J. Infect. Dis. 191(3):372-381; Edghill-Smith, Y. et al. (2005) "*Smallpox Vaccine-Induced Antibodies Are Necessary And Sufficient For Protection Against Monkeypox Virus*," Nat. Med. 11(7): 740-747). These data show that neutralizing antibodies are necessary and sufficient to protect against monkeypox virus infection.

Infection of mice with ectromelia virus, a closely related orthopoxvirus, is an excellent surrogate animal model for human smallpox. Similarities between the two infections include virus replication and transmission, aspects of pathology, and development of pock lesions (Buller, R. M. et al. (1991) "*Poxvirus Pathogenesis*," Microbiol. Rev. 55(1):80-122). Studies in B-cell deficient mice have demonstrated that antibodies are obligatory for complete viral clearance and recovery. Moreover, transfer of ectromelia virus-immune serum to B-cell-deficient mice with established infection allowed these animals to clear virus and fully recover. The results show that antibody prevents virus from seeding the skin and forming pock lesions, which are important for virus transmission between hosts (Chaudhri, G. et at. (2006) "*Obligatory Requirement For Antibody In Recovery From A Primary Poxvirus Infection*," J. Virol. 80(13):6339-6344).

Certain recombinant orthopox viruses, such as a genetically engineered ectromelia virus that expresses IL-4, exhibit increased virulence, display resistance to antiviral drugs, and could provide the rationale for a serious biothreat (Robbins, S. J. et at. (2005) "*The Efficacy Of Cidofovir Treatment Of Mice Infected With Ectromelia (Mousepox) Virus Encoding Interteukin-4*," Antiviral Res. 66(1):1-7). The compositions of the present invention may be used in the prevention or treatment of infections caused by any virus having epitopes similar to those of smallpox.

E. Treatment of Complications of Smallpox (Vaccinia Virus) Vaccination

Another intended application of the compositions of the present invention is as an alternative to VIG (vaccinia immune globulin) for the treatment of complications of smallpox (live vaccinia virus) vaccination. VIG is a pool of γ-globulin collected from the plasma of subjects who been vaccinated against smallpox. It is estimated that 1 million vaccinations will result in 250 persons with adverse reactions that will require treatment with VIG. Polyclonal antibody, blood-derived products like VIG are variable in activity, carry the small but real risk of a blood-derived transmission of an infectious agent, and require a supply that is dependent on continual access to large numbers of vaccinated individuals. Currently, VIG is prepared from the plasma of vaccinated military personnel. Another problem is that the potency of VIG is defined by titers from Plaque Reduction Neutralization Tests (PRNT) that measure antibodies that neutralize the MV form of vaccinia virus, but not the EV form. A stable, non-blood derived composition (such as a humanized monoclonal antibody composition) having defined amounts of anti-MV and anti-EV antibodies would be preferred over VIG. As discussed below, based on treatment studies conducted with vaccinia virus-infected mice, the compositions of the present invention are at least 50-fold more potent than VIGIV (vaccinia immune globulin intravenous).

Having now generally described the invention, the same will be more readily understood through reference to the following examples, which are provided by way of illustration and are not intended to be limiting of the present invention unless specified.

Example 1

Isolation and Properties of Vaccinia Virus Neutralizing mAbs

Anti-EV mAbs:

Chimeric chimpanzee/human mAbs that neutralize the EV form of vaccinia virus were isolated and characterized by Drs. Zhaochun Chen and Robert Purcell at the Laboratory of Infectious Diseases/NIAID/NIH in collaboration with Drs. Patricia Earl and Bernard Moss at the Laboratory of Viral Diseases/NIAID/NIH. Chimpanzee Fab fragments were selected from a library derived from the bone marrow of two chimpanzees that had been vaccinated with live vaccinia virus. The chimpanzee Fab sequences were combined with human γ1 constant region sequences to produce full length chimeric antibodies.

Binding Properties of Anti-EV mAbs:

Ch8AH8AL and Ch12F bind with high affinity (4-6×10$^{-10}$M), whereas CH$_6$C binds with moderate affinity (2×10$^{-8}$M). All three mAbs are highly potent in neutralizing the EV form of vaccinia virus in vitro (measured by the comet reduction assay). Two of the mAbs, Ch8AH8AL and Ch6C, have been shown to cross-react with and neutralize the EV form of variola virus in vitro (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995).

As indicated above, the epitope in the B5 viral protein recognized by Ch8AH8AL has been mapped to residues 20-130 (SEQ ID NO:41), which corresponds to the SCR1 and SCR2 portions of the extracellular domain. Epitope mapping was accomplished by blotting similar amounts of different-sized fragments of B5 or A33 protein onto a membrane to which anti-B5 or anti-A33 mAb were added. The bound mAb was detected by HRP-conjugated anti-human IgG (Fab')$_2$. The positive bands were visualized with addition of Lumi-GLO chemiluminescent peroxidase substrate and by exposing the membrane to x-ray film. The epitope appears to be conformational and discontiguous; as shown by the failure to further define it.

In Vivo Neutralizing Activity of Anti-B5 mAb:

Ch8AH8AL was found to protect mice when administered before or 2 days after intranasal challenge with virulent vaccinia virus, and provided significantly greater protection than that afforded by vaccinia immune globulin (VIG) (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887).

In Vivo Neutralizing Activity of Anti-A33 mAbs:

Ch12F and Ch6C was found to protect mice when administered before or two days after intranasal challenge with virulent vaccinia virus, and provided significantly greater protection than that afforded by VIG. The protective efficacy afforded by Ch12F or Ch6C was comparable to that of Ch8AH8AL. However, a combination of anti-A33 mAb (Ch12F or Ch6C) and anti-B5 mAb (Ch8AH8AL) did not synergize the therapeutic activity (Chen, Z. et al. (Jun. 20, 2007) "Characterization Of Chimpanzee/Human Monoclonal Antibodies To Vaccinia Virus A33 Glycoprotein And Its Variola Virus Homolog In Vitro And In A Vaccinia Virus Mouse Protection Model," J. Virol. 81(17):8989-8995). These data support the conclusion that a combination of anti-MV and anti-EV mAbs yields a synergistic immunoprotective response.

Anti-MV mAbs.

Attempts were made to generate chimp/human mAbs that bind the A27 or L1 viral proteins (which are specifically expressed on the surface of MV particles). Several candidates were isolated, but none exhibited potent virus neutralizing activity. This is consistent with the observation that anti-L1 mAbs appear to be poorly immunogenic and of relatively low abundance following vaccinia virus vaccination (Lawrence, S. J. et al. (2007) "Antibody Responses To Vaccinia Membrane Proteins After Smallpox Vaccination," J. Infect. Dis. 196(2):220-229). However, 7D11, a potent murine anti-L1 mAb has been isolated and shown to have neutralizing activity (Wolffe, E. J. et al. (1995) "A Myristylated Membrane Protein Encoded By The Vaccinia Virus L1R Open Reading Frame Is The Target Of Potent Neutralizing Monoclonal Antibodies," Virology 211 (1):53-63; Hooper, J. W. et al. (2000) "DNA Vaccination With Vaccinia Virus L1R And A33R Genes Protects Mice Against A Lethal Poxvirus Challenge," Virology 266(2):329-339). The binding properties of monoclonal antibody 7D11 was therefore evaluated to determine the suitability of 7D11 as an anti-MV mAb of the present invention.

Binding Properties of the Anti-MV mAb 7D11:

7-D11 binds L1 protein with moderate affinity ($K_D$ of $3.6 \times 10^{-8}$ M). The crystal structure of 7D11 bound to L1 (Su, H. P. et al. (2007) "Structural Basis For The Binding Of The Neutralizing Antibody, 7D11, To The Poxvirus L1 Protein," Virology 4:78 (pp. 1-12) reveals that 7-D11 binds to a conformational epitope of 12 residues of L1. The conformational epitope is positioned at the ends of loops of the ectodomain of the L1 protein. All of the contacts interact with the 7D11 heavy chain and there are no significant contacts with the 7D11 light chain. As indicated above, the 12-residue epitope (underlined residues of SEQ ID NOS: 13-15) and its adjacent sequences (SEQ ID NOS: 13-15) are 100% conserved in all orthopox viruses and the antibody is thus expected to neutralize all orthopox virus species. mAb 7D11 has been shown to neutralize variola virus in vitro. The mechanism of vaccinia virus neutralization is not understood, but neutralizing activity is retained even when the antibody is added after virus adsorption to cells (Su, H. P. et al. (2007) "Structural Basis For The Binding Of The Neutralizing Antibody, 7D11, To The Poxvirus L1 Protein," Virology 4:78 (pp. 1-12)).

In Vivo Neutralizing Activity of the Anti-MV mAb 7D11:

Passive transfer of 7D11 has been shown to protect mice against lethal intraperitoneal challenge with vaccinia virus (Schmaljohn, C. (1999) "Production And Characterization Of Human Monoclonal Antibody Fab Fragments To Vaccinia Virus From A Phage-Display Combinatorial Library," Virology 258(1):189-200) and against lethal intranasal challenge with vaccinia virus (Lustig, S. et al. (2004) "Synergistic Neutralizing Activities Of Antibodies To Outer Membrane Proteins Of The Two Infectious Forms Of Vaccinia Virus In The Presence Of Complement," Virology 328(1):30-35). Moreover, combinations of a murine anti-MV antibody (7D11) and murine anti-EV antibodies were more potent than individual antibodies by themselves (Lustig, S. et al. (2004) "Synergistic Neutralizing Activities Of Antibodies To Outer Membrane Proteins Of The Two Infectious Forms Of Vaccinia Virus In The Presence Of Complement," Virology 328(1):30-35).

Example 2

Synergy of Mixtures of Anti-EV and Anti-MV mAbs

Evidence supports the possibility that a mixture of EV-specific and MV-specific mAbs would be synergistically more effective at neutralizing vaccinia virus relative to single mAbs. Genetic immunization studies have demonstrated the superiority of mixtures of plasmids encoding EV-specific proteins (B5, A33) and MV-specific proteins (A27, L1) in conferring protection in mice from vaccinia virus challenge and protection in monkeys from monkey pox challenge (Hooper, J. W. et al. (2003) "Four-Gene-Combination DNA Vaccine Protects Mice Against A Lethal Vaccinia Virus Challenge And Elicits Appropriate Antibody Responses In Nonhuman Primates," Virology 306(1):181-195; Hooper, J. W. et al. (2004) "Smallpox DNA Vaccine Protects Nonhuman Primates Against Lethal Monkeypox," J. Virol. 78(9):4433-4443). Additionally, recombinant protein immunization studies have shown that a mixture of proteins (B5+A33+L1 or A33+L1) provided superior protection from vaccinia virus challenge in mice (Fogg, C. et al. (2004) "Protective Immunity To Vaccinia Virus Induced By Vaccination With Multiple Recombinant Outer Membrane Proteins Of Intracellular And Extracellular Virions," J. Virol. 78(19):10230-10237). Evidence for synergism between an EV-specific and MV-specific antibody was observed in an in vitro EV neutralization study, where a mixture of polyclonal antibody to A33 and monoclonal antibody to L1 (7D11) was considerably more potent than either antibody alone (Lustig, S. et al. (2004) "Synergistic Neutralizing Activities Of Antibodies To Outer Membrane Proteins Of The Two Infectious Forms Of Vaccinia Virus In The Presence Of Complement," Virology 328(1):30-35). Without intending to be bound by any mechanism, the observation that antibodies specific for the MV form of vaccinia helped to neutralize EV supports a model in which EV-specific mAbs first bind to EV membranes, which are lysed in the presence of complement. Such lysis causes the release of MV particles, which are then neutralized by the MV-specific antibody.

Direct evidence for the superiority of mixtures of EV-specific and MV-specific monoclonal antibodies in conferring protection from vaccinia virus infection in mice is disclosed in Lustig, S. et al. (2004) ("Synergistic Neutralizing Activities Of Antibodies To Outer Membrane Proteins Of The Two Infectious Forms Of Vaccinia Virus In The Presence Of Complement," Virology 328(1):30-35). When administered 2 days prior to virus challenge, individual antibodies (of rodent origin) were found to confer little protection at doses of 100 µg or 200 µg. In contrast, antibody mixtures that contained one anti-MV mAb and at least one anti-EV mAb (A33+B5+L1, A33+L1 or B5+L1) were found to confer strong protection. Because the total antibody dose in employed was the same for individual antibodies and mixtures, the increased level of protection observed with mixtures cannot be attributed simply to a higher dose. The mAbs used in these studies, 7D11 (L1 mAb), 19C2 (B5 mAb) and IG10 (A33 mAb), were all rodent in origin. In vaccinia virus challenge studies, the chimp/human mAb 8AH/8AL was more potent than 19C2 (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887). Similarly, the chimp/human mAbs Ch6C and Ch12F were more potent than IG10 (Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17): 8989-8995). These findings predict that cocktails containing the high affinity chimp/human mAbs of the present invention should be more potent (i.e. effective at lower dose) than the cocktails of rodent mAbs taught by Lustig, S. et al. (2004) ("*Synergistic Neutralizing Activities Of Antibodies To Outer Membrane Proteins Of The Two Infectious Forms Of Vaccinia Virus In The Presence Of Complement*," Virology 328(1):30-35).

Example 3

Variola Virus Neutralizing Activity

A comparison of the sequences of variola and vaccinia B5 proteins in the region corresponding to the epitope recognized by 8AL/8AH reveals 10 amino acid differences (discussed above). A Western blot study showed that 8AL/8AH cross-reacted with a variola B5 polypeptide corresponding to 111 amino acids, which had been expressed in *E. coli*. Moreover, in a study performed at the Centers for Disease Control, 8AH/8AL inhibited variola virus comet formation, an assay that specifically measures EV neutralizing activity. Similarly, 6C inhibited variola virus comet formation. For these studies, monolayers of BS-C-40 cells were infected with the Solaimen strain of variola virus. After 1 h, the medium was aspirated; cells were washed twice, and overlaid with RPMI containing 25 μg, 2.5 μg, or 0 μg of 6C IgG. The plates were then incubated in a $CO_2$ incubator for 4 days at 35.5° C. Cells were fixed and reacted with polyclonal rabbit anti-variola virus antibody. Following incubation with goat anti-rabbit-HRP conjugate, comets were visualized by addition of TruBlue 5 peroxidase substrate (see, Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103 (6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995). These data show that the chimp/human anti-B5 and anti-A33 mAbs cross-react with and neutralize the EV form of variola virus. 7D11, the anti-MV mAb, also has been shown to neutralize variola virus in vitro (Inger Damon, CDC, personal communication). Although not tested yet, Ch12F is expected to neutralize variola virus, because it appears to bind to the same epitope as 6C.

Example 4

Construction of Chimeric Anti-EV mAbs (Ch8A, Ch6C, Ch12F)

Chimeric Anti-EV mAbs (Ch8A, Ch6C, Ch12F) targeting, respectively, epitopes of B5, A33 and A33 were constructed as follows: The light chain (LC) and heavy chain (HC) coding sequences of the chimp/human Fabs were cloned into the pComb3H vector (Barbas, C. F. III, et al. (1991) "*Assembly of combinatorial antibody libraries on phage surfaces: the gene III site*," Proc. Natl. Acad. Sci. (U.S.A.) 88(18):7978-7982), using Sac I and Xba I sites for the LC sequences, and Xho I and Spe I sites for the HC sequences. To allow expression and secretion, a mouse recombinant signal sequence was added to the beginning of the LC and VH by overlapping PCR. The Sac I site at the beginning of 8A LC and the Xho I site at the beginning of 8A VH was kept intact. The overlapping PCR product of the 8A LC was cloned into pUC19 vector at Hind III/XbaI sites. The 8A LC sequence in pUC19 was then swapped by 6C LC sequence and by 12F LC sequence at the Sac I/Xba I sites to add the signal sequence into both LCs. The Ch8A LC, Ch6C LC and Ch12F LC from pUC19 vector were then subcloned into pEE13 vector (Lonza Biologics) at Hind III/EcoRI sites. Since there are two Hind III sites in the pEE13 vector, the vector was digested with Hind III-Bgl II and Bgl II-EcoR I and three fragments were ligated together. The overlapping PCR product of 8A VH was directly cloned at Hind III/ApaI sites in pEE6 backbone based vector with human IgG1 constant region to create Ch8A HC. The Ch6C HC and Ch12F HC were generated by replacing the Ch8A VH sequence with 6C VH or 12F VH sequence at Xho I/Apa I sites. Since the pComb3H vector provides EVQL, the HC amino terminus, direct swapping at Xho I/Apa I site for making ChHCs lost the four amino acids at the amino terminus. The four amino acids were added back by site-direct mutagenesis (Strategene, Inc.). Expression cassettes containing the HCs were then digested out of pEE6 vectors with Bgl II and Sal I and ligated into BamH I/Sal I-digested pEE13 that contained the appropriate LC to generate single vectors with individual expression cassettes for Hc and Lc. The coding sequences of all constructs were confirmed by sequencing analysis. The single vector DNA for each mAb was linearized at the FsP I site for stable cell line generation.

Example 5

Construction of Chimeric Anti-MV mAb (Ch7D11)

Monoclonal antibody Ch7D11 (chimeric 7D11) was constructed from RNA obtained from the 7D11 murine hybridoma. The RNA was reverse transcribed into cDNA and the VH and VL segments were PCR amplified using the 5' RACE System for Rapid Amplification of cDNA Ends kit (Invitrogen, Inc.). Gene-specific primers for the VH were SJ15R (SEQ ID NO:42) and SJ16R (SEQ ID NO:43).

SEQ ID NO: 42:    ggtcactgtc actggctcag gg

SEQ ID NO: 43:    aggcggatcc aggggccagt ggatagac

The gene-specific primer for VL was lgh249r (SEQ ID NO:44).

SEQ ID NO: 44:    cttccacttg acattgatgt ctttggg

The RACE product was inserted into the plasmid pCR2.1-TOPO using a TOPO TA Cloning kit (Invitrogen, Inc.). The resulting plasmids were subjected to DNA sequencing to determine the VH and VL nucleotide sequences for 7D11. These sequences were translated and the predicted amino acid sequences were confirmed. The framework (FR) and complementarity determining (CDR) regions were identified as defined by Kabat (Kabat, E. A. et al. (1991) "PROTEINS OF IMMUNOLOGICAL INTEREST," Publication No. 91-3242. Bethesda, Md.: National Institutes of Health). The mouse VH was then joined to a human C-Gamma1 constant region and an Ig leader sequence and inserted into pCI-neo for mammalian expression. The mouse VL was joined to a human C-kappa segment and an Ig leader sequence and also cloned into pCI-neo for mammalian expression.

Example 6

Construction of Humanized Anti-MV mAb (h7D11)

Figures 2, 3:
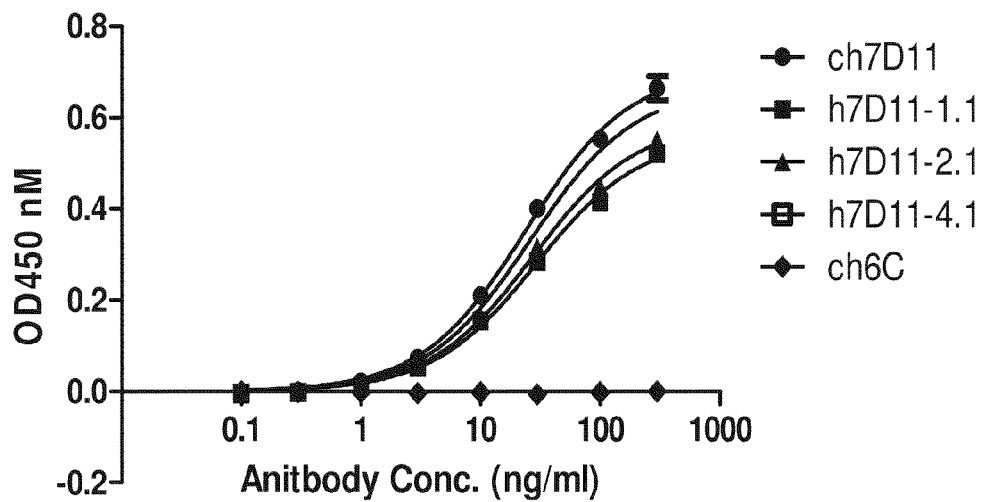
FIG. 2 shows the alignment of mouse 7D11 VL (mVL) (SEQ ID NO:2) and humanized 7D11 VL (hVL) (SEQ ID NO:6).
FIG. 3 shows the results of ELISA binding of h7D11 variants to L1 viral protein.

The sequence of humanized 7D11 (h7D11) was designed as follows. VH consists of the framework (FR) segments from the human germline VH segments VH1-18 (FR segment 1 and 2), VH1-69 (FR segment 3) and JH4; and the murine complementarity determining regions (CDRs) of 7D11 VH. Humanized 7D11 VL consists of the FR segments of the human germline VL segments VK-B3 and JK2; and the murine CDRs of 7D11 VL. FIG. 1 shows the alignment of mouse 7D11 VH (mVH) (SEQ ID NO:4) and humanized 7D11 VH (hVH) (SEQ ID NO:10). FIG. 2 shows the alignment of mouse 7D11 VL (mVL) (SEQ ID NO:2) and humanized 7D11 VL (hVL) (SEQ ID NO:6).

The humanized VH and VL sequences were synthesized from oligonucleotides (GenScript Corp.). The synthetic heavy and light chain fragments were individually combined by PCR with a leader sequence and an appropriate constant region segment and cloned into the expression vector pCI-neo, using NheI-Apa I for the heavy chain fragment and Nhe I-EcoR I for the light chain fragment. The DNA sequence of the resulting plasmids was confirmed by sequence analysis.

The h7D11 heavy chain (HC) and light chain (LC) expression plasmids were co-transfected into HEK-293 cells. At the same time, Ch7D11 HC was co-transfected with Ch7D11 LC; h7D11 HC was co-transfected with Ch7D11 LC; and Ch7D11 HC was co-transfected with h7D11 LC. After three days in culture the amount of human IgG expressed was quantitated by ELISA. Binding to vaccinia virus L1 recombinant protein was then determined by ELISA. The results from the chain swapping study indicated that all of the IgG molecules with Ch7D11 HC had higher affinity than any of the ones with h7D11 HC.

To improve h7D11 HC, murine amino acids were restored at positions 48, 67 and 69, individually or combined, using site-directed mutagenesis. These amino acids were chosen because they are Vernier residues, which are known to be involved in the positioning of the CDRs. The list of h7D11 variants that were constructed is shown in Table 1.

TABLE 1 h7D11 Variants

| H chain name | L chain name | mAb name |
| --- | --- | --- |
| h7D11Hc | h7D11Lc | h7D11-1.1 |
| h7D11Hc M48I | h7D11Lc | h7D11-2.1 |
| h7D11Hc I69L | h7D11Lc | h7D11-3.1 |
| h7D11Hc M48I, I69L | h7D11Lc | h7D11-4.1 |
| h7D11Hc V67A | h7D11Lc | h7D11-5.1 |
| h7D11Hc V67A, I69L | h7D11Lc | h7D11-6.1 |
| h7D11Hc M48I, V67A, I69L | h7D11Lc | h7D11-7.1 |

Transfections of HEK-293 cells were performed with various heavy and light chain combinations and the binding of the resultant IgGs to L1 protein was quantitated by ELISA. All IgGs with the new h7D11 HC variants exhibited increased binding to the antigen compared to IgGs with the initial version of h7D11 HC. The best HC variants were h7D11 HC-M48I, I69L and h7D11 HC-M48I, V67A, I69L. The respective humanized mAbs, h7D11-4.1 and h7D11-7.1, were analyzed by ELISA as follows: 15 ng/well of soluble recombinant Smallpox vaccinia virus L1 protein was directly coated on 96-well MAXISORP® plates at 4 C overnight. A series of three-fold dilutions of conditioned medium of Ch7D11, h7D11-1.1, h7D11-2.1, h7D11-4.1 and Ch6C starting from 15 ng/well was added to the each well. Ch6C was employed as the negative control. The plate was incubated at room temperature for 1 hour, then binding was detected by 50 µl of HRP conjugated goat anti human IgG (H+L) (Jackson ImmunoResearch) secondary antibody at 1:10,000 dilution. After incubation with the secondary antibody for 1 hour, the plate was developed by TMB substrate. After 5 minutes incubation, the reaction was stopped by 1% $H_2SO_4$. The $A_{450}$ nm was read using the SOFTmax program. Between each step, the plate was washed 3 times with Phosphate Buffered Saline (PBS)/0.1% TWEEN-20®. The plate was blocked by 0.5% BSA in PBS/0.1% TWEEN-20® for 30 min at room temperature before adding testing antibodies. mAbs h7D11-4.1 and h7D11-7.1 were found to have binding affinities that were indistinguishable from that of Ch7D11. Because it had fewer back mutations, h7D11-4.1 was selected as the humanized 7D11 mAb for further development.

h7D11 binds L1 protein with moderate affinity (KD of $3.6 \times 10^{-8}$ M). By increasing the affinity of h7D11, virus neutralizing potency can be increased, which may increase therapeutic activity and allow a lower dose to be utilized. This is desirable, because, as the dose is lowered, the feasibility of administering the mAbs by a single IM injection is increased.

Affinity Maturation

Figure 15:
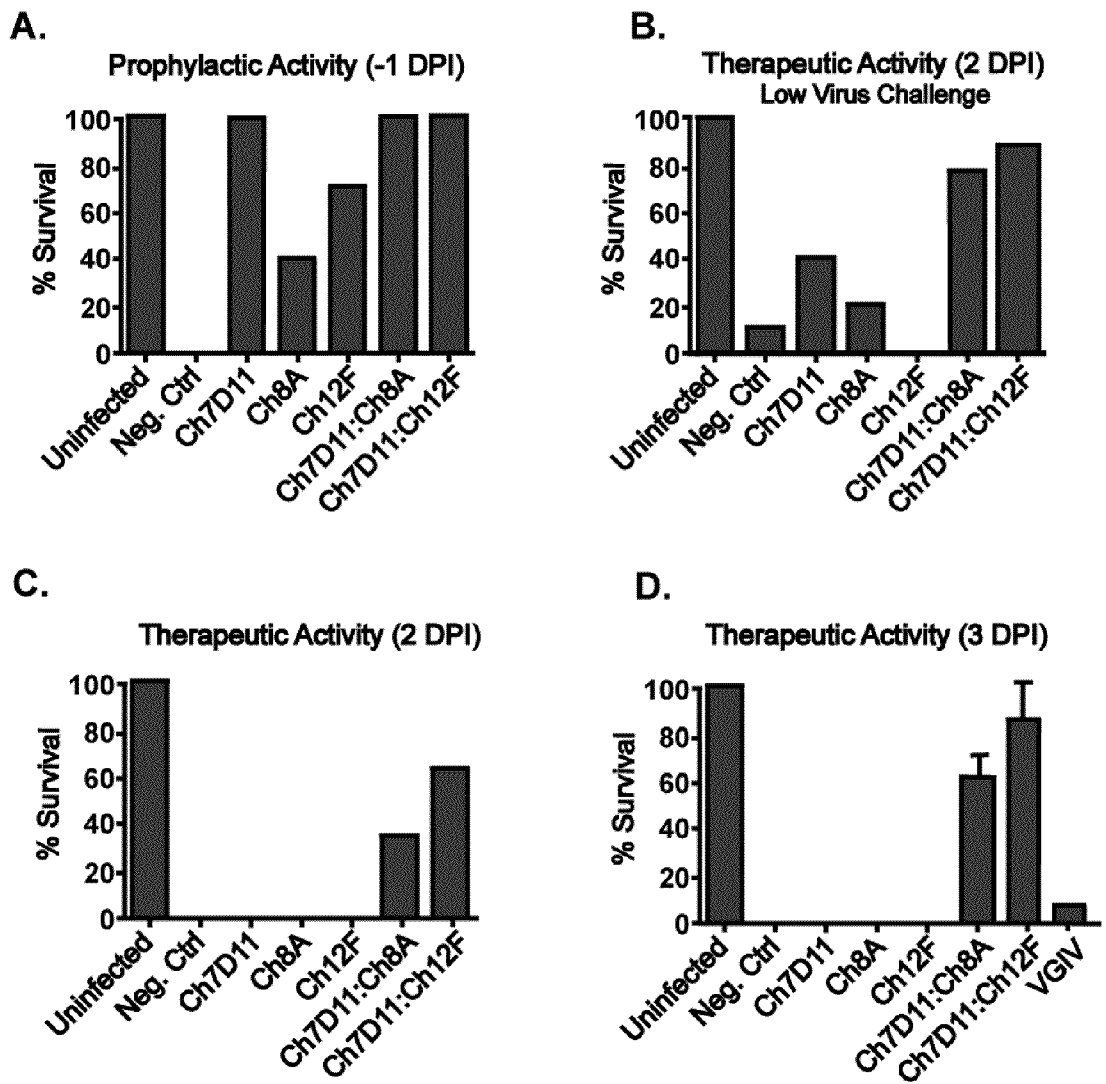
Figure 17A:
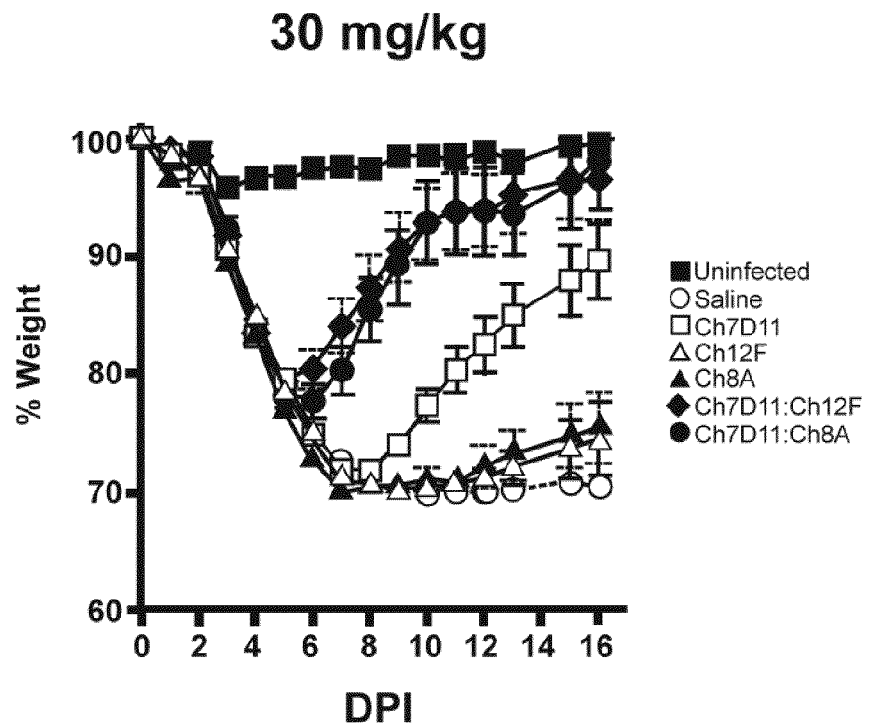
Figure 17B:
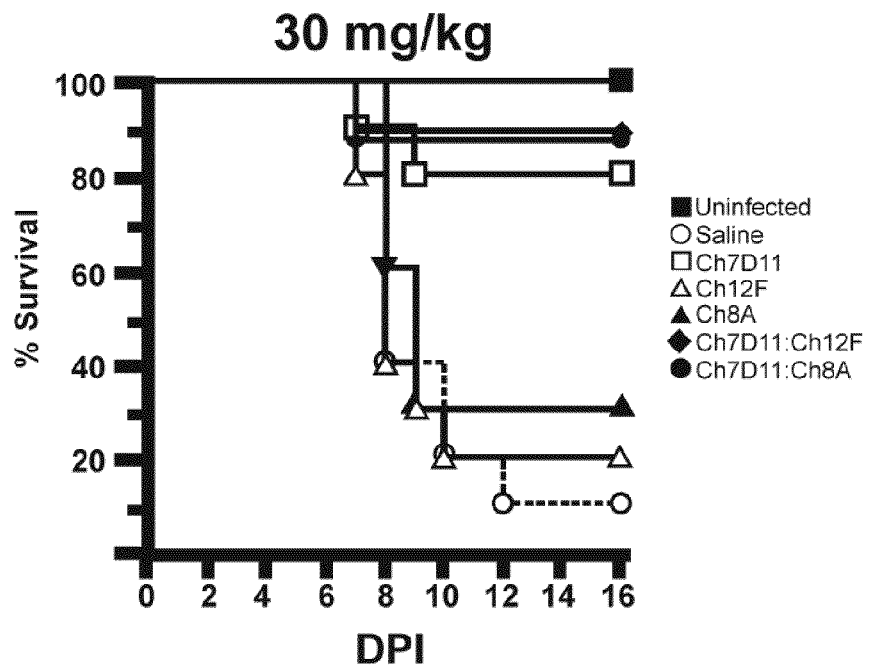
Figure 17C:
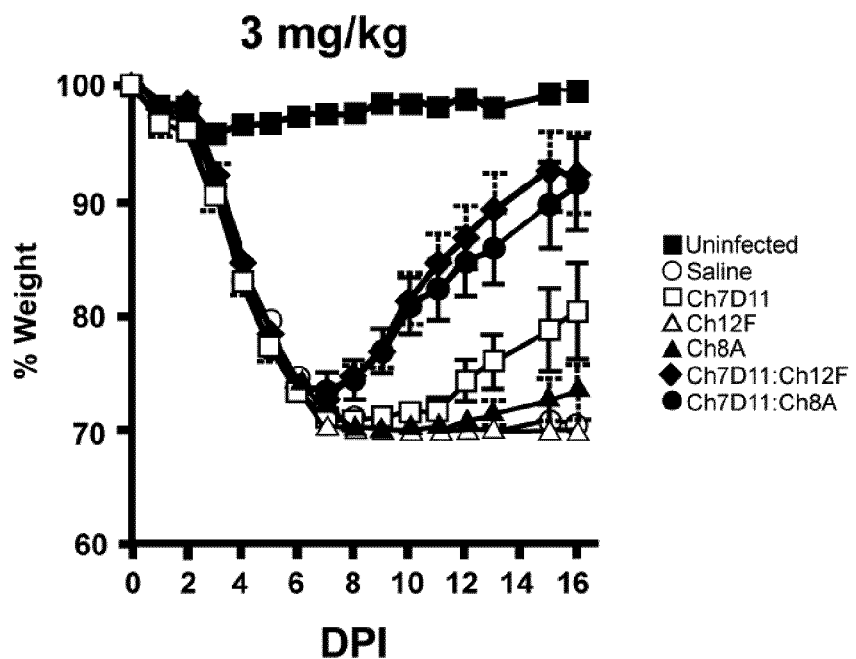
Figure 17D:
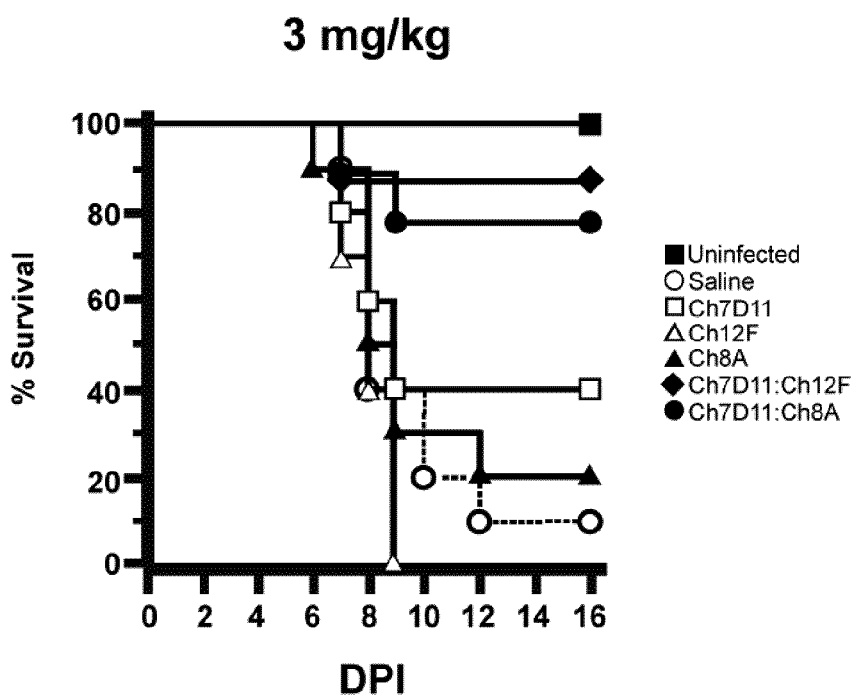
Figure 17E:
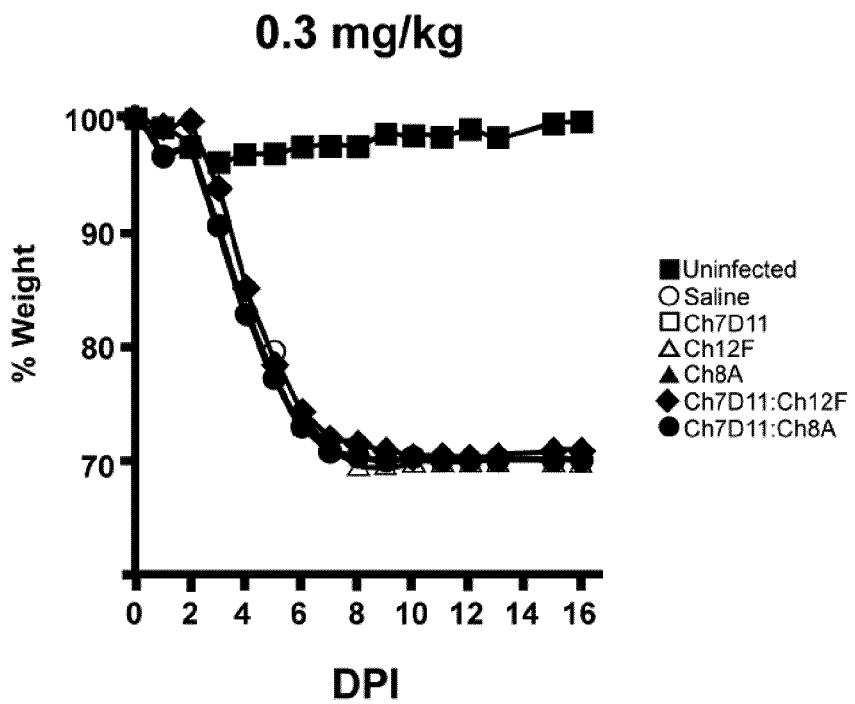
Figure 17F:
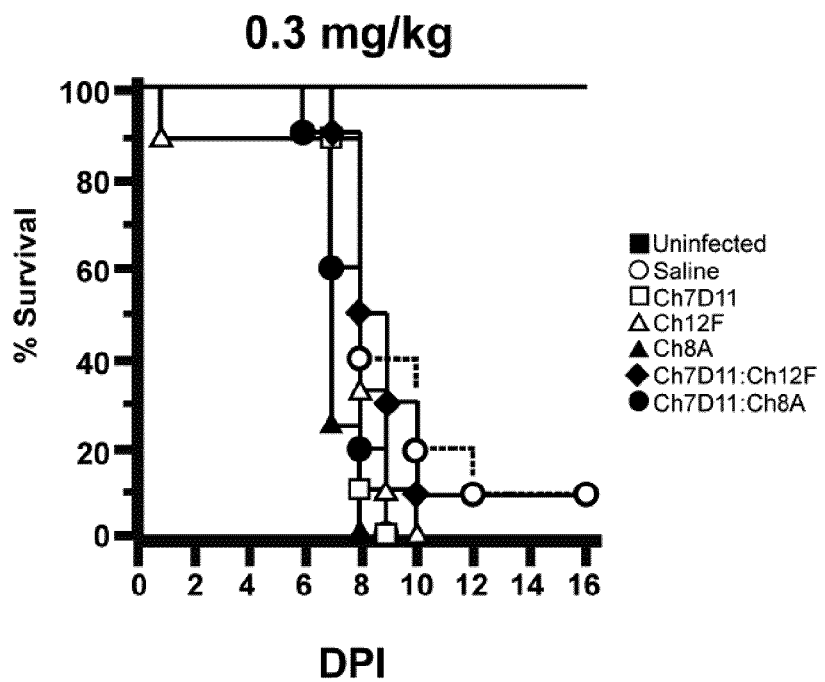

The published crystal structure of 7D11 bound to the L1 protein (Su, H.-P. et al. (Epub 3 Aug. 2007) "*Structural Basis For The Binding Of The Neutralizing Antibody, 7D11, To The Poxvirus L1 Protein*," Virology 368(2):331-341) shows that the 7D11 light chain does not make any contacts with L1 and it covers less than 15% of the binding interface (FIG. 15). Further, surface complementarity at the light chain-L1 interface is very poor, suggesting that the light chain may serve solely as a support for the heavy chain, which in turn is solely responsible for interaction with L1. This finding suggests two ways to improve the binding of h7-D11 to L1. First, the light chain may be optimized by substituting a library of alternate human light chains for the h7D11 light chain. Second, the heavy chain may be affinity matured by systematic mutagenesis of the CDR residues followed by high throughput screening for improved binders.

Light Chain Optimization

Two complementary approaches may preferably be undertaken to identify optimized light chain sequences to pair with the h7D11 heavy chain. First, a directed approach may be employed to identify and clone all of the V genes next to appropriate J segments to represent all possible 512 germline variable regions. In a second parallel approach, a library may be screened in order to examine a greater complexity of germline as well as uniquely rearranged and somatically mutated variable regions.

A cDNA library may be prepared from normal human donor bone marrow. Degenerate and universal primers may then be used to amplify light chain sequences from the cDNA library. The light chain library with h7D11 heavy chain is preferably cloned into a dual expression vector capable of mediating Fab expression and secretion in prokaryotic *E. coli* cells as well as IgG expression and secretion in mammalian cells.

Once the library has been generated, 200-300 clones may be sequenced to measure the complexity of the library and to identify clones containing specific VL genes. There are 36 functional lambda and 52 functional kappa V genes in the human germline. Further, there are 5 J-kappa segments, each of which can be combined with any V-kappa gene (260 V-J combinations) and 7 J-lambda segments, each of which could be combined with any V-lambda gene (252 V-J combinations). An initial round of sequencing can identify the majority of the V genes, which can then each be cloned into vectors containing the repertoire of appropriate J segments followed by C regions. Any V genes that are not represented can be cloned by amplification with specific primers, by mutagenesis of similar genes, or by de novo synthesis. This defined set of germline light chain genes can then be used in combination with the h7D 11 heavy chain gene (Fd fragment) to co-transfect eukaryotic cells. Cell supernatants may be harvested and the recombinant Fabs tested for improved binding to L1, e.g., by ELISA. The benefits to this approach include exhaustive sampling of the entire germline repertoire and avoidance of bias within libraries or pools. Further, once generated, such a library may be rapidly applied to other antibody products.

The light chain cDNA library may also be screened by performing Fab captured L1 binding specific colony lift assay from, e.g., approximately 10,000 bacterial clones. DNA from clones that show higher affinity than h7D11 may be isolated and sequenced. At the same time, the high affinity clones may be directly expressed as whole IgG in mammalian system without subcloning. The affinity may be measured, for example, in well-controlled binding ELISA and/or Biacore assays. The benefits of this approach include the ability to sample diverse V-J junctions and somatically mutated CDRs that may contribute to a more effective final product.

Heavy Chain Optimization:

Affinity maturation of the heavy chain can be performed in parallel with the light chain swapping approach, as the majority of contacts between heavy and light chains are in framework regions. The preferred approach is to mutagenize the CDR residues within the heavy chain and to measure the effect of the change on binding affinity. The mutagenesis may be accomplished using a modified QuikChange strategy to change every CDR residue to all other possible amino acids, one at a time. Single changes that improve affinity may be identified and engineered into genes in a variety of combinations to generate a first-round optimized candidate. This candidate may then be subjected to a second round of mutagenesis at every residue to identify second-site changes that might only be beneficial in the context of changes identified in the first round. Again, beneficial changes may be tested in various combinations to identify the final optimized molecule.

The structural information that is available for the 7D11-L1 complex also provides a basis for rational mutagenesis strategies or saturation mutagenesis of a smaller subset of CDR residues (those at or near the binding interface), potentially streamlining the process.

Example 7

Stable Cell Line Development and mAb Purification

Stably-transfected mammalian cells that produce chimeric antibodies directed against the vaccinia extracellular enveloped virus antigens A33, B5 and L1 were generated using the Glutamine Synthetase gene expression system from Lonza Biologics (Slough, UK). The Chinese hamster ovary cell line, CHO-S, was obtained from Invitrogen. CHO-S is a clonal isolate derived from the parental line CHO-K1 that has been adapted to suspension culture. The CHO-S cell line was maintained in CD-CHO medium, a chemically-defined, protein- and serum-free medium containing no animal-origin materials, supplemented with Gluta-MAX (alanine-glutamine di-peptide), hypoxanthine and thymidine. Cells were maintained as suspension cultures in shake flasks at 37 C, in 8% $CO_2$, at densities between $3 \times 10^5$ and $6 \times 10^6$ cells/mL.

Plasmid DNA was purified using a Qiagen MaxiPrep kit and linearized with the enzyme, Fsp I. Linearized DNA was extracted, ethanol-precipitated, and suspended in sterile, distilled water at approximately 1 µg/µL. CHO-S cells were transfected with linearized expression vector using a synthetic, cationic lipid reagent. At 24 hours post-transfection, cells were re-suspended in selection medium consisting of CD-CHO without glutamine containing 25 µM Methionine Sulfoximine (MSX), an inhibitor of glutamine synthetase. Transfected cells in selection medium were seeded in 96-well plates at a density of 2000 cells/well, and incubated at 37° C. with 8% $CO_2$.

The 96-well plates were monitored for colony growth, which was observed at 4-5 weeks post seeding. Supernatants from wells with single colonies were screened for the presence of antibody by a sandwich-based ELISA protocol. Concentrations of unknown samples were calculated using a standard curve made with purified antibody whose concentration had been determined by $A_{280}$ using an extinction coefficient determined by amino acid analysis.

A total of 65 (Ch8A), 139 (Ch6C), 97 (Ch12F), and 159 (Ch7D11) primary transfectants were screened by ELISA. The transfectants with the highest expression levels (9 of Ch8A; 7 of Ch6C; 16 of Ch12F; and 13 of Ch7D11) were pooled and expanded in 6-well plates in selection medium, then transferred to shake-flask cultures for further expansion in CD-17 medium containing 25 µM MSX. Antibody levels of the selected transfected colonies in 96-well plates were estimated by ELISA to be from 4 to >20 mg/L.

Cells in log-growth were collected by centrifugation and a portion of this cell-conditioned media was retained to make up the cryopreservation medium. Cells were suspended and frozen in a 50:50 mixture of fresh and cell-conditioned CD-17 media containing 7.5% DMSO. Vials containing $1.5 \times 10^7$ cells in 1.5 mL of freezing medium were stored in the vapor phase of a liquid nitrogen freezer.

Stable cell pools were expanded in shake flasks to produce antibody in fed-batch cultures. Cells were seeded at a density of $3 \times 10^5$ cells/mL in CD-17 medium supplemented with 25 µM MSX. Media was supplemented every other day, starting at Day 3 post-seeding, with glucose, amino acids and hydrolysate. Temperature was lowered from 37° C. to 32° C. at day 3. Samples were monitored for cell growth, viability, and antibody expression level. At approximately day 15, cultures were clarified by centrifugation and supernatants were filtered using a 0.2 µsterile filter. Antibody expression levels, as measured by ELISA, were 0.6 to 1.4 grams/Liter (Table 2). The antibodies were purified from a portion of the 1 liter fed-batch cultures of the stable, positive pools by protein A sepharose chromatography and size exclusion chromatography (Table 2). Endotoxin levels were less than 0.2 EU/mg.

TABLE 2 mAb Expression Levels And Purification

| mAb | Cell Culture Expression Level (G/L) | Purified mAb Concentration (mg/mL) | Total (mgs) | Lot# |
|---|---|---|---|---|
| Ch7D11 | 0.8 | 7.8 | 210 | P192.212 |
| Ch8A | 0.6 | 7.4 | 200 | P192.210 |
| Ch6C | 0.9 | 7.2 | 207 | P192.211 |
| Ch12F | 1.4 | 12.0 | 194 | P192.216 |

Example 8

Binding Properties of Purified mAbs

Figure 4:
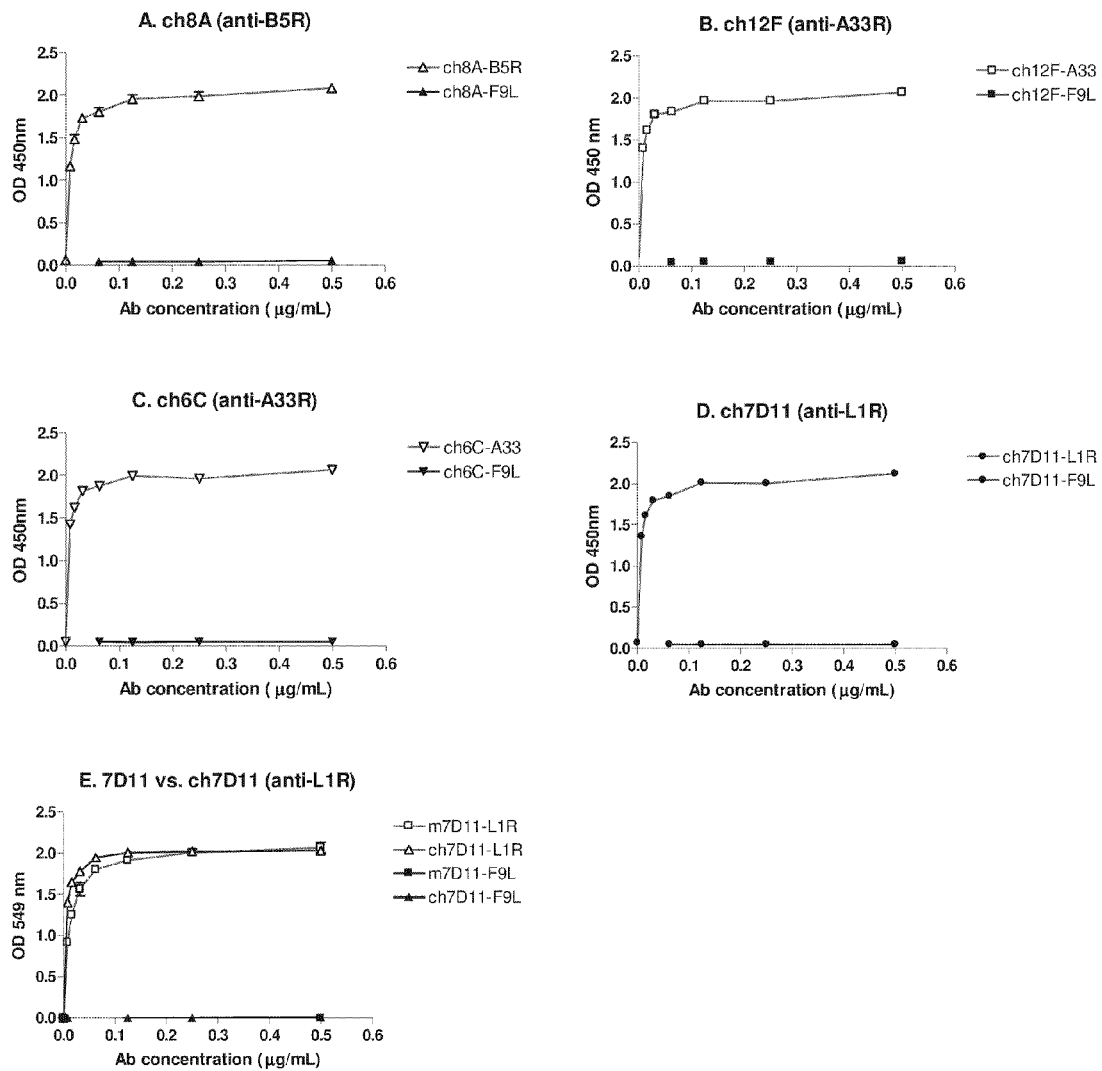
FIG. 4 (Panels A-E) shows ELISA data on the specific binding of purified monoclonal antibodies to their respective recombinant protein target antigens. Panel A: Binding of ch8A (anti-B5R) to recombinant B5R protein. Panel B: Binding of ch12F (anti-A33) to recombinant A33 protein. Panel C: Binding of ch6A (anti-A33) to recombinant A33 protein. Panel D: Binding of ch7-D11 (anti-L1) to recombinant L1 protein. Panel E: Comparison of the binding of 7-D11 and ch7-D11 to recombinant L1 protein. In each case, vaccinia virus protein F9L was utilized as a negative control. The vaccinia recombinant proteins were obtained from BEI Resources.

The binding properties of each of the purified antibodies were tested by ELISA and each antibody exhibited specific binding to its intended target antigen with no detectable binding to a control vaccinia antigen (Table 3; FIG. 4, Panels A-E). Moreover, the binding properties of Ch7D11 and 7D11 were similar. Ch12F binds A33 with high affinity ($K_D$ of $4.6 \times 10^{-10}$ M). Thus, further modification was not warranted. Moreover, humanization is not necessary because of the high degree of homology in chimpanzee and human immunoglobulin sequences.

TABLE 3

Binding Properties of mAbs Determined by Surface Plasmon Resonance

| mAb | $K_{on}$ (M$^{-1}$ s$^{-1}$) | $K_{off}$ (s$^{-1}$) | $K_D$ (M) |
|---|---|---|---|
| Ch8A   | $2.0 \times 10^4$ | $1.0 \times 10^{-5}$ | $6.0 \times 10^{-10}$ |
| Ch6C   | $6.8 \times 10^3$ | $1.4 \times 10^{-4}$ | $2.0 \times 10^{-8}$ |
| Ch12F  | $4.6 \times 10^4$ | $2.2 \times 10^{-5}$ | $4.6 \times 10^{-10}$ |
| Ch7D11 | $3.5 \times 10^5$ | $5.8 \times 10^{-3}$ | $1.7 \times 10^{-8}$ |
| h7D11  | $2.7 \times 10^5$ | $9.7 \times 10^{-3}$ | $3.6 \times 10^{-8}$ |

Example 9

In Vitro Neutralization Activity of Ch7D11, Ch8A, Ch12F and Ch6C

The in vitro neutralizing activities of the anti-MV mAbs (7D11 and Ch7D11) were measured by assays that utilized a recombinant vaccinia virus that expresses green fluorescent protein (GFP) and flow cytometry to enumerate infected cells (Earl, P. L. et al. (2003) "*Development And Use Of A Vaccinia Virus Neutralization Assay Based On Flow Cytometric Detection Of Green Fluorescent Protein*," J. Virol. 77(19): 10684-10688). The IC$_{50}$ value was found to be 3.5 ng/ml for murine 7D11 and 3.0 ng/ml for Ch7D11. Thus, there was no significant difference in the neutralizing activities of the two mAbs. The in vitro neutralizing activities of the anti-EV mAbs (Ch8A, Ch6C, Ch12F) were confirmed in comet reduction assays. In these assays, BS-C-1 cells were infected with approximately 50 pfu of VACV, strain IHD-J. After 2 h at 37° C., the monolayer was washed, and fresh medium containing indicated amounts of anti-EV mAb was added. Commercially available Synagis (anti-RSV mAb) served as the negative control. After 48 h, the monolayers were stained with crystal violet. All three mAbs exhibited anti-EV neutralizing activity.

Example 10

In Vivo Neutralization Activity of Ch7D11, Ch8A, Ch12F and Ch6C

Murine Vaccinia Virus Challenge Model.

Intranasal or intratracheal inoculation of mice with vaccinia virus is known to produce local replication and systemic disease, and thus provides a system capable of assessing antiviral activity at multiple steps in the virus life cycle. Establishment of lethal infection requires a large dose of virus ($10^4$-$10^6$ pfu). The infection starts locally in nasal tissue and lungs before spreading systemically. The virus replicates in the reticulo-endothelial system and can be found in the liver, spleen, lung and kidney. By day 3 or 4, post inoculation, mice begin losing weight and become lethargic. Mice continue to lose weight and their general appearance declines with most animals exhibiting signs of severe disease such as ruffled fur, hunched posture and unsteady gate. By day 8, mice are moribund and have lost as much as 30% of their initial body weight. Mortality is the primary end-point in this model with 100% of untreated mice succumbing by day 9 post inoculation. Disease progression can be monitored by measuring the change in weight during the course of infection. The change in weight correlates with systemic replication of the vaccinia virus in mice and is a noninvasive method of determining disease severity (Law, M. et al. (2001) "*Antibody Neutralization Of The Extracellular Enveloped Form Of Vaccinia Virus*," Virology 280(1):132-142). The percentage weight change is useful for determining disease severity when treatment protects mice from lethal infection. To quantify the level of virus spread, animals must be sacrificed at selected time points post infection and virus titers measured in the liver, spleen, lung, kidney and other organs (Jordan, R. et al. (2006) "*Smallpox Antiviral Drug Development: Satisfying The Animal Efficacy Rule*," Expert Rev. Anti. Infect. Ther. 4(2):277-289).

Murine Vaccinia Virus Challenge Studies.

Figure 5:
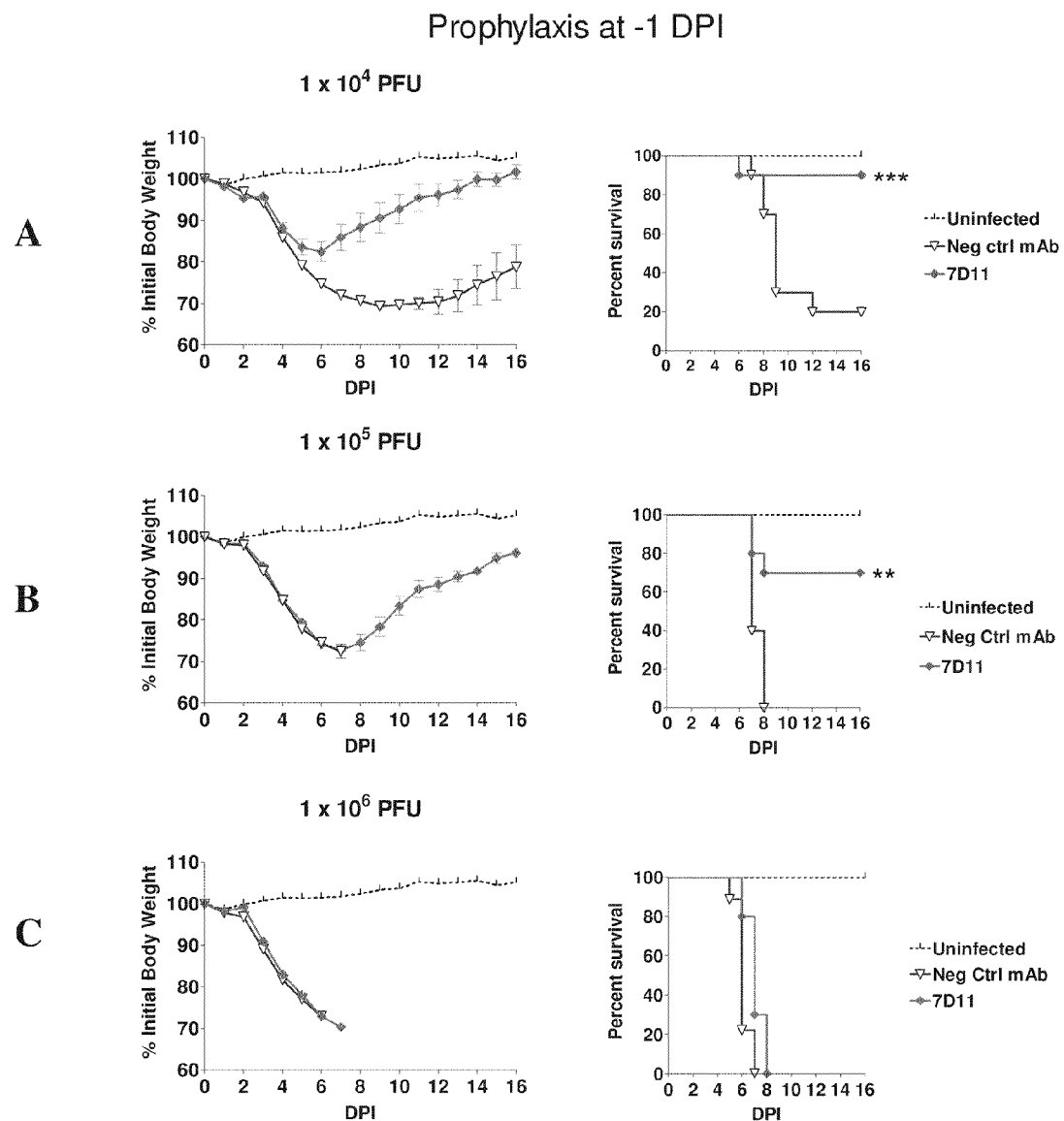
FIG. 5 (Panels A-C) shows the results of experiments on the prophylactic activity of 7D11 in intratracheal vaccinia virus-infected mice. 7D11 or negative control mAb were administered at 5 mg/kg by IP injection 1 day prior to infection with $1 \times 10^4$ (Panel A), $1 \times 10^5$ (Panel B) or $1 \times 10^6$ (Panel C) pfu vaccinia virus. There were 10 animals per group. Animals were monitored for weight loss (Panels A-C, left) and survival (Panels A-C, right). Because of animal mortality, the weight recovery curves are derived from variable numbers of animals. Survival curves were generated using the Kaplan-Meier method and differences between curves were compared using the log-rank statistic. *$P<0.05$, $P<0.01$, *$P<0.001$; compared to the negative control group.

The above-described Murine Vaccinia Virus Challenge Model was used to assess the in vivo neutralization activity of Ch7D11, Ch8A, Ch12F and Ch6C. Accordingly, BALB/c mice are subjected to an intratracheal vaccinia virus (strain WR) challenge. The intratracheal route was selected because it was found to be more reproducible than the intranasal route. FIG. 5, Panels A-C exemplify a virus titration study in which mice received 7D11 or negative control mAb by IP injection one day prior to intratracheal challenge. When challenged with virus at $1 \times 10^4$ pfu, the control mice exhibited substantial (~30%) weight loss and mortality (~80%), whereas, in mice pre-treated with 7D11 at 5 mg/kg, the maximal weight loss was reduced by half and mortality was lowered to 10%. When challenged with virus at $1 \times 10^5$ pfu, prophylactic administration of 7D11 did not reduce the extent of weight loss, but it improved survival from 0 to 70%. When challenged with virus at $1 \times 10^6$ pfu, prophylactic treatment of 7D11 had no effect on weight loss or survival.

The data from this study confirm that 7D11, the parental murine mAb, neutralized vaccinia virus in vivo. For the evaluation of the neutralizing activity of the chimeric mAbs, a robust virus challenge dose ($1 \times 10^5$ pfu) was selected for all subsequent studies. This dose caused rapid and extensive weight loss and 100% mortality in control animals.

Intratracheal inoculation of vaccinia virus infection provides a more severe challenge to mice than intranasal inoculation. This infection model provides a stronger virus challenge than the intranasal model used in the previously cited studies. This is evidenced by the fact that 250 mg/kg VIG provided substantial therapeutic activity in the intranasal challenge studies (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17): 8989-8995), whereas 500 mg/kg VIG provided no detectable therapeutic activity in the intratracheal challenge studies (FIG. 15, Panel D).

In the intratracheal model, mice exhibit an approximately 10% weight loss by day 3 post infection, which is an overt sign of viral disease. By contrast, in the intranasal model, an approximately 5% weight loss is not evident until day 4 post infection (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995; Lustig, S. et al. (2004) "*Synergistic Neutralizing Activities Of Antibodies To Outer Membrane Proteins Of The Two Infectious Forms Of Vaccinia Virus In The Presence Of Complement*," Virology 328(1):30-35).

Example 11

Prophylactic Activity of Chimeric mAbs Alone and in Combination

Figure 6:
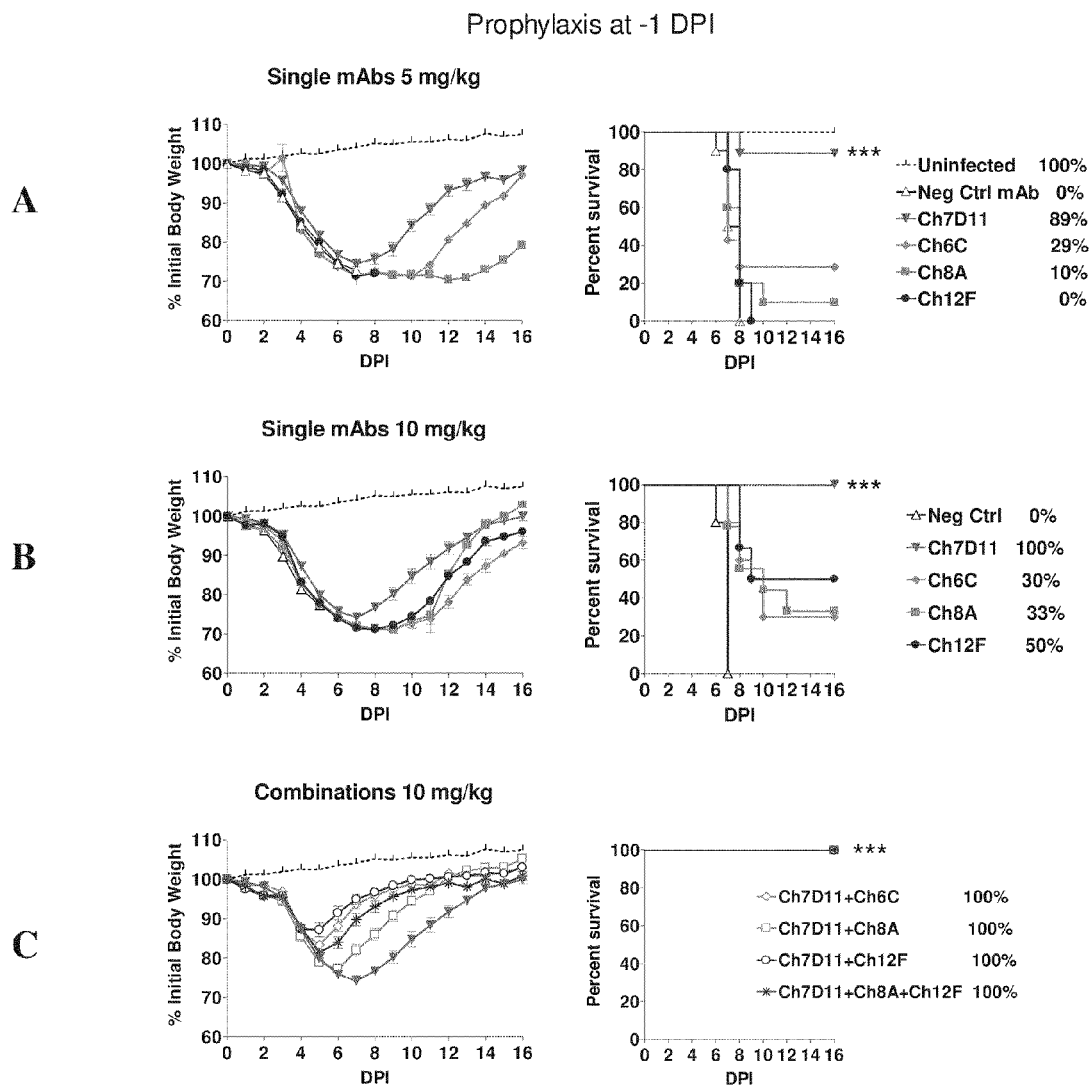
FIG. 6 (Panels A-C) shows the results of experiments on the prophylactic activity of single mAbs Ch7D11, Ch6C, Ch8A and Ch12F, and mAb combinations Ch7D11+Ch6C; Ch7-D11+Ch8A; Ch7-D11+Ch12F; and Ch7-D11+Ch8A+Ch12F in mice against intratracheal challenge with vaccinia virus. Single mAbs at a dose of 5 (Panel A) or 10 (Panel B) mg/kg and 1:1 mAb combinations at a total dose of 10 mg/kg (Panel C) were administered by IP injection 1 day prior to virus infection with $1 \times 10^5$ pfu with vaccinia virus. There were 10 animals per group. Animals were monitored for weight loss (Panels A-C, left) and survival (Panels A-C, right). Because of animal mortality, the weight recovery curves are derived from variable numbers of animals. Survival curves were generated using the Kaplan-Meier method and differences between curves were compared using the log-rank statistic. *$P<0.05$, $P<0.01$, *$P<0.001$; compared to the negative control group.

Individual chimeric mAbs at 5 or 10 mg/kg or combinations of mAbs at a total dose of 10 mg/kg were administered to mice one day prior to challenge with $1 \times 10^5$ pfu vaccinia virus. The individual mAb with the most potent prophylactic activity was Ch7D11, which modestly improved the weight loss pattern relative to the other groups and strongly reduced mortality from 0% to 90-100% (FIG. 6, Panel A; FIG. 6, Panel B). The in vivo neutralizing activity of Ch7D11 was similar to that of 7D11 (FIG. 5, Panels A-C). By contrast, the other chimeric mAbs (Ch6C, Ch12F and Ch8A) were less potent, resulting in no noticeable improvements in weight loss and only partial improvements in survival: 0-29% at 5 mg/kg and 30-50% at 10 mg/kg. In most cases, the 10 mg/kg dose was more effective than the 5 mg/kg dose.

The data are consistent with the hypothesis that anti-MV mAbs (Ch7D11) are more active prophylactically than anti-EV mAbs (Ch6C, Ch12F and Ch8A). However, there is clearly a role for anti-MV mAbs in prophylaxis, because combinations of Ch7D11 and an anti-EV mAb were more potent than Ch7D11 by itself (FIG. 6, Panel C). This is evidenced by the fact that all of the combinations noticeably reduced the extent of weight loss and completely protected the animals from mortality. Based on the extent of reduction in weight loss, the mAb combinations that targeted the A33 protein of the MV particle (Ch7D11:Ch12F and Ch7D11:Ch6C) were more potent than the one that targeted the B5 protein (Ch7D11:Ch8A). The triple combination (Ch7D11:Ch12F:Ch8A) was not more active than the most potent double combinations. In summary, these data show that a combination of anti-MV and anti-EV mAbs has greater prophylactic activity than any of the tested mAbs, employed individually.

Figure 7:
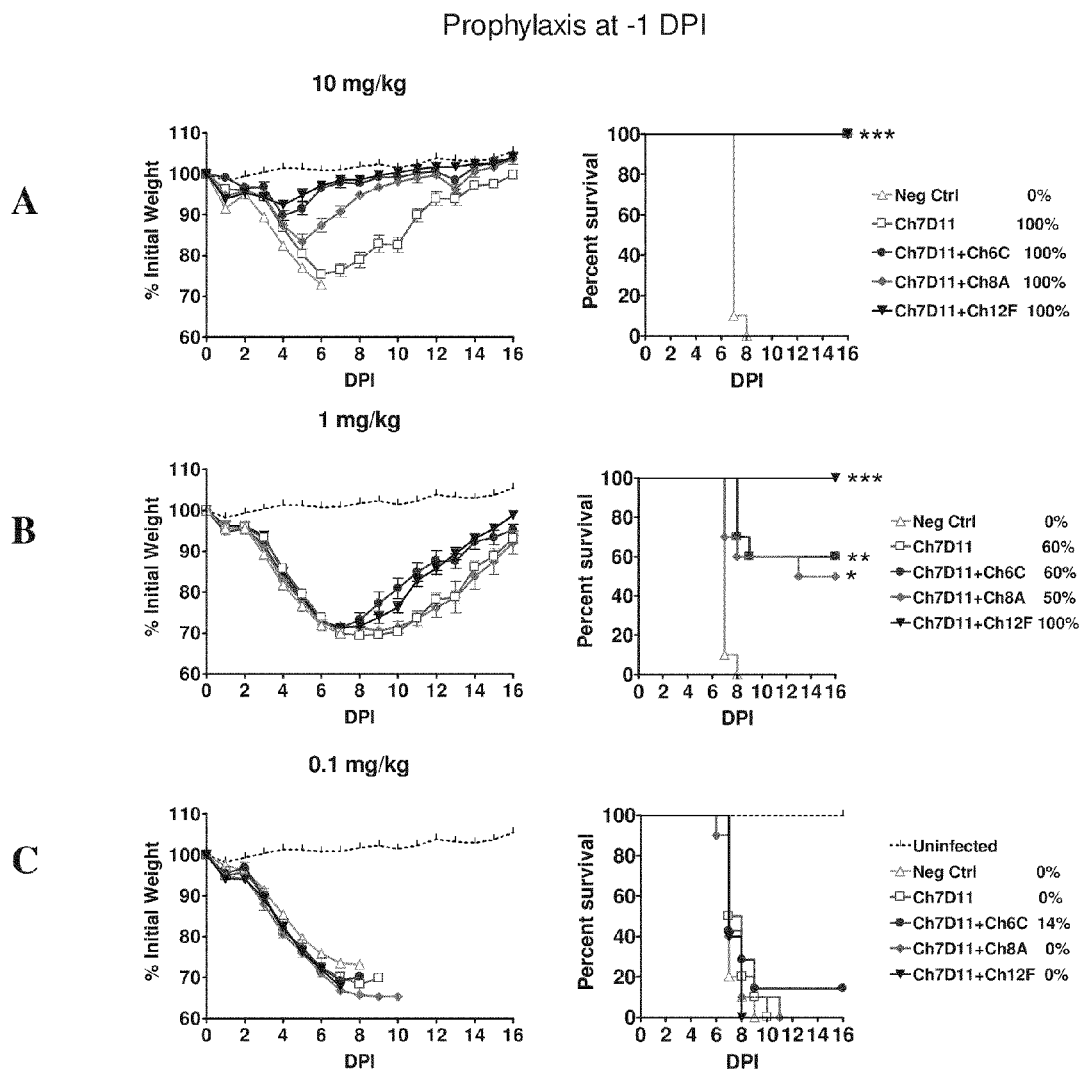
FIG. 7 (Panels A-C) shows the results of experiments on the prophylactic activity in vaccinia virus challenged mice. Single mAb Ch7D11 was tested with 1:1 mAb combinations Ch7D11+Ch6C; Ch7D11+Ch8A; and Ch7D11+Ch12F at total doses of 0.1 (Panel A), 1 (Panel B) or 10 (Panel C) mg/kg were administered by IP injection 1 day prior to virus infection with $1 \times 10^5$ pfu with vaccinia virus. There were 10 animals per group. Animals were monitored for weight loss (Panels A-C, left) and survival (Panels A-C, right). Because of animal mortality, the weight recovery curves are derived from variable numbers of animals. Survival curves were generated using the Kaplan-Meier method and differences between curves were compared using the log-rank statistic. *$P<0.05$, $P<0.01$, *$P<0.001$; compared to the negative control group.

A dose response study of the prophylactic activity of Ch7D11 alone or combined with Ch6C, Ch12F or Ch8A is shown in FIG. 7, Panels A-C. The 10 mg/kg data (FIG. 7, Panel A) exactly reproduced the data from the previous study (FIG. 6, Panel C), thereby supporting the conclusion that Ch7D11:Ch12F and Ch7D11:Ch6C are the most potent mAb combinations. The 1 mg/kg data (FIG. 7, Panel B) show complete protection (0% mortality) with Ch7D11:Ch12F, 40-50% mortality with Ch7D11:Ch6C or Ch7D11:Ch8A, and 100% mortality with Ch7D11 alone. These data indicate that Ch7D11:Ch12F is the most potent combination, and confirm that a combination of anti-EV and anti-MV mAbs is more potent than an individual mAb. At 0.1 mg/kg, there was no evidence of any neutralizing activity (FIG. 7, Panel C). Thus, the antibody was prophylactically effective even at a dose of between 0.1 and 1 mg/kg.

Example 12

Post-Exposure Treatment Activity of Mab Combinations

Studies have demonstrated post-exposure prophylactic activity when chimeric anti-A33 or anti-B5 mAbs were administered at 2 days following intranasal inoculation, a time that precedes any noticeable signs of disease, such as weight loss (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995; Lustig, S. et al. (2004) "*Synergistic Neutralizing Activities Of Antibodies To Outer Membrane Proteins Of The Two Infectious Forms Of Vaccinia Virus In The Presence Of Complement*," Virology 328(1):30-35). Because the anti-MV+anti-EV mAb combinations were more potent than single mAbs, they were subjected to a more rigorous test: administered at 3 days following intratracheal inoculation, at which time infected mice exhibit an approximately 10% loss in mean weight (see FIG. 5, Panels A-C; FIG. 6, Panels A-C; FIG. 7, Panels A-C), which is an overt sign of viral disease. Thus, administration of the mAbs at 3 days post infection following intratracheal inoculation constitutes a test of post-exposure treatment activity.

Figure 8:
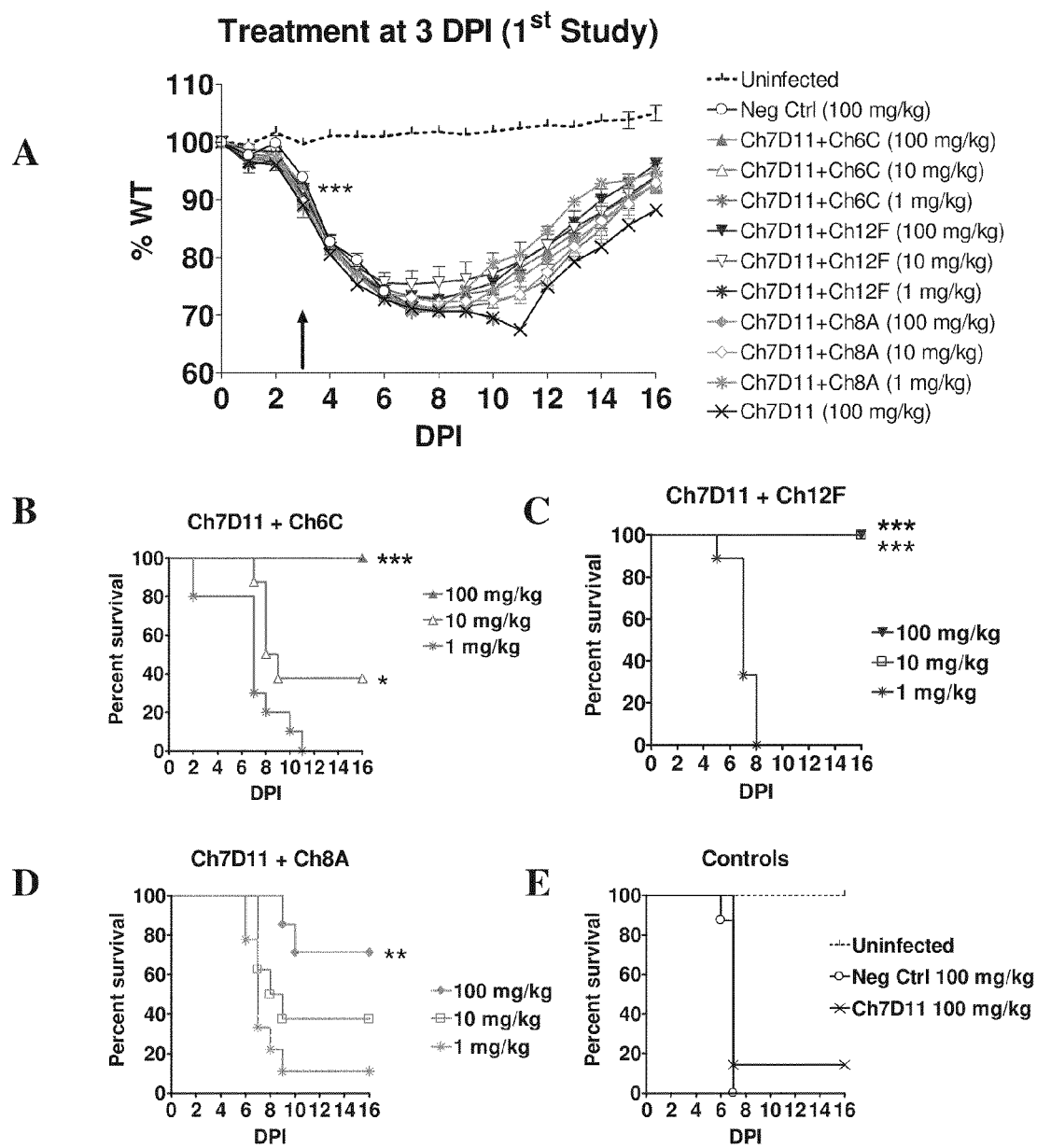
FIG. 8 (Panels A-E) shows the results of a $1^{st}$ study of treatment at 3 days post infection: dose response study. Panel A: percent weight change vs. days post infection (DPI). Percent survival with different antibodies (Ch7D11/Ch6c, Panel B; Ch7D11/Ch12F, Panel C; Ch7D11/Ch8A, Panel D) and with controls (Panel E) is shown. Mice were inoculated intratracheally with $1.25 \times 10^5$ pfu vaccinia virus. At 3 days post infection, after animals had exhibited a 10% weight loss, single mAbs or 1:1 mAb combinations at a total dose of 1, 10 or 100 mg/kg were administered by IP injection. There were 10 animals per group. Animals were monitored for weight loss and survival. Because of animal mortality, the weight recovery curves are derived from variable numbers of animals. The average % weight loss at 3DPI was 8.2% ($P<0.001$, compared to the uninfected group). Survival curves were generated using the Kaplan-Meier method and differences between curves were compared using the log-rank statistic. *$P<0.05$, $P<0.01$, *$P<0.001$; compared to the negative control group.

In a "$1^{st}$" post-exposure treatment study (FIG. 8, Panels A-E), individual mAbs or combinations of mAbs were administered at doses of 1, 10 or 100 mg/kg to mice at 3 days post infection (DPI). At this time, there was a substantial weight loss in infected mice relative to uninfected mice (mean change from baseline of −8.47% and −0.30%, respectively; P<0.001). The treatment with mAbs did not cause noticeable changes in the shapes of the weight curves (FIG. 8, Panel A). This was expected since the infections were advanced at the time of treatment. When administered at 100 mg/kg, all three mAb combinations provided substantial protection from mortality relative to a negative control mAb, which provided no protection; 100% protection was conferred by Ch7D11:Ch12F (FIG. 8, Panel C) or Ch7D11:Ch6C (FIG. 8, Panel B) and 70% protection by Ch7D11:Ch8A (FIG. 8, Panel D). No protection was observed when Ch7D11 alone was administered at 100 mg/kg (FIG. 8, Panel E). When administered at 10 mg/kg, Ch7D11:Ch12F conferred 100% survival (FIG. 8, Panel C), whereas Ch7D11:Ch6C and Ch7D11:Ch8A resulted in 30-40% survival (FIG. 8, Panel B and FIG. 8, Panel D, respectively). When administered at 1 mg/kg, little to no protection was observed with any of the mAb combinations (FIG. 8, Panels B-D). Relative to the negative control mAb group, survival was significantly different at 10 and 100 mg/kg for Ch7D11:Ch12F (P=0.0009 and 0.0003, respectively), at 10 and 100 mg/kg for Ch7D11:Ch6C (P=0.0003 and 0.014, respectively) and at 100 mg/kg for Ch7D11:Ch8A (P=0.005) but not at 10 mg/kg (P=0.091). No statistically significant improvements in survival were observed at 1 mg/kg. The data indicate that Ch7D11:Ch12F is the most potent combination for therapeutic activity and that the combination was prophylactically effective even at a dose of between 1 and 10 mg/kg.

Figure 9:
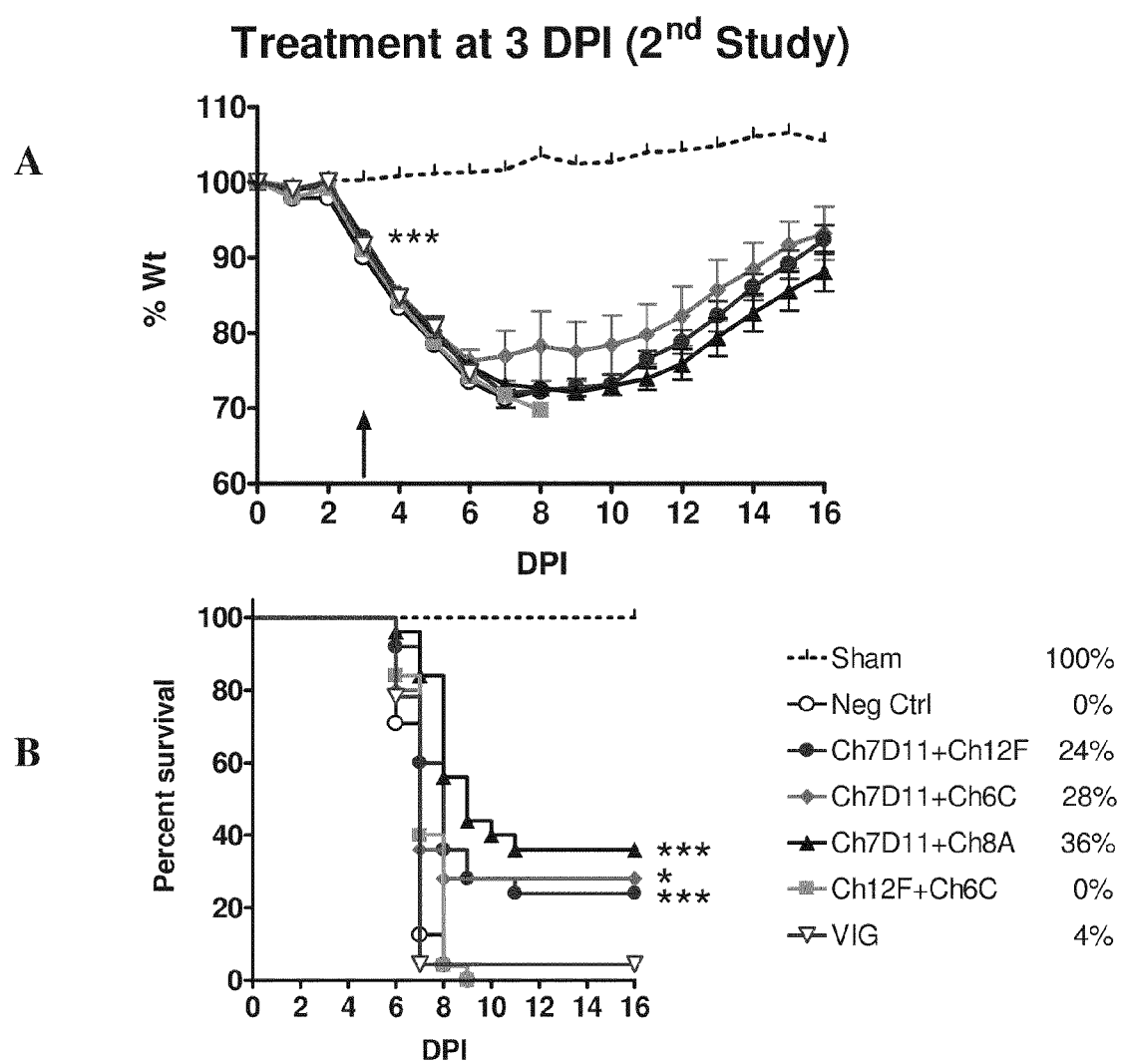
FIG. 9 (Panel A-B) shows the results of a $2^{nd}$ study of treatment at 3 days post infection: dose response study. Panel A: percent weight change vs. days post infection (DPI). Panel B: percent survival with different antibody combinations (Ch7D11/Ch6C; Ch7D11/Ch12F; Ch7D11/Ch8A; Ch12F/Ch6c) or with controls is shown. Mice were inoculated intratracheally with $1.25 \times 10^5$ pfu vaccinia virus. At 3 days post infection, after animals had exhibited an approximately 8% weight loss, mAb combinations at a total dose of 10 mg/kg or VIG at 500 mg/kg were administered by IP injection. There were 25 animals per group. Animals were monitored for weight loss and survival. Because of animal mortality, the weight recovery curves are derived from variable numbers of animals. The average % weight loss at 3DPI was 8.6% ($P<0.001$, compared to the uninfected group). Survival curves were generated using the Kaplan-Meier method and differences between curves were compared using the log-rank statistic. *$P<0.05$, $P<0.01$, *$P<0.001$; compared to negative control group.

In a "2nd" post-exposure treatment study (FIG. 9, Panels A-B), infected mice were treated at 3 DPI with mAb combinations at 10 mg/kg or VIG (vaccinia immune globulin) at 500 mg/kg. The 10 mg/kg mAb dose was selected for this study, because it was the most discriminating dose in the previous study. The VIG dose of 500 mg/kg was selected, because this dose is the highest one recommended for clinical use by the VIG manufacturer (Cangene and Dynport). As in the $1^{st}$ study, there was a substantial weight loss in infected mice relative to uninfected mice at 3 DPI (mean change from baseline of −8.29% and +0.30%, respectively; P<0.001) (FIG. 9, Panel A). Significant protection (24-38% survival) was observed with three anti-MV:anti-EV combinations, Ch7D11:Ch12F, Ch7D11:Ch6C and Ch7D11:Ch8A (P=0.0002, 0.014 and <0.0001, respectively, relative to the negative control mAb) (FIG. 9, Panel B). In contrast, no protection was observed with Ch8A:Ch12F, a combination of two anti-EV mAbs, or with VIG at 500 mg/kg (FIG. 9, Panel B). The data confirm that anti-MV+anti-EV mAb combinations exhibit therapeutic activity in vaccinia virus-infected mice. However, in contrast to the previous study, the data from this study suggest that combinations with Ch12F, Ch6C or Ch8A as the anti-EV component have comparable activities. Additional studies will be needed to discriminate them. Finally, the data, although preliminary, demonstrate that combinations of anti-MV and anti-EV mAbs were at least 50-fold more potent than VIG.

Figure 10:
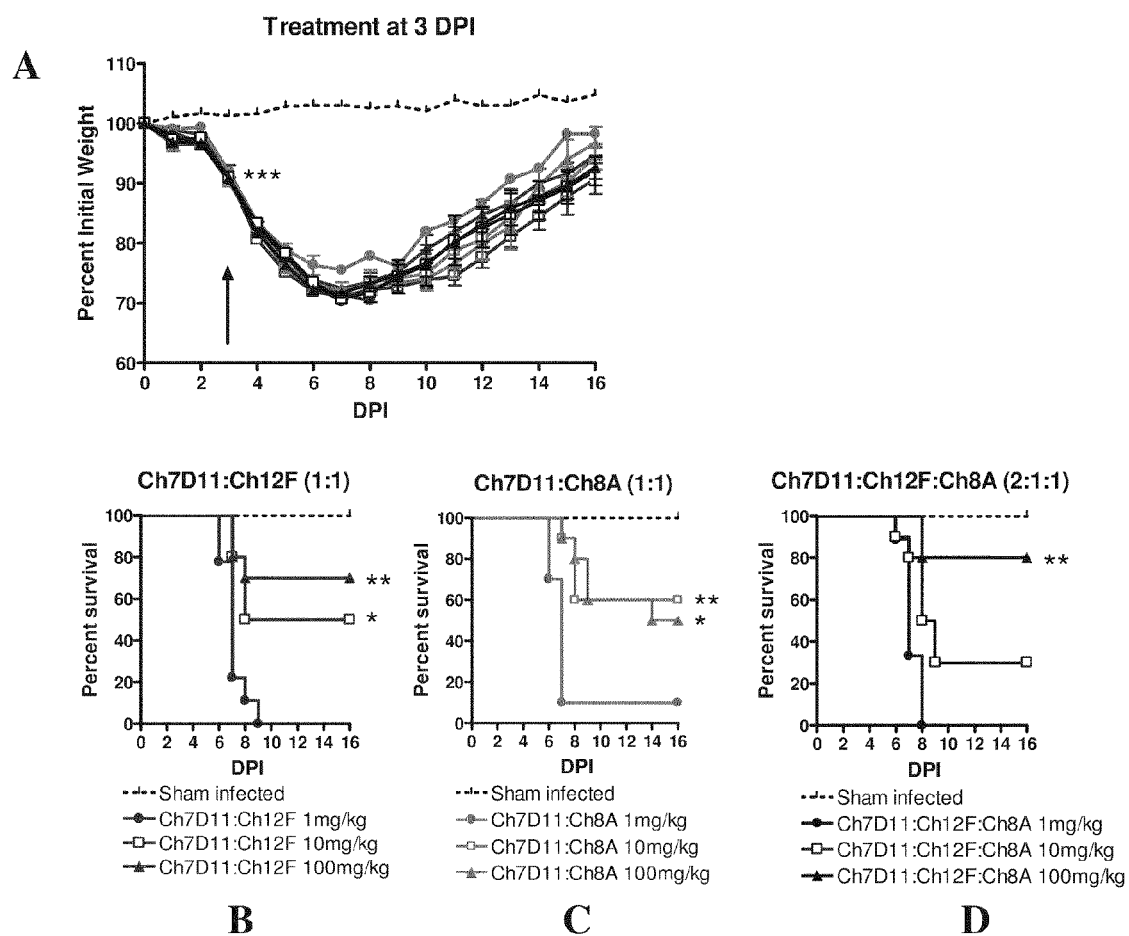
FIG. 10 (Panel A-D) shows the results of a $3^{rd}$ study of treatment at 3 days post infection: dose response study. Panel A: percent weight change vs. days post infection (DPI). Percent survival is shown with three mAbs mixtures: Ch7D11:Ch12F (1:1) (Panel B), Ch7D11:Ch8A (1:1) (Panel C) and Ch7D11:Ch12F:Ch8A (2:1:1) (Panel D). Mice were inoculated intratracheally with $1.25 \times 10^5$ pfu vaccinia virus. At 3 days post infection, after animals had exhibited an approximately 8% weight loss, mAb combinations at a total dose of 1, or 100 mg/kg were administered by IP injection. There were 10 animals per group. Animals were monitored for weight loss and survival. Because of animal mortality, the weight recovery curves are derived from variable numbers of animals. Survival curves were generated using the Kaplan-Meier method and differences between curves were compared using the log-rank statistic. *$P<0.05$, $P<0.01$, *$P<0.001$; compared to the 1 mg/kg dose groups.

In a "$3^{rd}$" post-exposure treatment study (FIG. 10, Panel $10^{-10}$), infected mice were treated at 3 DPI with mAb combinations at 1, 10 or 100 mg/kg. As in the $1^{st}$ and $2^{nd}$ studies, there was a substantial weight loss in infected mice relative to uninfected mice prior to treatment at 3 DPI (the mean change from baseline was −8.83% and +0.61%, respectively; P<0.001) (FIG. 10, Panel A). In this study, 2- and 3-component cocktails were tested to determine if cocktails with Ch7D11 and different anti-EV mAbs would have improved potency. The three mAbs cocktails tested were: Ch7D11:Ch12F (1:1) (FIG. 10, Panel B), Ch7D11:Ch8A (1:1) (FIG. 10, Panel C) and Ch7D11:Ch12F:Ch8A (2:1:1) (FIG. 10, Panel D). The ratio of anti-MV and anti-EV mAbs in each cocktail was 1:1. Each cocktail exhibited similar therapeutic activity at the three dose levels tested; survival was 50-80% at the 100 mg/kg dose, 30-60% at the 10 mg/kg dose, and 0-10% at the 1 mg/kg dose. The cocktails with Ch12F, Ch8A or both as the anti-EV mAb component had similar potencies. Thus, a 3-component cocktail was not more potent than a 2-component cocktail.

Cocktails of anti-MV and anti-EV mAbs were thus found to be highly effective in providing prophylactic treatment in a pre-exposure animal model as well as therapeutic treatment in a post-exposure animal model. All of the therapeutic/prophylactic compositions that contained Ch7D11 as the anti-MV mAb and Ch12F, Ch6C or Ch8A as the anti-EV mAb exhibited similar potency. As expected, the doses required for efficacy in post-exposure treatment studies were higher than those required in pre-exposure prophylaxis studies. Of the three anti-EV mAbs, Ch12F and Ch8A are preferred, because they exhibit higher affinity binding than Ch6C (Table 3). When Ch12F and Ch8A are compared, Ch12F is preferred because Ch7D11:Ch12F tended to exhibit higher activity than Ch7D11:Ch8A in both pre-exposure prophylactic (FIG. 11, Panel A) and post-exposure treatment (FIG. 11, Panel B) studies. In addition, the expression level from stable transfected CHO cell pools for Ch12F was >2-fold higher than for Ch8A (Table 2). Based on these considerations, Ch12F is considered the preferred anti-EV mAb for the present invention. A preferred composition for prophylactic or therapeutic treatment comprises antibodies $CH_7D11$ and Ch12F, and more preferably, h7D11 and Ch12F.

Example 13

Ectromelia Virus Challenge Studies in Mice

Ectromelia virus is a laboratory pathogen of mice (Esteban, D. J. et al. (2005) "*Ectromelia Virus: The Causative Agent Of Mousepox*," J. Gen. Virol. 86(10):2645-2659; Schriewer, J. et al. (2004) "*Mouse Models For Studying Orthopoxvirus Respiratory Infections*," *Methods Mol. Biol.* 269:289-308; Buller, R. M. et al. (1991) "*Poxvirus Pathogenesis*," *Microbiol. Rev.* 55(1):80-122; Baxby, D. (1975) "*Identification And Interrelationships Of The Variola/Vaccinia Subgroup Of Poxviruses*," Prog. Med. Virol. 19:215-246). The pathogenesis of ectromelia virus disease closely resembles human smallpox, with distinct stages of localized replication, systemic virus spread and lesion formation. However, the time course of infection and disease progression is much shorter (Jordan, R. et al. (2006) "*Smallpox Antiviral Drug Development: Satisfying The Animal Efficacy Rule,*" *Expert Rev. Anti. Infect. Ther.* 4(2):277-289).

The natural route of ectromelia infection is through abrasions in the skin and the virus replicates in local lymphoid cells. The virus multiplies in the lymphatic endothelial cells, macrophages and lymphocytes within the node over a period of 2-4 days. Following this latency period, the virus spreads through the lymph and enters the bloodstream to cause a primary viremia. The virus is rapidly removed by macrophages lining the sinusoids of the liver, spleen and bone marrow. Infection of parenchymal cells of liver and lymphoid cells of the spleen produces high virus titers that are released into the bloodstream to cause a secondary viremia. In highly susceptible animals, replication in the liver and spleen produces focal necrotic lesions, acute hepatitis and multiorgan failure. In mice that are less susceptible, a rash develops following the secondary viremia. The rash is caused by virus replication in the perivascular cells, dermal endothelia cells and epidermis.

In susceptible mice less than 1 PFU of ectromelia virus causes lethal infection. For the purposes of studying the progress and consequences of infection, mice are typically inoculated with ectromelia virus either by footpad scarification (which is similar to the natural route of infection), or by intranasal delivery. The virus multiplies in the lymphatic endothelial cells, macrophages and lymphocytes within the regional node over a period of 2-4 days. By day 4 post inoculation, animals appear ill with hunched posture, ruffled coat and increased respiration. Viral replication in the liver and spleen and other internal organs cause death in the infected animals between days 6 and 10 post inoculation. Similar to the vaccinia virus/mouse model, disease progression can be monitored by measuring the change in weight during the course of infection. Thus, in this model, antiviral efficacy is measured by decreased mortality, inhibition of virus-induced weight loss and reduction of virus titers in liver, spleen and other tissues.

In order to assess the therapeutic capability of the compositions of the present invention, their ability to protect mice infected with ectromelia virus was investigated. This study utilized A/NCR mice (see, Buller, R. M. et al. (2004) "*Efficacy Of Oral Active Ether Lipid Analogs Of Cidofovir In A Lethal Mousepox Model,*" *Virology* 318(2):474-481), which are highly susceptible to ectromelia virus infection. In the experiment, the mice were inoculated intranasally with 0.6 PFU of ectromelia virus which results in 100% lethality.

Antibody Ch7D11, the anti-MV mAb, was expected to neutralize ectromelia virus because the epitope recognized by this antibody is 100% conserved between the two viruses (as discussed above). Anti-EV mAbs are also expected to be able to neutralize ectromelia virus given the high level of conservation in the epitope region, although differences in the epitopes might prevent or attenuate the relevant cross-reactivity. To maximize the possibility of observing a strong neutralizing activity in ectromelia-infected mice, a 3:1:1:1 mixture of antibodies h7D11:Ch12F:Ch6C:Ch8A is administered to the A/NCR mice. This mixture is a 1:1 combination of anti-MV and anti-EV mAbs. Upon the recognition of desired protection, pairs of anti-MV and anti-EV mAbs are evaluated for their efficacy.

The 3:1:1:1 mixture of antibodies h7D11:Ch12F:Ch6C: Ch8A was administered at dose levels of 1, 10 or 100 mg/kg to mice by IP injection at 24 hours before or 24 hours after ectromelia virus infection according to the regimen shown in Table 4. Mice were also administered cidofovir, a known antiviral agent, at a dose level of 100 mg/kg as a positive control.

TABLE 4

| Cage | No. of mice | Virus | Article | Dose (mg/kg) | Time (h) | Day of Death | Mortality |
|---|---|---|---|---|---|---|---|
| 1 | 5 | − | vehicle | NA | −24 | | 0% |
| 2 | 5 | + | vehicle | NA | −24 | 8, 9, 9, 9, 10 | 100% |
| 3 | 5 | + | mAb cocktail | 1 | −24 | 10, 11, 14 | 60% |
| 4 | 5 | + | mAb cocktail | 1 | +24 | 11, 15 | 40% |
| 5 | 5 | + | mAb cocktail | 10 | −24 | | 0% |
| 6 | 5 | + | mAb cocktail | 10 | +24 | | 0% |
| 7 | 5 | + | mAb cocktail | 100 | −24 | | 0% |
| 8 | 5 | + | mAb cocktail | 100 | +24 | | 0% |
| 9 | 5 | + | CDV | 100 | −24 | | 0% |
| 10 | 5 | + | CDV | 100 | +24 | | 0% |

Figure 11:
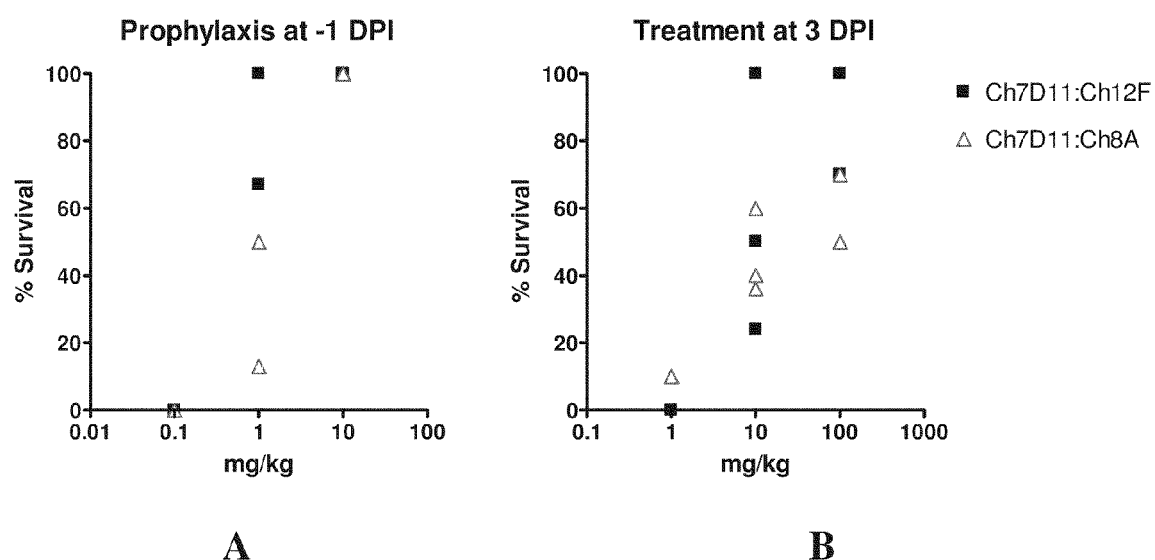
FIG. 11 (Panels A-B) summarizes the prophylactic and treatment activities of Ch7D11:Ch12F and Ch7D11:Ch8A. Panel A shows data from three pre-exposure prophylaxis studies in which mAb cocktails were administered one day prior to intratracheal vaccinia virus infection. Panel B shows data from three post-exposure treatment studies in which mAb cocktails were administered at 3 days post infection.

50 A/NCR female mice; 0.6 PFU ectromelia virus (intranasal) per mouse; CDV = cidofovir; mAb cocktail = 1:1 mixture of anti-MV + anti-EV mAbs (Ch7D11:Ch12F:Ch6C:Ch8A, 3:1:1:1)
−24 indicates prophylactic administration 24 hours prior to viral infection
+24 indicates therapeutic administration 24 hours after viral infection The data show that partial protection (40-60% survival) is observed when mice received the 3:1:1:1 mixture of antibodies h7D11:Ch12F:Ch6C:Ch8A at 1 mg/kg at −24 h (40% survival) or +24 h (60% survival), and that full protection (100% survival and minimal to no weight loss) is observed when mice received these mAbs at 10 or 100 mg/kg at −24 h or +24 h (FIG. 12, Panels A and B; legend numbers 1-10 refer to cages described in Table 4, the curves of cages 1, 5-10 superimpose upon each other). Similar full protection was observed with cidofovir at 100 mg/kg. These data show that the mAb cocktail was effective in neutralizing ectromelia virus in mice and that the mAb dose response was similar to that observed with vaccinia virus in mice (FIG. 11, Panels A and B). Thus, the ectromelia virus/mouse model provides a valid "animal rule" efficacy model.

Example 14

Survival Dose Response Curves

When administered prophylactically at −1 DPI, Ch8A and Ch12F were associated with only partial survival, whereas Ch7D11 conferred full survival (FIG. 15, Panel A, FIG. 16). Ch7D11 slightly reduced the extent of weight loss (a measure of morbidity), whereas Ch8A and Ch12F did not. However, when a Ch7D11: Ch8A or Ch7D11: Ch12F combination was administered, mortality was completely prevented and the extent of weight loss was greatly reduced (FIG. 15, Panel A, FIG. 16). These data demonstrate the synergistic prophylactic activity of a combination of anti-MV and anti-EV mAbs When administered therapeutically at 2 DPI to mice subjected to a 5-fold lower virus challenge, Ch8A or Ch12F improved survival only slightly, whereas Ch7D11 substantially improved survival and partially reduced morbidity (FIG. 15, Panel B, FIG. 17). By contrast, administration of Ch7D11: Ch8A or Ch7D11: Ch12F combinations almost completely prevented death and greatly reduced morbidity. These data demonstrate the synergistic therapeutic activity of a combination of anti-MV and anti-EV mAbs.

Figure 18:
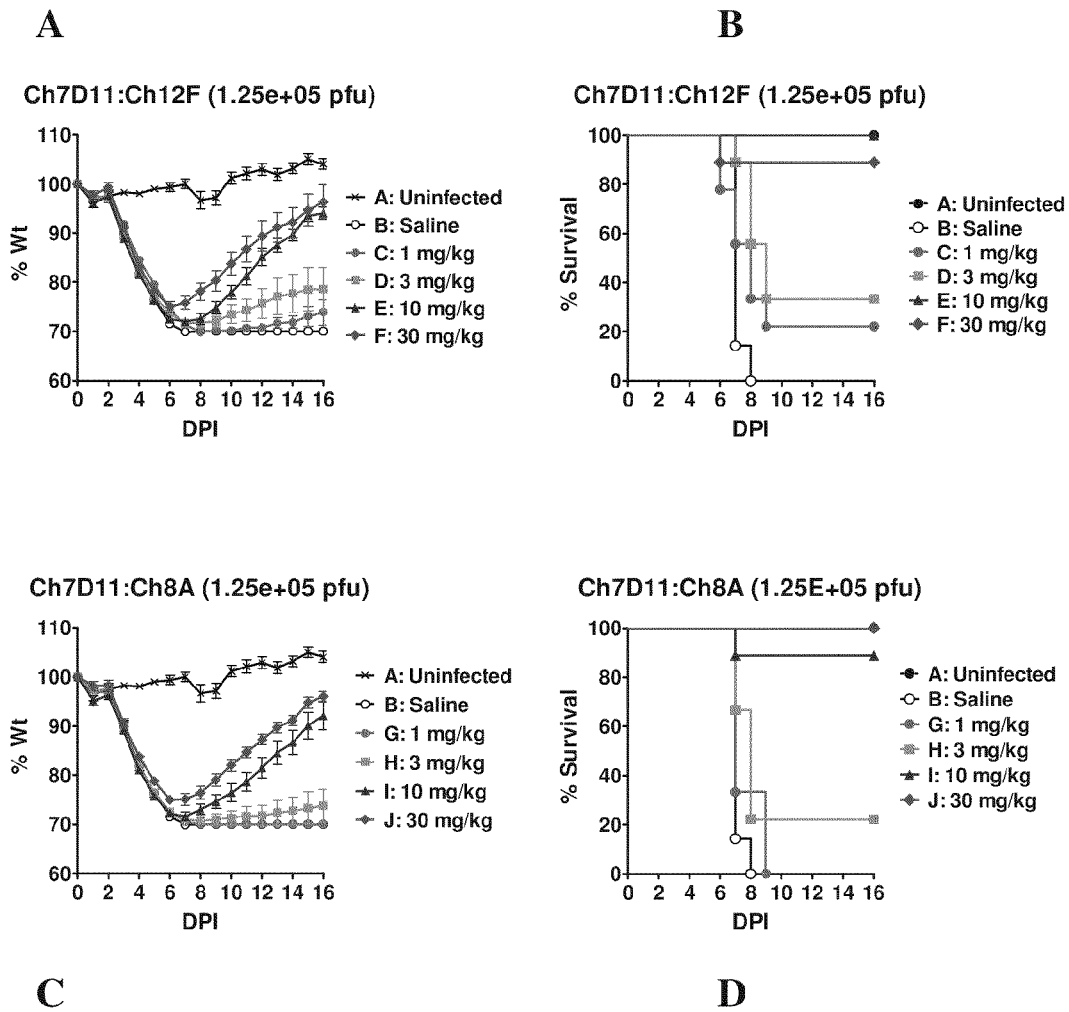
Figure 19:
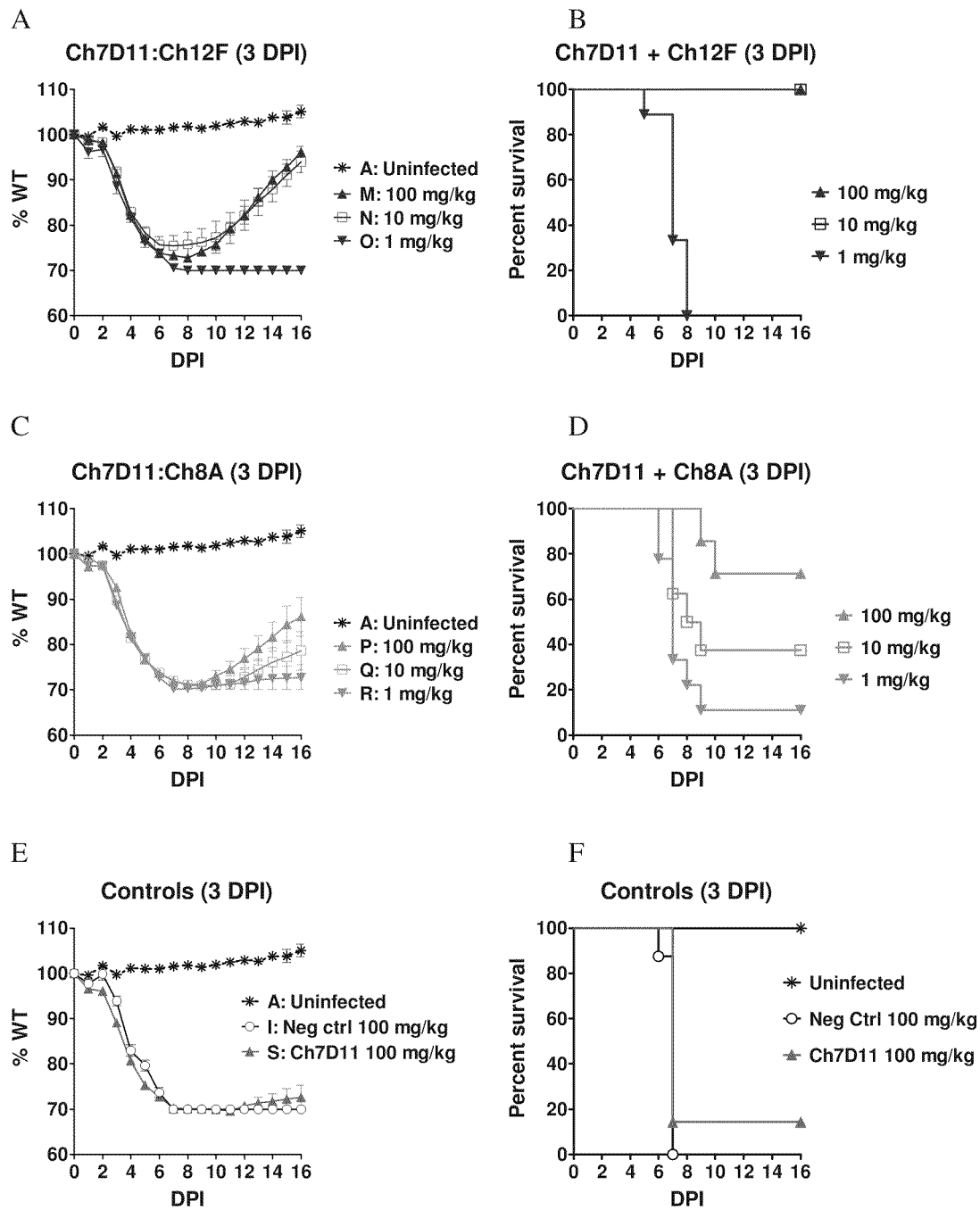
Figure 20A:
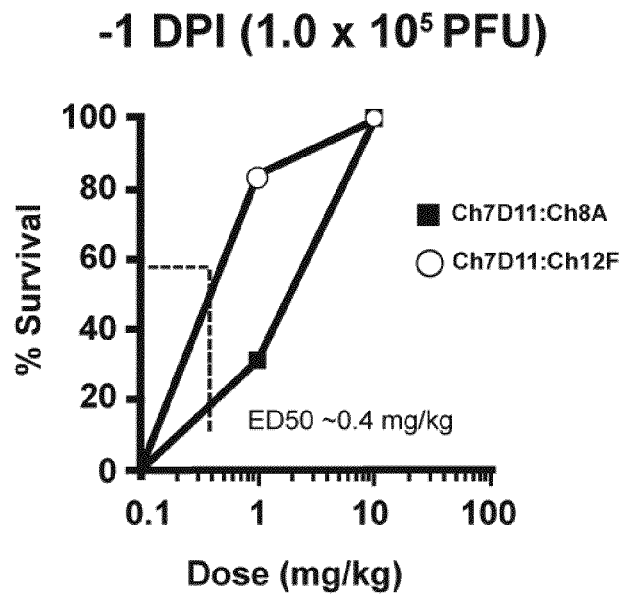
Figure 20B:
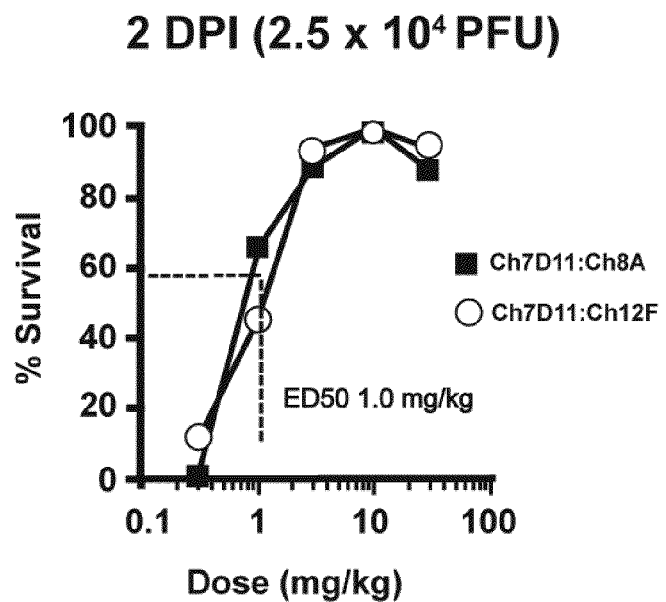
Figure 20C:
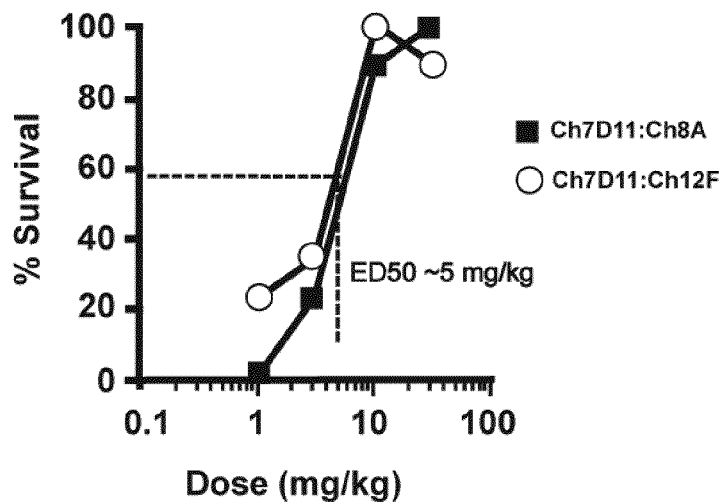
Figure 20D:
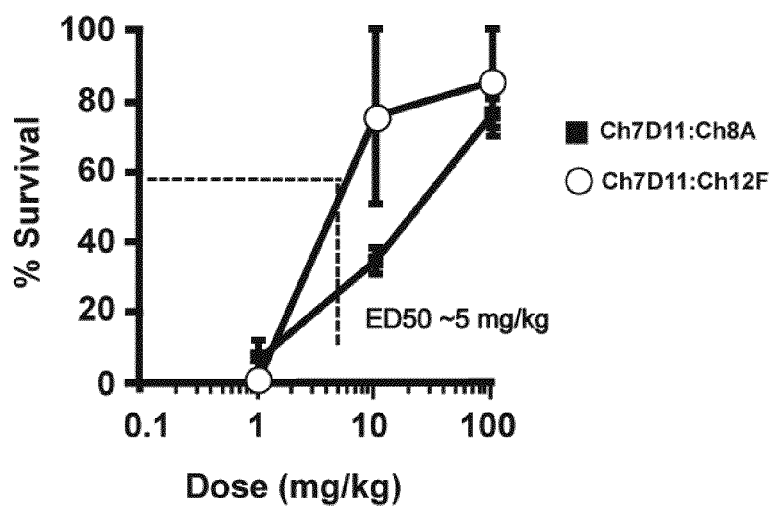

When administered therapeutically at 2 or 3 DPI to mice subjected to the standard virus challenge, the individual mAbs were completely ineffective at preventing death or reducing morbidity (FIG. 15 (Panels C-D), FIG. 18 and FIG. 19). By contrast, administration of Ch7D11:Ch8A or Ch7D11:Ch12F combinations were highly effective in preventing death and were partially effective in reducing morbidity in a dose dependent manner. The therapeutic efficacy observed with the mAb combinations administered at 3 DPI is particularly striking, because these animals exhibited a substantial weight loss (approximately 10%) prior to treatment. These data further substantiate the synergistic therapeutic activity of a combination of anti-MV and anti-EV mAbs.

The survival dose response curves for the prophylactic and therapeutic activities of Ch7D11:Ch12F and Ch7D11:Ch8A were similar, but Ch7D11:Ch12F generally tended to be slightly more potent (FIG. 20, Panels A-D). The ED50 (half-maximal effective dose) was approximately 0.4 mg/kg for Ch7D 11:Ch12F administered prophylactically at −1 DPI (FIG. 20, Panel A), which increased to approximately 5 mg/kg when administered therapeutically at 2 or 3 DPI (FIG. 20, Panels C-D). When the virus challenge dose was reduced 5-fold, the ED50 for Ch7D11:Ch12F administered at 2 DPI was also reduced 5-fold (FIG. 20, Panel B). Thus, in this infection model, the dose required for therapeutic activity was proportional to the magnitude of the virus challenge dose.

The mAb doses required to prevent morbidity (weight loss) are higher than those required to prevent mortality. When Ch7D11:Ch12F was administered at −1 DPI, complete prevention of death required a dose of 1 mg/kg, but nearly complete prevention of morbidity required a dose of 10 mg/kg (FIG. 16). When administered at 3 DPI, complete or nearly complete prevention of death occurred at a dose of 10 mg/kg, but the extent of weight loss was only slightly reduced, even at a dose as high as 100 mg/kg (FIG. 10). Thus, when mAb mixtures are administered at a late stage of infection (after the appearance of overt signs of disease, namely, 10% weight loss), they are highly effective at preventing death but less effective at ameliorating disease.

Figure 21:
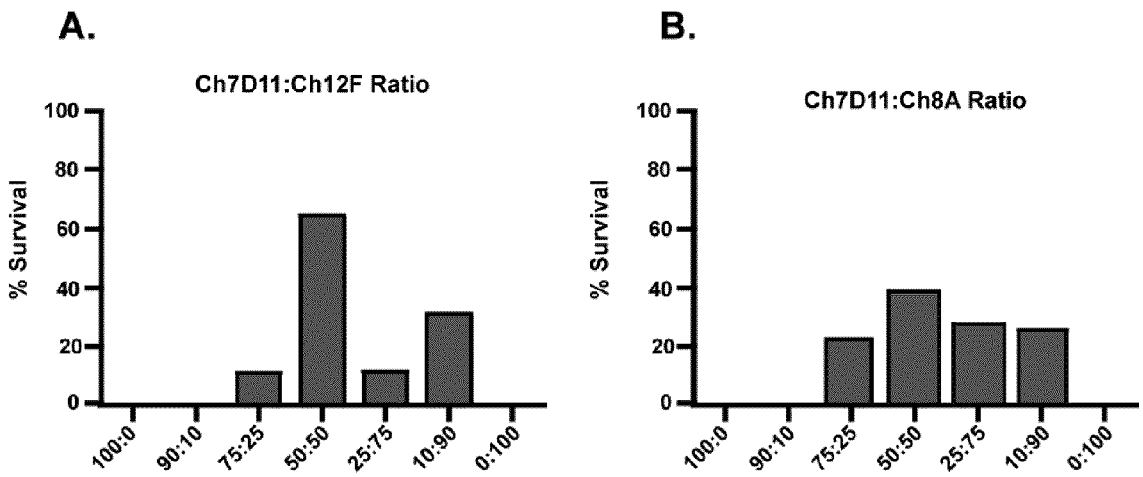

To determine the optimal mAb ratio for therapeutic activity, mAb mixtures at various ratios were administered at 2 DPI at 5 mg/kg, a dose that corresponds to the ED50 (FIG. 5C). For either Ch7D11:Ch12F or Ch7D11:Ch8A, the optimal ratio was 50:50 (FIG. 21).

In summary, combinations of anti-MV and anti-EV monoclonal antibodies exhibit synergistic prophylactic and therapeutic activity and are potent orthopoxvirus immunotherapeutic agents. The most potent combination is a 50:50 mixture of Ch7D11 (an anti-L1 mAb) and Ch12F (an anti-A33 mAb). The protective dose is dependent on the number of days post-infection and the magnitude of the virus challenge dose. For a Ch7D11:Ch12F combination administered therapeutically as late as 3 days following a strong virus challenge, the minimum dose for full or nearly full survival is 10 mg/kg.

Example 15

Ig DARTs

As discussed above, one aspect of the present invention relates to the use of immuno-protective dual affinity retargeting reagents ("DARTs"). While DART molecules retain the stability and highly specific binding afforded by an antibody platform, their small size and lack of the Fc region leads to rapid clearance and therefore to short serum half-life. Further, they are unable to recruit immune system components for various immune functions. Although these attributes permit DARTS to avoid causing long term immune system complications, they can be undesirable in situations in which long term immunity is desired.

To address these issues, platforms have been developed to display DARTs and other diabody molecules on antibody scaffolds (Wu, C. et at. (Epub 2007 Oct. 14) "*Simultaneous Targeting Of Multiple Disease Mediators By A Dual-Variable-Domain Immunoglobutin*," Nature Biotechnol. 25(11): 1290-1297; Asano, R. et al. (Epub 2007 Jul. 19) "*Highly Effective Recombinant Format Of A Humanized Igg-Like Bispecific Antibody For Cancer Immunotherapy With Retargeting Of Lymphocytes To Tumor Cells*," J. Biol. Chem. 282 (38):27659-27665). The constant regions of antibodies confer very high stability in circulation, allowing individual antibody proteins to persist for several weeks. Further, they allow recruitment of immune function to enhance activities such as antibody-dependent cell-mediated cytotoxicity and complement-mediated cytotoxicity (Marvin, J. S. et al. (2005) "*Recombinant Approaches to IgG-like Bispecific Antibodies*," Acta Pharmacol. Sin. 26(6):649-658). There are many possible configurations of bispecific components on antibody scaffolds. DART units have been successfully appended to the amino- and carboxy-termini of antibodies and antibody fragments.

Figure 22:
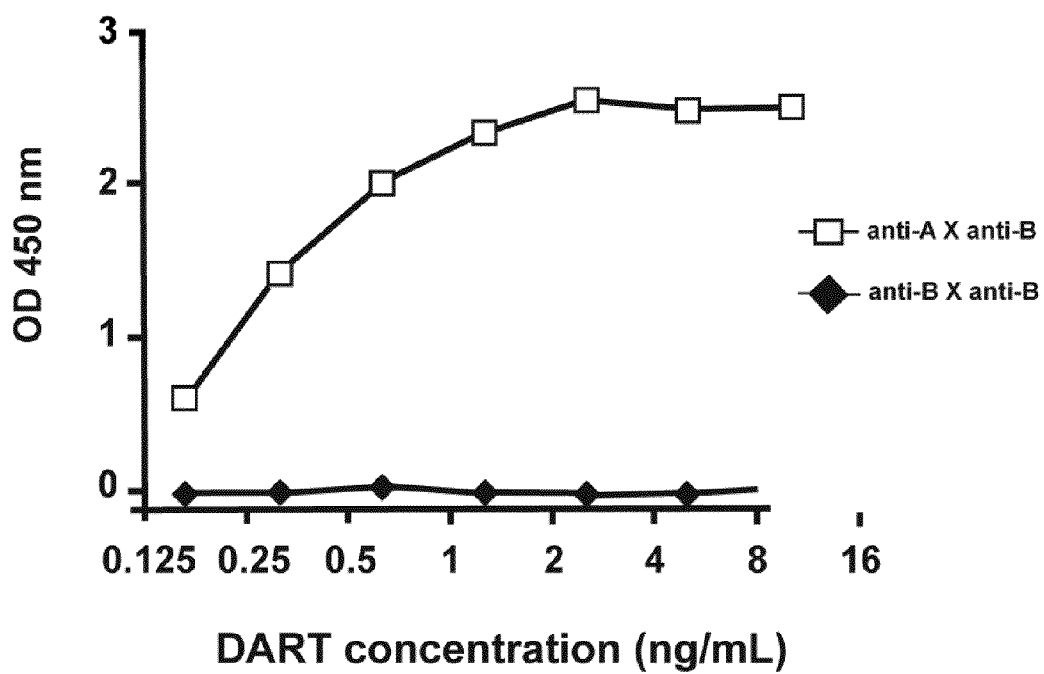

A DART chain was expressed as a C-terminal fusion to the Fc region of the heavy chain (after a (SEQ ID NO:42) GGGSGGGG linker sequence) and provided the second DART chain in trans. This FcDART (a type of IgDART) is expressed well (over 0.3 µg/ml in transient expression in 293H cells (typically improved a few hundred times in mAb-expressing cell line development) and is able to bind both of its antigens simultaneously (FIG. 22).

A second IgDART related to the smallpox product was also made. A monospecific 7hD11 DART unit was appended (followed by a (SEQ ID NO:42) GGGSGGGG linker) to the N-terminus of heavy chain and light chain constant regions (FIG. 14, Panel B). This protein is also expressed well (about 1 ug/ml in transient expression) and binds its antigen, L1 (FIG. 23).

Example 16

Orthopoxvirus-Neutralizing IgDART Molecule with MV and EV Binding Specificities

General Considerations:

In order to develop an above described IgDART molecule that is more potent than neutralizing mAbs or mAb mixtures and is suitable for rapid administration by a single intramuscular injection, an orthopoxvirus-neutralizing IgDART molecule with MV (mature virion) and EV (enveloped virion) binding specificities is to be constructed. This molecule, referred to below as the IgDART product is particularly suitable for use as a post-exposure prophylactic and/or treatment following a smallpox outbreak. However, because it is expected to have neutralizing activity against all orthopoxviruses, the IgDART product is also intended for the treatment or prevention of human monkeypox, an emerging zoonotic disease, and for treatment of complications due to smallpox vaccination (i.e., to serve as a more potent, better defined, safer, more readily manufactured and more easily administered alternative to VIGIV (vaccinia immune globulin intravenous), an approved, blood-derived, polyclonal immunoglobulin product).

Studies in vaccinia virus/mouse models demonstrate that a mixture of anti-MV and anti-EV mAbs is at least 50-fold more potent than VIGIV. The IgDART product, because of its multivalency and multispecificity, is expected to exhibit substantially higher avidity and thus considerably higher potency than an anti-MV:anti-EV mAb combination. The increased potency of the IgDART molecule allows selection of a therapeutic dose low enough to be administered by a single IM injection. The IgDART product is preferably stored as a lyophilized preparation, and reconstituted with sterile water prior to use. The shelf life of the material is expected to be equal or greater than 5 years at ambient temperatures, and the material is expected to maintain its stability when shipped or stored without refrigeration. Preferably, the IgDART product is administered as a single injection (preferably, 3.5 mg/kg or less of a preparation preferably containing 25-100 mg/mL of IgDART product), preferably intramuscularly (e.g., into the gluteus maximus muscle in volume ≤5 mL (the standard limit) or, more preferably, into the deltoid muscle in a volume ≤2 mL (the standard limit)). Multiple doses may be warranted for individuals with overt smallpox disease.

The IgDART product is expected to have a long circulation half-life that is similar to that observed for humanized mAbs against other viral pathogens (e.g., the terminal half-life of Synagis® (palivizumab) (Medimmune, Inc.), an anti-RSV mAb, is approximately 21 days). Thus, a single administration of the IgDART product should be sufficient and provide a long-lasting effect (possibly for months) for most subjects, particularly if administered before or shortly after exposure, or at least before the appearance of pox lesions. Moreover, because a single dose should suffice, there would no concern about subjects adhering to a prescribed regimen during the remaining course of the outbreak. However, for individuals that have frank signs and symptoms of smallpox disease and have high virus loads, multiple administrations of the IgDART product probably would be warranted to ensure the amelioration of disease and maximally reduce the risk of death.

The IgDART product is particularly well suited for administration to individuals for whom smallpox vaccination is contraindicated because of, for example, eczema or atopic dermatitis and other acute, chronic, or exfoliative skin conditions; diseases or conditions which cause immunodeficiency or immunosuppression; treatments which cause immunodeficiency or immunosuppression; pregnancy; previous allergic reaction to smallpox vaccine or any of the vaccine's components; moderate or severe acute illness; age criteria (infants and children); breastfeeding; or heart disease. The target population is thus the general public as well as special populations (especially those for which smallpox vaccination (i.e., the young, elderly, immunocompromised, individuals with heart disease) is contraindicated). Even during a stressful response to an outbreak, it should not be difficult to recognize many of the above-mentioned individuals and administer to them the IgDART product rather than a potentially risky vaccine. A further benefit is that individuals who are aware of the contraindications and risks of smallpox vaccination may feel less anxious after receiving a safer IgDART product, and thus may volunteer or present for treatment more readily.

Advantages of such an orthopoxvirus-neutralizing IgDART product over other smallpox countermeasures are manifold:

1. The IgDART product provides protection immediately, even in individuals who are very young, very old or otherwise have suboptimal or debilitated immune systems.
2. Unlike a vaccine, which must be administered within a few days of exposure, the IgDART, because of its immediate action, provides benefit when administered anytime during the approximately 2-week prodromal/incubation period. It also provides benefit even after overt signs of smallpox disease are evident. Additionally, it prevents or reduces mortality and mitigates disease in orthopoxvirus infected animals when administered before or after exposure.
3. The IgDART product is very safe. Since there are no known endogenous targets in uninfected individuals, it would not interact with uninfected tissue and cause side effects.
4. The risk in administering the IgDART product to uninfected individuals who are worried about being infected is minimal. Indeed, a single administration will provide protective levels of the orthopoxvirus-neutralizing IgDART for many months.
5. It may be administered rapidly by a single intramuscular injection.
6. A single injection will provide long-lasting protection for the duration of an outbreak. The IgDART product has a circulating half-life of greater than 3 weeks
7. The lyophilized product is stable at ambient temperatures and does not require refrigeration for shipping or storage.
8. Because the IgDART molecules bind to and neutralize orthopoxvirus particles, infectious virus transmission is greatly reduced, including for those virus particles released from lesions during the normally infectious phase.
9. Based on their mechanism of action, IgDART molecules are highly effective at neutralizing enhanced orthopoxvirus agents, such as IL-4 recombinant orthopoxviruses.
10. Based on the differences in their mechanisms of action, the IgDART product is compatible with, and should synergize with, promising small molecule antivirals, such as ST-246 (Smee, D. F. (2008) "*Progress In The Discovery Of Compounds Inhibiting Orthopoxviruses In Animal Models*," Antivir. Chem. Chemother. 19(3): 115-124; De Clercq, E. et al. (2008) "*Emerging Antiviral Drugs*," Expert. Opin. Emerg. Drugs 13(3):393-416; Bolken, T. C. et al. (Epub 2007 Aug. 15) "Discovery and development of antiviral drugs for biodefense: experience of a small biotechnology company," Antiviral Res. 77(1):1-5; and CMX001 (Parker, S. (Epub 2007 Sep. 4) "*Efficacy Of Therapeutic Intervention With An Oral Ether-Lipid Analogue Of Cidofovir (CMX001) In A Lethal Mousepox Model*," Antiviral Res. 77(1):39-49; Quenelle, D. C. et al. (Epub 2007 Aug. 27) "*Synergistic Efficacy Of The Combination Of ST-246 With CMX001 Against Orthopoxviruses*," Antimicrob Agents Chemother. 51(11):4118-4124). Indeed, a combination of IgDART and antiviral drugs may be the most effective way to treat individuals who present with overt signs of smallpox disease.
11. Although single point mutations in the virus can confer resistance to the small molecule antiviral drugs, such as ST-246 or CMX001, such mutations are unlikely to confer resistance to the IgDART product because of its multivalent and multispecific structure.
12. The IgDART product is not restricted to the prevention or treatment of smallpox, but may also be used to prevent or treat all pathogenic orthopoxvirus (e.g., variola, vaccinia, monkeypox) infections.
13. The IgDART is a single molecule, which simplifies its manufacture relative to that of mixtures of monoclonal antibodies.

The cost of an IgDART product may be higher than that of smallpox vaccines or low molecular weight antiviral drugs. However, the actual cost will be greatly influenced by economies of scale and, in most cases, only a single dose will be required. The IgDART product may additionally differ form smallpox vaccines or low molecular weight antiviral drugs in not being orally bioavailable and in its preferred form of administration (i.e., parenterally). The IgDART product is not a medical countermeasure with broad specificity; it is restricted to the prevention or treatment of orthopoxvirus infections. Although the IgDART might impair the efficacy of recently administered, live vaccinia virus vaccines, it should not interfere with the efficacy of inactivated, recombinant protein or DNA-based vaccines.

In sum, the IgDART product is preferably at least 3-fold more potent than the most potent anti-MV:anti-EV mAb combination (Ch7D11:Ch12F, which has a projected therapeutic dose of 10 mg/kg), and as such be capable of neutralizing MV and EV forms of pathogenic orthopoxviruses (preferably at least 50-fold more potent than VIGIV (vaccinia immunoglobulin intravenous), and of neutralizing variola virus in vitro. The product exhibits post exposure therapeutic activity in orthopoxvirus challenge models such as vaccinia virus in mice, ectromelia virus in mice, and monkeypox virus in cynomolgus monkeys at dose levels that are feasible for administration to human subjects by IM injection. For example, for an IgDART product that is formulated at 50 mg/mL for injection into the gluteus maximus muscle in a volume of 5 mL (the standard limit), the predicted therapeutic dose must be 3.5 mg/kg or less (calculated as 50 mg/mL×5 mL÷70 kg). The product has a favorable PK (terminal half-life ≥7 days) and bioavailability (≥60%) following IM administration in cynomolgus monkeys. Preferably, the product is produced through recombinant expression in CHO cells at a level of ≥1 g/L. Lyophilized formulations maintain their stability at ambient and elevated temperatures and are readily reconstituted with sterile water. The product does not give rise to unexpected tissue cross-reactivity, or to major safety signals in GLP toxicology studies in cynomolgus monkeys and exhibits an NOAEL value that justifies the proposed human starting dose.

Preferred orthopoxvirus-Neutralizing IgDART Molecules

The binding specificities for the IgDART molecules are derived from well-characterized monoclonal antibodies. As discussed above, ch7D11 is a moderate affinity, chimeric (mouse/human) neutralizing mAb that targets the L1 protein expressed on the surface of MV (mature virion) particles. A humanized version (h7D11) was constructed and is being further improved by affinity maturation. Ch8A and Ch12F are high affinity, chimeric (chimp/human) neutralizing mAbs that target the B5 and A33 proteins, respectively, expressed on the surface of EV (enveloped virion) particles.

Mice are protected from lethal virus challenge when Ch8A or Ch12 is administered prophylactically, and mice are partially protected when the mAbs are administered therapeutically at 2 days post infection (Chen, Z. et al. (2006) "*Chimpanzee/Human Mabs To Vaccinia Virus B5 Protein Neutralize Vaccinia And Smallpox Viruses And Protect Mice Against Vaccinia Virus*," Proc. Natl. Acad. Sci. (U.S.A.) 103(6):1882-1887; Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995). Ch8A:Ch12F mixtures do not exhibit greater in vivo potency than either individual mAb. When administered prophylactically at −1 DPI or therapeutically at 2 DPI to mice inoculated intranasally with a mild vaccinia virus challenge (105 pfu), Ch8A or Ch12F prevented mortality and also reduced morbidity (Chen et al. 2006; 2007). In these studies, the activity of either of the mAbs at 5 mg/kg was slightly more effective than VIG at 250 mg/kg. By contrast, when administered prophylactically to mice inoculated with a 10-fold higher virus challenge, Ch12F prevented mortality, but did not reduce morbidity (Chen, Z. et al. (Jun. 20, 2007) "*Characterization Of Chimpanzee/Human Monoclonal Antibodies To Vaccinia Virus A33 Glycoprotein And Its Variola Virus Homolog In Vitro And In A Vaccinia Virus Mouse Protection Model*," J. Virol. 81(17):8989-8995).

Ch711:Ch12F, a 1:1 combination of anti-MV and anti-EV mAbs, is the most potent antibody mixture, based on prophylactic and post-exposure therapeutic efficacy studies in vaccinia virus-infected mice. The two mAbs are currently formulated as a liquid in PBS-T (phosphate buffered saline with TWEEN-80®) and are separately stored at 2-8 C.°.

An exemplary orthopoxvirus-neutralizing IgDART molecule contains one or more binding domains from the affinity matured h7D11 for anti-MV activity, and one or more binding domains from Ch12F and/or Ch8A for anti-EV activity. The binding domains will be configured as monospecific or bispecific DART units that are constrained by a disulfide bond for stability and attached to the N- and/or C-termini of an IgG1 constant region backbone.

In order to increase the stability and half-life, as well as to immunologically functionalize the DART proteins, IgG fusions have been made in which the V-regions on the N-terminus have been replaced with homodimeric DART units and in which heterodimeric DART units have been appended to the C-termini of Fc fragment of IgG. These approaches can be merged to increase valency and the number of specificities that can be combined on a single molecule (FIG. 24, Panels A-J).

Initial data with monoclonal antibodies indicate that a 1:1 ratio of anti-EV to anti-MV antibody is optimal in a post-exposure treatment model. Therefore, constructs with 1:1 ratios of different specificities such as those depicted in FIG. 24, Panels B, C, E and H are preferred. Then, constructs that would afford the product greater avidity, such as the octavalent constructs depicted in FIG. 24, Panels C and H are preferred. The resultant 10 preferred constructs (six iterations of trispecific DARTs and four iterations of bispecific DARTs) are depicted in Table 5 below. To determine the optimal mAb ratio for therapeutic activity, mAb mixtures at various ratios were administered at 2 DPI at 5 mg/kg, a dose that corresponds to the ED50 (FIG. 5C). For either Ch7D11:Ch12F or Ch7D11:Ch8A, the optimal ratio was 50:50 (FIG. 21). The subset of such IgDARTs shown in Table 6 was produced and evaluated.

TABLE 5

| Trispecific DARTs | | | | | | |
|---|---|---|---|---|---|---|
| | 1 | 2 | 3 | 4 | 5 | 6 |
| N-Terminus | 7D11 | 8A | 12F | 8A/12F | 7D11/12F | 7D11/8A |
| C-Terminus | 8A/12F | 7D11/12F | 7D11/8A | 7D11 | 8A | 12F |
| Concentration | | | | | | |

| Bispecific DARTs | | | | |
|---|---|---|---|---|
| | 1 | 2 | 3 | 4 |
| N-Terminus | 7D11 | 7D11 | 12F | 8A |
| C-Terminus | 12F | 8A | 7D11 | 7D11 |
| Concentration | | | | |

TABLE 6

| No. | Characteristic | Specificity | Concentration Employed |
|---|---|---|---|
| 1 | 7D11(D102Y)-12F-LGGC IgG DART | Tetravalent Bispecific | 0.23 |
| 2 | 7D11(D102Y)-G3S-12F-LGGC IgG DART | Tetravalent Bispecific | 0.39 |
| 3 | 7D11(D102Y)-12F-LGGC IgG DART | Hexavalent Bispecific | 0.23 |
| 4 | 7D11(D102Y)-G3S-12F-LGGC IgG DART | Hexavalent Bispecific | 0.28 |
| 5 | 7D11(D102Y)-12F-FNRGEC/VEPKSC IgG DART | Hexavalent Bispecific | 0.13 |
| 6 | 7D11(D102Y)-G3S-12F-FNRGEC/VEPKSC IgG DART | Hexavalent Bispecific | 0.20 |

FIG. 25 (Panels A-C) shows the structures of the bispecific IgDARTS. FIG. 26 shows results of ELISAs employing these IgDARTS, and demonstrates their ability to bind to orthopoxvirus. Such binding was confirmed using Western Blots. FIG. 27 (Panels A-B) shows the ability of such bispecific IgDARTS to capture A33 or IgG. ELISAs demonstrated that such IgDARTS did not bind to B5, a finding consistent with the fact that these DARTS do not have a B5 binding epitope.

Two trispecific IgDARTS (denoted as 217 and 218) were also produced and tested. FIG. 28 (Panels A-B) shows the structures of these IgDARTS. 218 differs from 217 in possessing a short linker (SEQ ID NO:42) GGGSGGGG between the C-terminus of the IgG and the DART. FIG. 29 (Panels A-E) and FIG. 30 (Panels A-C) show the results of ELISAs employing the trispecific IgDARTS, and demonstrates their ability to bind to orthopoxvirus.

The ability of the trispecific IgDARTs to bind simultaneously to multiple epitopes was determined by injection of antibody or buffer over a surface containing immobilized B5 followed by consequent injections of A33 and L1R. As shown in FIG. 31, trispecific IgDART that had been bound to antigen at one of epitope binding sites exhibited a continued capability to bind to additional epitopes.

12F×h7D11 IgDARTs in which 12F and 8A DARTS were fused to the variable regions of the Ig H and L chains, and in which a monospecific bivalent h7D11 DART (preferably, containing D102Y) was fused to the C-terminus of the Ig H chains (FIG. 32) were produced and evaluated. Binding analyses (ELISAs) conducted using these IgDARTS show that moving the epitope binding sites of the DARTS did not affect binding ability (i.e., full activity was retained) (FIG. 33).

12F×h7D11 IgDARTs in which with all DART sequences are on the N-terminus of the molecule (i.e., in which the C-terminus was unaltered) (FIG. 32) were also produced and evaluated. Binding analyses (ELISAs) conducted using these IgDARTS show that moving the epitope binding sites of the DARTS did not affect binding ability or biospecificity (i.e., full activity and biospecificity was retained) (FIG. 34).

Additional variations of such IgDARTS may be advantageously employed. For example, the cysteine residue may be removed from the C-terminus of the molecule, the linker separating the Ig Fc region and the DART may be varied, an aglycosylated Fc region (e.g., containing N297Q) may be employed, the VH, $CH_1$ and hinge region may be removed from the N-terminus (Fc-DART).

In summary, combinations of anti-MV and anti-EV monoclonal antibodies exhibit synergistic prophylactic and therapeutic activity and are potent orthopoxvirus immunotherapeutic agents. The most potent combination is a 50:50 mixture of Ch7D11 (an anti-L1 mAb) and Ch12F (an anti-A33 mAb). The protective dose is dependent on the number of days post-infection and the magnitude of the virus challenge dose. For a Ch7D11:Ch12F combination administered therapeutically as late as 3 days following a strong virus challenge, the minimum dose for full or nearly full survival is 10 mg/kg.

Example 17

Prophylactic and Therapeutic Activity of a Combination of Anti-MV and Anti-EV mAbs in Ectromelia Virus-Infected Mice Ectromelia virus is a laboratory pathogen of mice. The pathogenesis of ectromelia virus disease closely resembles human smallpox, with distinct stages of localized replication, systemic virus spread and lesion formation. However, the time course of infection and disease progression is much shorter (Jordan, R. et al. (2006) "*Smallpox Antiviral Drug Development: Satisfying The Animal Efficacy Rule*," Expert Rev. Anti. Infect. Ther. 4(2):277-289).

The natural route of ectromelia infection is through abrasions in the skin and it replicates in local lymphoid cells. The virus multiplies in the lymphatic endothelial cells, macrophages and lymphocytes within the node over a period of 2-4 days. Following this latency period, the virus spreads through the lymph and enters the bloodstream to cause a primary viremia. The virus is rapidly removed by macrophages lining the sinusoids of the liver, spleen and bone marrow. Infection of parenchymal cells of liver and lymphoid cells of the spleen produces high virus titers that are released into the bloodstream to cause a secondary viremia. In highly susceptible animals, replication in the liver and spleen produces focal necrotic lesions, acute hepatitis and multiorgan failure. In mice that are less susceptible, a rash develops following the secondary viremia. The rash is caused by virus replication in the perivascular cells, dermal endothelia cells and epidermis.

In susceptible mice less than 1 PFU of ectromelia virus is sufficient to cause lethal infection. Mice can be inoculated with ectromelia virus either by footpad scarification, which is similar to the natural route of infection, or intranasal delivery. The virus multiplies in the lymphatic endothelial cells, macrophages and lymphocytes within the regional node over a period of 2-4 days. By day 4 post inoculation, animals appear ill with hunched posture, ruffled coat and increased respiration. Viral replication in the liver and spleen and other internal organs cause death in the infected animals between days 6 and 10 post inoculation. Similar to the vaccinia virus/mouse model, disease progression can be monitored by measuring the change in weight during the course of infection. Thus, in an infection model, antiviral efficacy is measured by decreased mortality, inhibition of virus-induced weight loss and reduction of virus titers in liver, spleen and other tissues.

A pilot study was performed under the direction of Dr. Mark Buller at St Louis University. The study utilized A/NCR mice, which are highly susceptible to ectromelia virus infection. In the experiment, the mice were inoculated intranasally with 0.6 PFU of ectromelia virus, which, based on Dr. Buller's prior experience, was expected to result in 100% lethality.

Ch7D11, the anti-MV mAb, is likely to neutralize ectromelia virus because the epitope recognized by this antibody is 100% conserved. Anti-EV mAbs are also likely to neutralize ectromelia virus given the high level of conservation in the epitope region, but direct studies are required to determine if the subtle differences will prevent cross-reactivity. To maximize the possibility of observing strong neutralizing activity in ectromelia-infected mice, a 3:1:1:1 mixture of h7D11: Ch12F:Ch6C:Ch8A (which is a 1:1 combination of anti-MV and anti-EV mAbs) was administered at dose levels of 1, 10 or 100 mg/kg to mice by IP injection at 24 hours before or 24 hours after ectromelia virus infection. Mice were also administered cidofovir, a known antiviral agent, at a dose level of 100 mg/kg as a positive control.

The data show that partial protection (40-60% survival) was observed when mice received the mAb mixture at 1 mg/kg at −24 h (40% survival) or +24 h (60% survival), and that full protection (100% survival and minimal to no weight loss) was observed when mice received the mAb mixture at 10 or 100 mg/kg at −24 h or +24 h (Table 7). Similar full protection was observed with cidofovir at 100 mg/kg. These data show that the mAb cocktail was effective in neutralizing ectromelia virus in mice and that the mAb dose response was similar to that observed with vaccinia virus in mice. Thus, the ectromelia virus/mouse model may be developed as one of the 'animal rule' efficacy models.

TABLE 6

| # of Cage | mice | Virus | Treatment Article | Dose (mg/kg) | Time (h) | Day of Death | Mortality |
|---|---|---|---|---|---|---|---|
| 1 | 5 | − | vehicle | NA | −24 |  | 0% |
| 2 | 5 | + | vehicle | NA | −24 | 8, 9, 9, 9, 10 | 100% |
| 3 | 5 | + | mAb cocktail | 1 | −24 | 10, 11, 14 | 60% |
| 4 | 5 | + | mAb cocktail | 1 | +24 | 11, 15 | 40% |
| 5 | 5 | + | mAb cocktail | 10 | −24 |  | 0% |
| 6 | 5 | + | mAb cocktail | 10 | +24 |  | 0% |
| 7 | 5 | + | mAb cocktail | 100 | −24 |  | 0% |
| 8 | 5 | + | mAb cocktail | 100 | +24 |  | 0% |
| 9 | 5 | + | CDV | 100 | −24 |  | 0% |
| 10 | 5 | + | CDV | 100 | +24 |  | 0% |

50 A/NCR female mice; 0.6 PFU ectromelia virus (intranasal) per mouse; CDV = cidofovir; mAb cocktail = 1:1 mixture of anti-MV + anti-EV mAbs (Ch7D11:Ch12F:Ch6C:Ch8A, 3:1:1:1)

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A composition that comprises a dual affinity retargeting reagent, wherein said reagent immunospecifically binds to an epitope found on an MV form of the smallpox virus;
   wherein said dual affinity retargeting reagent comprises a first and a second polypeptide chain, being covalently linked to one another, wherein:
   (I) said first polypeptide chain comprises, from N-terminus to C-terminus:
      (A) a domain (I) comprising a binding region of a light chain variable domain of a first immunoglobulin (VL1);
      (B) a domain (II) comprising a binding region of a heavy chain variable domain of a second immunoglobulin (VH2); and
      (C) a domain (III) comprising CH2 and CH3 domains of an Fc region, and a hinge region;
      wherein domains (I) and (II) are covalently linked to one another such that they do not associate to form an epitope binding site; and
   (II) said second polypeptide chain comprises, from N-terminus to C-terminus:
      (A) a domain (IV) comprising a binding region of a light chain variable domain of the second immunoglobulin (VL2); and
      (B) a domain (V) comprising a binding region of a heavy chain variable domain of the first immunoglobulin (VH1);
      wherein domains (IV) and (V) are covalently linked to one another such that they do not associate to form an epitope binding site;
      wherein domains (I) and (V) associate to form an epitope binding site that immunospecifically binds said epitope found on said MV form of the smallpox virus, and domains (II) and (IV) associate to form an epitope binding site that immunospecifically binds a second epitope.

2. The composition of claim 1, wherein said second polypeptide chain comprises a domain (VI) comprising an Fc domain or at least the C-terminal 2 to 8 amino acid residues of a human light chain constant domain.

3. The composition of claim 1, wherein said epitope found on said MV form of the smallpox virus is an epitope of an L1 protein of said smallpox virus.

4. The composition of claim 3, wherein said epitope of said L1 protein is located within non-contiguous domains of L1, said domains having the amino acid sequences of SEQ ID NOS:13-15.

5. The composition of claim 1, wherein said first immunoglobulin is a humanized or chimeric antibody.

6. The composition of claim 5, wherein said humanized or chimeric antibody is a humanized 7D11 antibody or the chimeric antibody Ch7D11.

7. The composition of claim 6, wherein said humanized or chimeric antibody or fragment thereof is the humanized 7D11 antibody h7D11.

8. The composition of claim 6, wherein said humanized or chimeric antibody is a variant of the humanized antibody h7D11.

9. The composition of claim 8, wherein said variant of the humanized antibody h7D11 comprises selected amino acid modification(s) relative to the amino acid sequence of said humanized antibody h7D11, wherein said selected amino acid modification(s) consist of one or more of the following mutations: M48I, I69L, and V67A, wherein said selected amino acid modification(s) cause said variant antibody to exhibit increased binding to antigen relative to said humanized antibody h7D11.

10. A composition that comprises a dual affinity retargeting reagent, wherein said reagent immunospecifically binds to an epitope found on an EV form of the smallpox virus;
   wherein said dual affinity retargeting reagent comprises a first and a second polypeptide chain, being covalently linked to one another, wherein:
   (I) said first polypeptide chain comprises, from N-terminus to C-terminus:
      (A) a domain (I) comprising a binding region of a light chain variable domain of a first immunoglobulin (VL1) specific for a first epitope;
      (B) a domain (II) comprising a binding region of a heavy chain variable domain of a second immunoglobulin (VH2) specific for a second epitope; and
      (C) a domain (III) comprising CH2 and CH3 domains of an Fc region, and a hinge region;
      wherein domains (I) and (II) are covalently linked to one another such that they do not associate to form an epitope binding site; and
   (II) said second polypeptide chain comprises, from N-terminus to C-terminus:

(A) a domain (IV) comprising a binding region of a light chain variable domain of the second immunoglobulin (VL2); and (B) a domain (V) comprising a binding region of a heavy chain variable domain of the first immunoglobulin (VH1);

wherein domains (IV) and (V) are covalently linked to one another such that they do not associate to form an epitope binding site;

wherein domains (I) and (V) associate to form an epitope binding site that immunospecifically binds said epitope found on said EV form of the smallpox virus, and domains (II) and (IV) associate to form an epitope binding site that immunospecifically binds a second epitope.

11. The composition of claim 10, wherein said second polypeptide chain comprises a domain (VI) comprising an Fc domain or at least the C-terminal 2 to 8 amino acid residues of a human light chain constant domain.

12. The composition of claim 10, wherein said epitope found on said EV form of the smallpox virus is an epitope of an A33 protein of said smallpox virus.

13. The composition of claim 12, wherein said epitope of said A33 protein is located within a domain of A33, said domain having the amino acid sequence of SEQ ID NO:40.

14. The composition of claim 10, wherein said first immunoglobulin is a humanized or chimeric antibody.

15. The composition of claim 10, wherein said epitope found on said EV form of the smallpox virus is an epitope of a B5 protein of said smallpox virus.

16. The composition of claim 15, wherein said epitope of said B5 protein is located within a domain of B5, said domain having the amino acid sequence of SEQ ID NO:41.

17. The composition of claim 14, wherein said humanized or chimeric antibody is selected from the group consisting of the chimeric antibody Ch8AH8AL, the chimeric antibody Ch12F, and the chimeric antibody Ch6C.

18. The composition of claim 1, wherein domains (II) and (IV) associate to form an epitope binding site that immunospecifically binds to an epitope found on an EV form of the smallpox virus.

19. The composition of claim 10, wherein domains (II) and (IV) associate to form an epitope binding site that immunospecifically binds to an epitope found on an MV form of the smallpox virus.

* * * * *

```
                         SEQUENCE LISTING

<160> NUMBER OF SEQ ID NOS: 44

<210> SEQ ID NO 1
<211> LENGTH: 336
<212> TYPE: DNA
<213> ORGANISM: Mus sp.

<400> SEQUENCE: 1
gacatggtga tgtcacagtc tccatcctcc ctggctgtgt cagcaggaga gaaggtcagt     60
atgagctgca aatccagtca gactctgctc aacagtagaa cccgaaagaa ctacttggct    120
tggtaccagc agaaaccagg gcagtctcct aaactactga tctactgggc atccactagg    180
gaatctgggg tccctgatcg cttcacaggc agtggatctg ggacagattt cactctcacc    240
atcagcagtg tgcaggctga agacctggca gtttattact gcaagcaatc ttataatctg    300
tggacgttcg gtggaggcac caagctggaa atcaaa                              336

<210> SEQ ID NO 2
<211> LENGTH: 112
<212> TYPE: PRT
<213> ORGANISM: Mus sp.

<400> SEQUENCE: 2

Asp Met Val Met Ser Gln Ser Pro Ser Ser Leu Ala Val Ser Ala Gly
1               5                   10                  15

Glu Lys Val Ser Met Ser Cys Lys Ser Ser Gln Thr Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

```
Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110
```

<210> SEQ ID NO 3
<211> LENGTH: 357
<212> TYPE: DNA
<213> ORGANISM: Mus sp.

<400> SEQUENCE: 3

```
caggtccagc ttcagcagtc tggggctgaa ctggcaaaac ctggggcctc agtgaagatg      60
tcctgcaagg cttctggcta cacctttact aggtactgga tgcactgggt aaaacagagg     120
cctggacagg gtctggaatg gattggatac attaatccta gcactggtta tactgagtac     180
aatcagaaat tcaaggacaa ggccacattg actgcggaca atcctccag  cacagtctac     240 atgcaactga gcagcctgac atctgaggac tctgcagtct attactgtgc aagaactaca     300
gtggatggtt acgactttgc ttactggggc caagggactc tggtcactgt ctcggca        357
```

<210> SEQ ID NO 4
<211> LENGTH: 119
<212> TYPE: PRT
<213> ORGANISM: Mus sp.

<400> SEQUENCE: 4

```
Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Arg Thr Thr Val Asp Gly Tyr Asp Phe Ala Tyr Trp Gly Gln Gly
            100                 105                 110

Thr Leu Val Thr Val Ser Ala
        115
```

<210> SEQ ID NO 5
<211> LENGTH: 336
<212> TYPE: DNA
<213> ORGANISM: artificial
<220> FEATURE:
<223> OTHER INFORMATION: humanized murine 7D11 antibody light chain
      variable region

<400> SEQUENCE: 5

```
gacatcgtga tgacccaatc tccagactct ttggctgtgt ctctagggga gagggccacc      60
atcaactgca atccagtca  gactctgctc aacagtagaa cccgaaagaa ctacttggct     120
tggtaccaac agaaaccagg acagccaccc aaactcctca tctactgggc atccactagg     180
gaatctgggg tcccagacag gtttagtggc agtgggtctg gacagactt  caccctcacc     240
```

```
atcagcagcc tgcaggctga ggatgtggca gtttattact gcaagcaatc ttataatctg    300
tggacgttcg acaagggac caagcttgag atcaaa                               336
```

<210> SEQ ID NO 6
<211> LENGTH: 112
<212> TYPE: PRT
<213> ORGANISM: artificial
<220> FEATURE:
<223> OTHER INFORMATION: humanized 7D11 murine antibody light chain
      variable region

<400> SEQUENCE: 6

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Trp Thr Phe Gly Gln Gly Thr Lys Leu Glu Ile Lys
            100                 105                 110
```

<210> SEQ ID NO 7
<211> LENGTH: 658
<212> TYPE: DNA
<213> ORGANISM: artificial
<220> FEATURE:
<223> OTHER INFORMATION: humanized murine antibody 7D11 light chain

<400> SEQUENCE: 7

```
gacatcgtga tgacccaatc tccagactct ttggctgtgt ctctagggga gagggccacc     60
atcaactgca atccagtca gactctgctc aacagtagaa cccgaaagaa ctacttggct    120
tggtaccaac agaaaccagg acagccaccc aaactcctca tctactggc atccactagg    180 gaatctgggg tcccagacag gtttagtggc agtgggtctg gacagactt caccctcacc    240 atcagcagcc tgcaggctga ggatgtggca gtttattact gcaagcaatc ttataatctg    300
tggacgttcg acaagggac caagcttgag atcaaagtcc tcggtcagcc caaggccaac    360
cccacagtca ccctgttccc gccctcctct gaggagcttc aagccaacaa ggccacactg    420
gtgtgtctca taagtgactt ctacccggga gccgtgacag tggcctggaa ggcagatggc    480
agccccgtca aggcgggagt ggagaccacc acaccctcca acaaagcaa caacaagtac    540 gcggccagca gctacctgag cctgacgccc gagcagtgga gtcccacag aagctacagc    600 tgccaggtca cgcatgaagg gagcaccgtg gagaagacag tggcccctac agaatgtt     658
```

<210> SEQ ID NO 8
<211> LENGTH: 204
<212> TYPE: PRT
<213> ORGANISM: artificial
<220> FEATURE:
<223> OTHER INFORMATION: humanized murine antibody 7D11 light chain

```
<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Leu Asn Ser
            20                  25                  30

Arg Thr Arg Lys Asn Tyr Leu Ala Trp Ala Ser Thr Arg Glu Ser Gly
        35                  40                  45

Val Pro Asp Arg Phe Ser Gly Ser Gly Ser Thr Asp Phe Thr Leu
    50                  55                  60

Thr Ile Ser Ser Leu Gln Ala Glu Asp Val Ala Val Tyr Tyr Cys Lys
65                  70                  75                  80

Gln Ser Tyr Asn Leu Trp Thr Phe Gly Gln Gly Thr Lys Leu Glu Ile
                85                  90                  95

Lys Arg Thr Val Ala Ala Pro Ser Val Phe Ile Phe Pro Pro Ser Asp
            100                 105                 110

Glu Gln Leu Lys Ser Gly Thr Ala Ser Val Val Cys Leu Leu Asn Asn
        115                 120                 125

Phe Tyr Pro Arg Glu Ala Lys Val Gln Trp Lys Val Asp Asn Ala Leu
130                 135                 140

Gln Ser Gly Asn Ser Gln Glu Ser Val Thr Glu Gln Asp Ser Lys Asp
145                 150                 155                 160

Ser Thr Tyr Ser Leu Ser Ser Thr Leu Thr Leu Ser Lys Ala Asp Tyr
                165                 170                 175

Glu Lys His Lys Val Tyr Ala Cys Glu Val Thr His Gln Gly Leu Ser
            180                 185                 190

Ser Pro Val Thr Lys Ser Phe Asn Arg Gly Glu Cys
        195                 200

<210> SEQ ID NO 9
<211> LENGTH: 357
<212> TYPE: DNA
<213> ORGANISM: artificial
<220> FEATURE:
<223> OTHER INFORMATION: humanized murine antibody 7D11heavy chain
      variable region

<400> SEQUENCE: 9
caggttcagc tggtgcagtc tggagctgag gtgaagaagc ctggggcctc agtgaaggtc      60
tcctgcaagg cttctggtta cacctttacc cggtactgga tgcactgggt gcgacaggcc    120
cctggacaag gcttgagtg gatgggatac attaatccta gcactggtta tactgagtac     180
aatcagaaat tcaaggacag agtcacgatt accgcggaca atcaacgag cacagcctac     240 atggagctga ggagcctgag atctgacgac acggccgtgt attactgtgc gagaactaca     300
gtggatggtt acgactttgc ttactggggc caaggaaccc tggtcaccgt ctcctca         357

<210> SEQ ID NO 10
<211> LENGTH: 119
<212> TYPE: PRT
<213> ORGANISM: artificial
<220> FEATURE:
<223> OTHER INFORMATION: humanized murine antibody 7D11 heavy chain
      variable region

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
```

```
                  20                  25                  30
Trp Met His Trp Val Lys Gln Ala Pro Gly Gln Gly Leu Glu Trp Met
            35                  40                  45

Gly Tyr Ile Asn Pro Ser Thr Gly Tyr Thr Glu Tyr Asn Gln Lys Phe
        50                  55                  60

Lys Asp Arg Val Thr Ile Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Thr Val Asp Gly Tyr Asp Phe Ala Tyr Trp Gly Gln Gly
            100                 105                 110

Thr Leu Val Thr Val Ser Ser
        115

<210> SEQ ID NO 11
<211> LENGTH: 1350
<212> TYPE: DNA
<213> ORGANISM: artificial
<220> FEATURE:
<223> OTHER INFORMATION: humanized murine antibody 7D11 heavy chain

<400> SEQUENCE: 11
caggttcagc tggtgcagtc tggagctgag gtgaagaagc ctggggcctc agtgaaggtc      60
tcctgcaagg cttctggtta cacctttacc cggtactgga tgcactgggt gcgacaggcc     120
cctggacaag gcttgagtg atgggatac attaatccta gcactggtta tactgagtac      180
aatcagaaat tcaaggacag agtcacgatt accgcggaca atcaacgag cacagcctac     240
atggagctga ggagcctgag atctgacgac acggccgtgt attactgtgc gagaactaca     300
gtggatggtt acgactttgc ttactggggc caaggaaccc tggtcaccgt ctcctcagcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaactcct ggggggaccg    720
tcagtcttcc tcttccccccc aaaacccaag gacaccctca tgatctcccg gaccccctgag  780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                      1350

<210> SEQ ID NO 12
<211> LENGTH: 449
```

```
<212> TYPE: PRT
<213> ORGANISM: artificial
<220> FEATURE:
<223> OTHER INFORMATION: humanized murine 7D11 antibody heavy chain

<400> SEQUENCE: 12
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 |

Ser Val Lys Val Ser Cys Lys Ala Ser Gly Tyr Thr Phe Thr Arg Tyr
            20                  25                  30

Trp Met His Trp Val Lys Gln Ala Pro Gly Gln Gly Leu Glu Trp Met
            35                  40                  45

Gly Tyr Ile Asn Pro Ser Thr Gly Tyr Thr Glu Tyr Asn Gln Lys Phe
 50                  55                  60

Lys Asp Arg Val Thr Ile Thr Ala Asp Lys Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Thr Thr Val Asp Gly Tyr Asp Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Leu Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Leu Arg Val
290                 295                 300

Val Ser Ile Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Leu Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 13
<212> TYPE: PRT
<213> ORGANISM: artificial
<220> FEATURE:
<223> OTHER INFORMATION: L1 viral protein binding site for antibodies
      7D11 and h7D11

<400> SEQUENCE: 13

Glu Ala Asn Ala Ser Ala Gln Thr Lys Cys Asp Ile Glu
1               5                   10

<210> SEQ ID NO 14
<211> LENGTH: 9
<212> TYPE: PRT
<213> ORGANISM: artificial
<220> FEATURE:
<223> OTHER INFORMATION: L1 viral protein epitope for 7D11 and h7D11
      antibodies

<400> SEQUENCE: 14

Met Cys Ser Ala Asp Ala Asp Ala Gln
1               5

<210> SEQ ID NO 15
<211> LENGTH: 7
<212> TYPE: PRT
<213> ORGANISM: artificial
<220> FEATURE:
<223> OTHER INFORMATION: L1 viral protein epitope for 7D11 and h7D11
      antibodies

<400> SEQUENCE: 15

Asp Asn Lys Leu Lys Ile Gln
1               5

<210> SEQ ID NO 16
<211> LENGTH: 324
<212> TYPE: DNA
<213> ORGANISM: artificial
<220> FEATURE:
<223> OTHER INFORMATION: Light Chain Variable Region of Ch6C antibody

<400> SEQUENCE: 16
gagctcgtgt tgacgcagcc gccctcagtg tctgcggccc caggacagaa gatcactatt    60
tcctgctctg gaagcggctc caacattggg aggcattatg tatcctggta ccaacaattc   120
ccaggaacag cccccaaaat cctcatttat gacaatgata agcgaccctc agggatttcc   180
gaccgattct ctggctccaa gtctggcgcg tcagccaccc tggacatcac cggactccag   240
actggggacg aggccgatta ttactgcgca acatgggata ccaacttgag tggtggggtg   300
ttcggcggag ggactaaagt gacc                                          324

<210> SEQ ID NO 17
<211> LENGTH: 108
<212> TYPE: PRT
<213> ORGANISM: artificial
<220> FEATURE:
<223> OTHER INFORMATION: Light Chain Variable Region of Ch6C antibody

<400> SEQUENCE: 17

Glu Leu Val Leu Thr Gln Pro Pro Ser Val Ser Ala Ala Pro Gly Gln
1               5                   10                  15

Lys Ile Thr Ile Ser Cys Ser Gly Ser Gly Ser Asn Ile Gly Arg His
            20                  25                  30

Tyr Val Ser Trp Tyr Gln Gln Phe Pro Gly Thr Ala Pro Lys Ile Leu
        35                  40                  45

Ile Tyr Asp Asn Asp Lys Arg Pro Ser Gly Ile Ser Asp Arg Phe Ser
    50                  55                  60

Gly Ser Lys Ser Gly Ala Ser Ala Thr Leu Asp Ile Thr Gly Leu Gln
65                  70                  75                  80

Thr Gly Asp Glu Ala Asp Tyr Tyr Cys Ala Thr Trp Asp Thr Asn Leu
                85                  90                  95

Ser Gly Gly Val Phe Gly Gly Gly Thr Lys Val Thr
            100                 105

<210> SEQ ID NO 18
<211> LENGTH: 646
<212> TYPE: DNA
<213> ORGANISM: artificial
<220> FEATURE:
<223> OTHER INFORMATION: Light Chain of Ch6C antibody

<400> SEQUENCE: 18
gagctcgtgt tgacgcagcc gccctcagtg tctgcggccc caggacagaa gatcactatt      60
tcctgctctg gaagcggctc aacattggga aggcattatg tatcctggta ccaacaattc     120
ccaggaacag ccccaaaat cctcatttat gacaatgata gcgaccctc agggatttcc       180
gaccgattct ctggctccaa gtctggcgcg tcagccaccc tggacatcac cggactccag     240
actgggacg aggccgatta ttactgcgca catggggata ccaacttgag tggtggggtg      300
ttcggcggag ggactaaagt gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcggagtgg agaccaccac accctccaaa caaagcaaca caagtacgc ggccagcagc       540
tacctgagcc tgacgcccga gcagtggaag tcccacaaaa gctacagctg ccaggtcacg     600
catgaaggga gcaccgtgga agacagtg gccctacag aatgtt                       646

<210> SEQ ID NO 19
<211> LENGTH: 215
<212> TYPE: PRT
<213> ORGANISM: artificial
<220> FEATURE:
<223> OTHER INFORMATION: Light Chain of Ch6C antibody

<400> SEQUENCE: 19

Glu Leu Val Leu Thr Gln Pro Pro Ser Val Ser Ala Ala Pro Gly Gln
1               5                   10                  15

Lys Ile Thr Ile Ser Cys Ser Gly Ser Gly Ser Asn Ile Gly Arg His
            20                  25                  30

Tyr Val Ser Trp Tyr Gln Gln Phe Pro Gly Thr Ala Pro Lys Ile Leu

```
            35                  40                  45
Ile Tyr Asp Asn Asp Lys Arg Pro Ser Gly Ile Ser Asp Arg Phe Ser
 50                  55                  60
Gly Ser Lys Ser Gly Ala Ser Ala Thr Leu Asp Ile Thr Gly Leu Gln
 65                  70                  75                  80
Thr Gly Asp Glu Ala Asp Tyr Tyr Cys Ala Thr Trp Asp Thr Asn Leu
                 85                  90                  95
Ser Gly Gly Val Phe Gly Gly Gly Thr Lys Val Thr Val Leu Gly Gln
                100                 105                 110
Pro Lys Ala Ala Pro Ser Val Thr Leu Phe Pro Pro Ser Ser Glu Glu
            115                 120                 125
Leu Gln Ala Asn Lys Ala Thr Leu Val Cys Leu Ile Ser Asp Phe Tyr
            130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Lys Ser Tyr Ser Cys Gln Val Thr His Glu Gly Ser Thr Val Glu Lys
            195                 200                 205
Thr Val Ala Pro Thr Glu Cys
210                 215

<210> SEQ ID NO 20
<211> LENGTH: 375
<212> TYPE: DNA
<213> ORGANISM: artificial
<220> FEATURE:
<223> OTHER INFORMATION: Heavy Chain Variable Region of Ch6C antibody

<400> SEQUENCE: 20
caggtgcagc tggtgcagtc tgggtctgag gtgaagaagc ctggggcctc agtgaagctt      60
tcctgcaagg cttctggata cacattcact agctactctt tgggctgggt gcgacaggcc     120
cctggacaag gacttgagtg gatgggatgg atcaacacca agactggaaa cccaacttat     180
gcccagggct tcacaggacg gtttgtcttc tccttggaca cgtctgtcaa cacggcatat     240
ctgcagatca ccagcctaaa ggctgaggac actgccgtat atttctgtgc gaaaggaaca     300
ttttactatg ttgggggtcc ttactataat tggttcgacc cctggggcca gggagccctg     360
gtcaccgtct cctca                                                      375

<210> SEQ ID NO 21
<211> LENGTH: 125
<212> TYPE: PRT
<213> ORGANISM: artificial
<220> FEATURE:
<223> OTHER INFORMATION: Heavy Chain Variable Region of Ch6C antibody

<400> SEQUENCE: 21

Gln Val Gln Leu Val Gln Ser Gly Ser Glu Val Lys Lys Pro Gly Ala
  1               5                  10                  15
Ser Val Lys Leu Ser Cys Lys Ala Ser Gly Tyr Thr Phe Thr Ser Tyr
                 20                  25                  30
Ser Leu Gly Trp Val Arg Gln Ala Pro Gly Gln Gly Leu Glu Trp Met
             35                  40                  45
Gly Trp Ile Asn Thr Lys Thr Gly Asn Pro Thr Tyr Ala Gln Gly Phe
```

```
              50                  55                  60
Thr Gly Arg Phe Val Phe Ser Leu Asp Thr Ser Val Asn Thr Ala Tyr
 65                  70                  75                  80

Leu Gln Ile Thr Ser Leu Lys Ala Glu Asp Thr Ala Val Tyr Phe Cys
                 85                  90                  95

Ala Lys Gly Thr Phe Tyr Tyr Gly Trp Gly Pro Tyr Tyr Asn Trp Phe
                100                 105                 110

Asp Pro Trp Gly Gln Gly Ala Leu Val Thr Val Ser Ser
            115                 120                 125
```

<210> SEQ ID NO 22
<211> LENGTH: 1368
<212> TYPE: DNA
<213> ORGANISM: artificial
<220> FEATURE:
<223> OTHER INFORMATION: Heavy Chain of Ch6C antibody

<400> SEQUENCE: 22

```
caggtgcagc tggtgcagtc tgggtctgag gtgaagaagc ctggggcctc agtgaagctt     60
tcctgcaagg cttctggata cacattcact agctactctt tgggctgggt gcgacaggcc    120
cctggacaag gacttgagtg gatgggatgg atcaacacca gactggaaa cccaacttat    180
gcccagggct tcacaggacg gtttgtcttc tccttggaca cgtctgtcaa cacggcatat    240
ctgcagatca ccagcctaaa ggctgaggac actgccgtat attctgtgc gaaggaaca    300
ttttactatg gttggggtcc ttactataat tggttcgacc cctggggcca gggagccctg    360
gtcaccgtct cctcagcctc caccaagggc ccatcggtct tccccctggc accctcctcc    420
aagagcacct ctgggggcac agcggccctg gcctgcctgg tcaaggacta cttccccgaa    480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagagagttg agcccaaatc ttgtgacaaa actcacacat gcccaccgtg cccagcacct    720
gaactcctgg ggggaccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca aagccctccc agcccccatc   1020
gagaaaacca tctccaaagc caagggcag ccccgagaac acaggtgta cacccctgccc   1080
ccatcccggg atgagctgac caagaaccag gtcagcctga cctgcctggt caaaggcttc   1140
tatcccagcg acatcgccgt ggagtgggag agcaatgggc agccggagaa caactacaag   1200
accacgcctc ccgtgctgga ctccgacggc tccttcttcc tctacagcaa gctcaccgtg   1260
gacaagagca ggtggcagca ggggaacgtc ttctcatgct ccgtgatgca tgaggctctg   1320
cacaaccact acacgcagaa gagcctctcc ctgtctccgg gtaaatga               1368
```

<210> SEQ ID NO 23
<211> LENGTH: 455
<212> TYPE: PRT
<213> ORGANISM: artificial
<220> FEATURE:
<223> OTHER INFORMATION: Heavy Chain of Ch6C antibody

<400> SEQUENCE: 23

```
Gln Val Gln Leu Val Gln Ser Gly Ser Glu Val Lys Pro Gly Ala
1               5                   10                  15

Ser Val Lys Leu Ser Cys Lys Ala Ser Gly Tyr Thr Phe Thr Ser Tyr
            20                  25                  30

Ser Leu Gly Trp Val Arg Gln Ala Pro Gly Gln Gly Leu Glu Trp Met
        35                  40                  45

Gly Trp Ile Asn Thr Lys Thr Gly Asn Pro Thr Tyr Ala Gln Gly Phe
50                  55                  60

Thr Gly Arg Phe Val Phe Ser Leu Asp Thr Ser Val Asn Thr Ala Tyr
65                  70                  75                  80

Leu Gln Ile Thr Ser Leu Lys Ala Glu Asp Thr Ala Val Tyr Phe Cys
                85                  90                  95

Ala Lys Gly Thr Phe Tyr Tyr Gly Trp Gly Pro Tyr Tyr Asn Trp Phe
            100                 105                 110

Asp Pro Trp Gly Gln Gly Ala Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 24
<211> LENGTH: 324
<212> TYPE: DNA
<213> ORGANISM: artificial
<220> FEATURE:
<223> OTHER INFORMATION: Light Chain Variable Region of Ch12F antibody

<400> SEQUENCE: 24
gagctcgccc tgactcagcc tgcctccgtg tctgggtctc ctggacagtc gatcaccatc      60
tcctgcactg gaaccagcag tgatgttggt ggttataacg ctgtctcctg gtaccaacag     120
cacccaggca aagcccccaa actcatgatt tatgaggtca ataagcggcc ctcaggggtt     180
tctaatcgct tctctggctc caagtctggc aacacggcct ccctgaccat ctctgggctc     240
caggctgagg acgaggctga ttattactgc agctcatata aagcggagg aactgtggta     300 ttcggcggag ggaccaagct gacc                                            324

<210> SEQ ID NO 25
<211> LENGTH: 108
<212> TYPE: PRT
<213> ORGANISM: artificial
<220> FEATURE:
<223> OTHER INFORMATION: Light Chain Variable Region of Ch12F antibody

<400> SEQUENCE: 25

Glu Leu Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ala Val Ser Trp Tyr Gln Gln His Pro Gly Lys Ala Pro Lys Leu
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Gly
                85                  90                  95

Gly Thr Val Val Phe Gly Gly Gly Thr Lys Leu Thr
            100                 105

<210> SEQ ID NO 26
<211> LENGTH: 646
<212> TYPE: DNA
<213> ORGANISM: artificial
<220> FEATURE:
<223> OTHER INFORMATION: Light Chain of Ch12F antibody

<400> SEQUENCE: 26
gagctcgccc tgactcagcc tgcctccgtg tctgggtctc ctggacagtc gatcaccatc      60
tcctgcactg gaaccagcag tgatgttggt ggttataacg ctgtctcctg gtaccaacag     120
cacccaggca aagcccccaa actcatgatt tatgaggtca ataagcggcc ctcaggggtt     180
tctaatcgct tctctggctc caagtctggc aacacggcct ccctgaccat ctctgggctc     240

```
caggctgagg acgaggctga ttattactgc agctcatata gaagcggagg aactgtggta    300
ttcggcggag ggaccaagct gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tacctgagcc tgacgcccga gcagtggaag tcccacaaaa gctacagctg ccaggtcacg    600
catgaaggga gcaccgtgga agacagtgc ccctacag aatgtt                      646
```

<210> SEQ ID NO 27
<211> LENGTH: 215
<212> TYPE: PRT
<213> ORGANISM: artificial
<220> FEATURE:
<223> OTHER INFORMATION: Light Chain of Ch12F antibody

<400> SEQUENCE: 27

```
Glu Leu Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ala Val Ser Trp Tyr Gln Gln His Pro Gly Lys Ala Pro Lys Leu
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Gly
                85                  90                  95

Gly Thr Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys
    210                 215
```

<210> SEQ ID NO 28
<211> LENGTH: 381
<212> TYPE: DNA
<213> ORGANISM: artificial
<220> FEATURE:
<223> OTHER INFORMATION: Heavy Chain Variable Region of Ch12F antibody

<400> SEQUENCE: 28

```
gaggtgcagc tggtgcagtc tggggcagag gtgaaaaagc ccggggagtc tctgaagata    60
```

```
tcctgtaagg gctctggata cacctttgcc agctactgga tcgtctgggt gcgccagatg    120
cccgggaaag gcctggagta catggggagc atctatcctg gtgactctgg taccagatat    180
agcccgtcct tccgaggcca ggtcaccatc tcagccgaca gtccatcaa  caccgcctac    240 ttgcagtggg gcagcctgaa ggcctcggac accgccttct actactgtgc gagacttaag    300
ccccttcgtg ggtcgttatt cggggagcct attgggccct atgactactg gggccaggca    360
accctggtca ccgtctcctc a                                              381
```

```
<210> SEQ ID NO 29
<211> LENGTH: 127
<212> TYPE: PRT
<213> ORGANISM: artificial
<220> FEATURE:
<223> OTHER INFORMATION: Heavy Chain Variable Region of Ch12F antibody

<400> SEQUENCE: 29
```

```
Glu Val Gln Leu Leu Glu Ser Gly Ala Glu Val Lys Lys Pro Gly Glu
1               5                   10                  15

Ser Leu Lys Ile Ser Cys Lys Gly Ser Gly Tyr Thr Phe Ala Ser Tyr
            20                  25                  30

Trp Ile Val Trp Val Arg Gln Met Pro Gly Lys Gly Leu Glu Tyr Met
        35                  40                  45

Gly Ser Ile Tyr Pro Gly Asp Ser Gly Thr Arg Tyr Ser Pro Ser Phe
    50                  55                  60

Arg Gly Gln Val Thr Ile Ser Ala Asp Lys Ser Ile Asn Thr Ala Tyr
65                  70                  75                  80

Leu Gln Trp Gly Ser Leu Lys Ala Ser Asp Thr Ala Phe Tyr Tyr Cys
                85                  90                  95

Ala Arg Leu Lys Pro Leu Arg Gly Ser Leu Phe Gly Glu Pro Ile Gly
            100                 105                 110

Pro Tyr Asp Tyr Trp Gly Gln Ala Thr Leu Val Thr Val Ser Ser
        115                 120                 125
```

```
<210> SEQ ID NO 30
<211> LENGTH: 1374
<212> TYPE: DNA
<213> ORGANISM: artificial
<220> FEATURE:
<223> OTHER INFORMATION: Heavy Chain of Ch12F antibody

<400> SEQUENCE: 30
```

```
gaggtgcagc tggtgcagtc tggggcagag gtgaaaaagc cggggagtc  tctgaagata     60 tcctgtaagg gctctggata cacctttgcc agctactgga tcgtctgggt gcgccagatg    120
cccgggaaag gcctggagta catggggagc atctatcctg gtgactctgg taccagatat    180
agcccgtcct tccgaggcca ggtcaccatc tcagccgaca gtccatcaa  caccgcctac    240 ttgcagtggg gcagcctgaa ggcctcggac accgccttct actactgtgc gagacttaag    300
ccccttcgtg ggtcgttatt cggggagcct attgggccct atgactactg gggccaggca    360
accctggtca ccgtctcctc agcctccacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtccct caggactcta ctccctcagca gcgtggtgac cgtgccctcc    600
agcagcttgg gcacccagac ctacatctgc aacgtgaatc acaagcccag caacaccaag    660
gtggacaaga gagttgagcc caaatcttgt gacaaaactc acacatgccc accgtgccca    720
```

```
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gatgcatgag   1320
gctctgcaca accactacac gcagaagagc ctctccctgt ctccgggtaa atga         1374
```

<210> SEQ ID NO 31
<211> LENGTH: 457
<212> TYPE: PRT
<213> ORGANISM: artificial
<220> FEATURE:
<223> OTHER INFORMATION: Heavy Chain of Ch12F antibody

<400> SEQUENCE: 31

```
Glu Val Gln Leu Leu Glu Ser Gly Ala Glu Val Lys Lys Pro Gly Glu
1               5                   10                  15

Ser Leu Lys Ile Ser Cys Lys Gly Ser Gly Tyr Thr Phe Ala Ser Tyr
            20                  25                  30

Trp Ile Val Trp Val Arg Gln Met Pro Gly Lys Gly Leu Glu Tyr Met
        35                  40                  45

Gly Ser Ile Tyr Pro Gly Asp Ser Gly Thr Arg Tyr Ser Pro Ser Phe
    50                  55                  60

Arg Gly Gln Val Thr Ile Ser Ala Asp Lys Ser Ile Asn Thr Ala Tyr
65                  70                  75                  80

Leu Gln Trp Gly Ser Leu Lys Ala Ser Asp Thr Ala Phe Tyr Tyr Cys
                85                  90                  95

Ala Arg Leu Lys Pro Leu Arg Gly Ser Leu Phe Gly Glu Pro Ile Gly
            100                 105                 110

Pro Tyr Asp Tyr Trp Gly Gln Ala Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
    195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
```

```
            245                 250                 255
Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Asp Glu Leu
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
    435                 440                 445

Lys Ser Leu Ser Leu Ser Pro Gly Lys
450                 455

<210> SEQ ID NO 32
<211> LENGTH: 324
<212> TYPE: DNA
<213> ORGANISM: artificial
<220> FEATURE:
<223> OTHER INFORMATION: Light Chain Variable Region of Ch8AH8AL
      antibody

<400> SEQUENCE: 32
gagctcgccc tgactcagcc tgcctccgtg tctgggtctc ctggacagtc gatcaccatc      60
tcctgcactg gaggcagaag tgaccttggt gattctaact tgtctcctg gtaccaacaa     120 tacccaggca agccccccaa actcctgatt tatcaggtca ataagaggcc ctcaggggtc     180
cctgatcgct tctctgcgtc caagtctgcc aacacggcct ccctgaccat ctctgggctc     240
caaactgagg acgaggctga ctatttctgc agctcatata caaccaccag tacttatgtc     300
ttcggaattg ggaccaaggt cgtc                                           324

<210> SEQ ID NO 33
<211> LENGTH: 108
<212> TYPE: PRT
<213> ORGANISM: artificial
<220> FEATURE:
<223> OTHER INFORMATION: Light Chain Variable Region of Ch8AH8AL
      antibody

<400> SEQUENCE: 33

Glu Leu Ala Leu Thr Gln Pro Ala Ser Val Ser Gly Ser Pro Gly Gln
1               5                   10                  15

Ser Ile Thr Ile Ser Cys Thr Gly Gly Arg Ser Asp Leu Gly Asp Ser
```

```
                20                  25                  30
Asn Phe Val Ser Trp Tyr Gln Gln Tyr Pro Gly Lys Ala Pro Lys Leu
                35                  40                  45

Leu Ile Tyr Gln Val Asn Lys Arg Pro Ser Gly Val Pro Asp Arg Phe
    50                  55                  60

Ser Ala Ser Lys Ser Ala Asn Thr Ala Ser Leu Thr Ile Ser Gly Leu
65                  70                  75                  80

Gln Thr Glu Asp Glu Ala Asp Tyr Phe Cys Ser Ser Tyr Thr Thr Thr
                85                  90                  95

Ser Thr Tyr Val Phe Gly Ile Gly Thr Lys Val Val
                100                 105
```

<210> SEQ ID NO 34
<211> LENGTH: 646
<212> TYPE: DNA
<213> ORGANISM: artificial
<220> FEATURE:
<223> OTHER INFORMATION: Light Chain of Ch8AH8AL antibody

<400> SEQUENCE: 34

```
gagctcgccc tgactcagcc tgcctccgtg tctgggtctc ctggacagtc gatcaccatc    60
tcctgcactg gaggcagaag tgaccttggt gattctaact tgtctcctg gtaccaacaa    120
tacccaggca agccccccaa actcctgatt tatcaggtca ataagaggcc ctcaggggtc   180
cctgatcgct tctctgcgtc caagtctgcc aacacggcct ccctgaccat ctctgggctc   240
caaactgagg acgaggctga ctatttctgc agctcatata caaccaccag tacttatgtc   300
ttcggaattg ggaccaaggt cgtcgtcctc ggtcagccca aggccaaccc cacagtcacc   360
ctgttcccgc cctcctctga ggagcttcaa gccaacaagg ccacactggt gtgtctcata   420
agtgacttct acccgggagc cgtgacagtg gcctggaagg cagatggcag ccccgtcaag   480
gcgggagtgg agaccaccac accctccaaa caaagcaaca caagtacgc ggccagcagc   540
tacctgagcc tgacgcccga gcagtggaag tcccacagaa gctacagctg ccaggtcacg   600
catgaaggga gcaccgtgga agacagtg gcccctacag aatgtt              646
```

<210> SEQ ID NO 35
<211> LENGTH: 216
<212> TYPE: PRT
<213> ORGANISM: artificial
<220> FEATURE:
<223> OTHER INFORMATION: Light Chain of Ch8AH8AL antibody

<400> SEQUENCE: 35

```
Glu Leu Ala Leu Thr Gln Pro Ala Ser Val Ser Gly Ser Pro Gly Gln
1               5                   10                  15

Ser Ile Thr Ile Ser Cys Thr Gly Gly Arg Ser Asp Leu Gly Asp Ser
                20                  25                  30

Asn Phe Val Ser Trp Tyr Gln Gln Tyr Pro Gly Lys Ala Pro Lys Leu
                35                  40                  45

Leu Ile Tyr Gln Val Asn Lys Arg Pro Ser Gly Val Pro Asp Arg Phe
    50                  55                  60

Ser Ala Ser Lys Ser Ala Asn Thr Ala Ser Leu Thr Ile Ser Gly Leu
65                  70                  75                  80

Gln Thr Glu Asp Glu Ala Asp Tyr Phe Cys Ser Ser Tyr Thr Thr Thr
                85                  90                  95

Ser Thr Tyr Val Phe Gly Ile Gly Thr Lys Val Val Val Leu Gly Gln
                100                 105                 110
```

```
Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215
```

<210> SEQ ID NO 36
<211> LENGTH: 363
<212> TYPE: DNA
<213> ORGANISM: artificial
<220> FEATURE:
<223> OTHER INFORMATION: Heavy Chain Variable Region for Ch8AH8AL
      antibody

<400> SEQUENCE: 36

```
gaggtgcagc tggtggagtc tgggggaggc ttaataaagc ctgggggatc cctgagactc      60
tcctgtgcag cctctggatt catctttagg gactataata tcaactgggt ccgccaggct     120
ccagggaagg ggctggagtg gctaggtttc ataaggacca gagcttcagg ccggtcaaca     180
gagtacagcg catctgtgaa aggcagattc actatctcaa gagatgattc aaaaacatt     240 gcctatctac acatcaatag cctgaaaatg gaggacacag ccgtgtatta ttgtgctaag     300 aaagggggaca gttactacta catggacttc tggggcaaag ggaccgcggt caccgtctcc    360
tca                                                                   363
```

<210> SEQ ID NO 37
<211> LENGTH: 121
<212> TYPE: PRT
<213> ORGANISM: artificial
<220> FEATURE:
<223> OTHER INFORMATION: Heavy Chain Variable Region for Ch8AH8AL
      antibody

<400> SEQUENCE: 37

```
Glu Val Gln Leu Val Glu Ser Gly Gly Gly Leu Ile Lys Pro Gly Gly
1               5                   10                  15

Ser Leu Arg Leu Ser Cys Ala Ala Ser Gly Phe Ile Phe Arg Asp Tyr
            20                  25                  30

Asn Ile Asn Trp Val Arg Gln Ala Pro Gly Lys Gly Leu Glu Trp Leu
        35                  40                  45

Gly Phe Ile Arg Thr Arg Ala Ser Gly Arg Ser Thr Glu Tyr Ser Ala
    50                  55                  60

Ser Val Lys Gly Arg Phe Thr Ile Ser Arg Asp Asp Ser Lys Asn Ile
65                  70                  75                  80

Ala Tyr Leu His Ile Asn Ser Leu Lys Met Glu Asp Thr Ala Val Tyr
                85                  90                  95
```

Tyr Cys Ala Lys Lys Gly Asp Ser Tyr Tyr Tyr Met Asp Phe Trp Gly
            100                 105                 110

Lys Gly Thr Ala Val Thr Val Ser Ser
        115                 120

<210> SEQ ID NO 38
<211> LENGTH: 1356
<212> TYPE: DNA
<213> ORGANISM: artificial
<220> FEATURE:
<223> OTHER INFORMATION: Heavy Chain of Ch8AH8AL antibody

<400> SEQUENCE: 38

| | | | | | |
|---|---|---|---|---|---|
| gaggtgcagc | tggtggagtc | tgggggaggc | ttaataaagc | ctgggggatc | cctgagactc | 60 |
| tcctgtgcag | cctctggatt | catctttagg | gactataata | tcaactgggt | ccgccaggct | 120 |
| ccagggaagg | ggctggagtg | gctaggtttc | ataaggacca | gagcttcagg | ccggtcaaca | 180 |
| gagtacagcg | catctgtgaa | aggcagattc | actatctcaa | gagatgattc | caaaaacatt | 240 |
| gcctatctac | acatcaatag | cctgaaaatg | gaggacacag | ccgtgtatta | ttgtgctaag | 300 |
| aaagggggaca | gttactacta | catggacttc | tggggcaaag | ggaccgcggt | caccgtctcc | 360 |
| tcagcctcca | ccaagggccc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gagagttgag | 660 |
| cccaaatctt | gtgacaaaac | tcacacatgc | ccaccgtgcc | cagcacctga | actcctgggg | 720 |
| ggaccgtcag | tcttcctctt | ccccccaaaa | cccaaggaca | cctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgtgtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggat | 1080 |
| gagctgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tacagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaatga | | | 1356 |

<210> SEQ ID NO 39
<211> LENGTH: 451
<212> TYPE: PRT
<213> ORGANISM: artificial
<220> FEATURE:
<223> OTHER INFORMATION: Heavy Chain of Ch8AH8AL antibody

<400> SEQUENCE: 39

Glu Val Gln Leu Val Glu Ser Gly Gly Gly Leu Ile Lys Pro Gly Gly
1               5                   10                  15

Ser Leu Arg Leu Ser Cys Ala Ala Ser Gly Phe Ile Phe Arg Asp Tyr
            20                  25                  30

```
Asn Ile Asn Trp Val Arg Gln Ala Pro Gly Lys Gly Leu Glu Trp Leu
        35                  40                  45
Gly Phe Ile Arg Thr Arg Ala Ser Gly Arg Ser Thr Glu Tyr Ser Ala
50                      55                  60
Ser Val Lys Gly Arg Phe Thr Ile Ser Arg Asp Asp Ser Lys Asn Ile
65                  70                  75                  80
Ala Tyr Leu His Ile Asn Ser Leu Lys Met Glu Asp Thr Ala Val Tyr
                85                  90                  95
Tyr Cys Ala Lys Lys Gly Asp Ser Tyr Tyr Met Asp Phe Trp Gly
                100                 105                 110
Lys Gly Thr Ala Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
            435                 440                 445

Pro Gly Lys
    450

<210> SEQ ID NO 40
<211> LENGTH: 87
<212> TYPE: PRT
<213> ORGANISM: artificial
<220> FEATURE:
<223> OTHER INFORMATION: Viral protein A33 epitope for Ch12F antibody

<400> SEQUENCE: 40

Ser Cys Asn Gly Leu Tyr Tyr Gln Gly Ser Cys Tyr Ile Leu His Ser
1               5                   10                  15

Asp Tyr Gln Leu Phe Ser Asp Ala Lys Ala Asn Cys Thr Ala Glu Ser
            20                  25                  30

Ser Thr Leu Pro Asn Lys Ser Asp Val Leu Ile Thr Trp Leu Ile Asp
        35                  40                  45

Tyr Val Glu Asp Thr Trp Gly Ser Asp Gly Asn Pro Ile Thr Lys Thr
    50                  55                  60

Thr Ser Asp Tyr Gln Asp Ser Asp Val Ser Gln Glu Val Arg Lys Tyr
65                  70                  75                  80

Phe Cys Val Lys Thr Met Asn
                85

<210> SEQ ID NO 41
<211> LENGTH: 111
<212> TYPE: PRT
<213> ORGANISM: artificial
<220> FEATURE:
<223> OTHER INFORMATION: B5 viral protein epitope for Ch8AH8AL antibody

<400> SEQUENCE: 41

Thr Cys Thr Val Pro Thr Met Asn Asn Ala Lys Leu Thr Ser Thr Glu
1               5                   10                  15

Thr Ser Phe Asn Asp Lys Gln Lys Val Thr Phe Thr Cys Asp Gln Gly
            20                  25                  30

Tyr His Ser Ser Asp Pro Asn Ala Val Cys Glu Thr Asp Lys Trp Lys
        35                  40                  45

Tyr Glu Asn Pro Cys Lys Lys Met Cys Thr Val Ser Asp Tyr Ile Ser
    50                  55                  60

Glu Leu Tyr Asn Lys Pro Leu Tyr Glu Val Asn Ser Thr Met Thr Leu
65                  70                  75                  80

Ser Cys Asn Gly Glu Thr Lys Tyr Phe Arg Cys Glu Glu Lys Asn Gly
                85                  90                  95

Asn Thr Ser Trp Asn Asp Thr Val Thr Cys Pro Asn Ala Glu Cys
                100                 105                 110

<210> SEQ ID NO 42
<211> LENGTH: 22
<212> TYPE: DNA
<213> ORGANISM: artificial
<220> FEATURE:
<223> OTHER INFORMATION: SJ15R primer

<400> SEQUENCE: 42
ggtcactgtc actggctcag gg                                          22
```

```
<210> SEQ ID NO 43
<211> LENGTH: 28
<212> TYPE: DNA
<213> ORGANISM: artificial
<220> FEATURE:
<223> OTHER INFORMATION: SJ16R primer

<400> SEQUENCE: 43
aggcggatcc aggggccagt ggatagac                                    28

<210> SEQ ID NO 44
<211> LENGTH: 27
<212> TYPE: DNA
<213> ORGANISM: artificial
<220> FEATURE:
<223> OTHER INFORMATION: lgh249r primer

<400> SEQUENCE: 44
cttccacttg acattgatgt ctttggg                                     27
```